US008299335B2

(12) United States Patent
Malvar et al.

(10) Patent No.: US 8,299,335 B2
(45) Date of Patent: Oct. 30, 2012

(54) CORN SEED COMPRISING NOVEL OPAQUE MODIFIERS AND RELATED METHODS

(75) Inventors: Thomas Malvar, North Stonington, CT (US); Shihshieh Huang, Woodland, CA (US); Alessandra Frizzi, Davis, CA (US); Mike Kerns, Ankeny, IA (US)

(73) Assignee: Monsanto Technology LLC, St. Louis, MO (US)

( * ) Notice: Subject to any disclaimer, the term of this patent is extended or adjusted under 35 U.S.C. 154(b) by 387 days.

(21) Appl. No.: 12/413,949

(22) Filed: Mar. 30, 2009

(65) Prior Publication Data

US 2009/0246350 A1 Oct. 1, 2009

Related U.S. Application Data

(60) Provisional application No. 61/072,633, filed on Apr. 1, 2008, provisional application No. 61/041,035, filed on Mar. 31, 2008.

(51) Int. Cl.
*A01H 5/00* (2006.01)
*C12N 15/82* (2006.01)

(52) U.S. Cl. .................................... 800/320.1; 800/278

(58) Field of Classification Search ........................ None
See application file for complete search history.

(56) References Cited

U.S. PATENT DOCUMENTS

| | | | |
|---|---|---|---|
| 5,492,547 | A | 2/1996 | Johnson |
| 5,981,832 | A | 11/1999 | Johnson |
| 7,232,945 | B1 | 6/2007 | Peters |
| 7,414,181 | B1 | 8/2008 | Eichelberger |
| 2005/0204418 | A1 | 9/2005 | Jung et al. |
| 2006/0075515 | A1 | 4/2006 | Luethy et al. |
| 2006/0200878 | A1 | 9/2006 | Lutfiyya et al. |

FOREIGN PATENT DOCUMENTS

WO 2006/099249 A2 9/2006

OTHER PUBLICATIONS

International Search Report and Written Opinion dated Jul. 10, 2009 for PCT/US2009/038731 filed Mar. 30, 2009, 19 pages.

Huang, S. et al., "Improving Nutritional Quality of Maize Proteins by Expressing Sense and Antisense Zein Genes", Journal of Agricultural and Food Chemistry, Apr. 7, 2004, pp. 1958-1964, vol. 52, No. 7, American Chemical Society, Washington, US.

Dannenhoffer, Joanne M., et al., "Opaque-15, A Maize Mutation with Properties of a Defective Opaque-2 Modifier", Proceedings of the National Academy of Sciences of the United States of America, Mar. 1995, pp. 1931-1935, vol. 92, No. 6.

Huang, S., et al., "High Lysine and High Tryptophan Transgenic Maize Resulting from the Reduction of Both 19 and 22-kD [alpha]-zeins", Plant Molecular Biology, Jun. 1, 2006, pp. 525-535, vol. 61, No. 3, Kluwer Academic Publishers, Dordrecht, NL.

Segal, G., et al., "A New Opaque Variant of Maize by a Single Dominant RNA-Interference-Inducing Transgene", Genetics, Sep. 1, 2003, pp. 387-397, vol. 165, No. 1, Genetics Society of America, Austin, TX.

Krivanek, Alan F., et al., "Breeding and Disseminating Quality Protein Maize (QPM) for Africa", African Journal of Biotechnology, Feb. 19, 2007, pp. 312-324, vol. 6, No. 4.

Geetha, K.B., et al., "Opaque-2 Modifiers Increase Gamma Zein Synthesis and Alter its Spatial Distribution in Maize Endosperm", Plant Cell, Nov. 1991, pp. 1207-1219, vol. 3., No. 11.

Gibbon, Bryan C., et al., "Molecular Genetic Approaches to Developing Quality Protein Maize", Trends in Genetics, Apr. 1, 2005, pp. 227-233, vol. 21, No. 4, Elsevier Science Publishers B.V., Amsterdam, NL.

Holding, David R., et al., "Genetic Analysis of Opaque-2 Modifier Loci in Quality Protein Maize", Theoretical and Applied Genetics, International Journal of Plant Breeding, Apr. 22, 2008, pp. 157-170, vol. 117, No. 2, Springer, Berlin, DE.

Marocco, Adriano, et al., Three High-Lysine Mutations Control the Level of ATP-Binding HSP70-like Proteins in the Maize Endosperm, The Plant Cell, May 1991, 507-515, vol. 3.

Coleman, Craig E., et al., A Defective Signal Peptide in the Maize High-Lysine Mutant Floury 2, Proceedings of the National Academy of Science, Jul. 1995, 6828-6831, vol. 92.

Aukerman, Milo J., et al., A 168 bp Derivative of Suppressor-mutator/Enhancer is responsible for the Maize o2-23 Mutation, Plant Molecular Biology, 1993, 355-362, vol. 21.

Lopes, Mauricio A., et al., Gamma-Zein Content is Related to Endosperm Modification in Quality Protein Maize, Crop Science, 1991, 1655-1662, vol. 31.

Wallace, John C., et al., New Methods for Extraction and Quantitation of Zeins Reveal a High Content of gamma-Zein in Modified opaque-2 Maize, Plant Physiology, 1990, 191-196, vol. 92.

Lopes, Mauricio A., Identification of Two Opaque2 Modifier Loci in Quality Protein Maize, Molecular and General Genetics, 1995, 603-613, vol. 247.

Harper, A.E., et al., Effects of Ingestion of Disproportionate Amounts of Amino Acids, Physiological Reviews, Jul. 1970, 428-558, vol. 50 No. 8.

Harper A.E., et al., L-Leucine, an Isoleucine Antagonist in the Rat, Archives Biochem and Biophys, 1955, 1-12, vol. 57.

May, Robert C., et al., Leucine-Induced Amino Acid Antagonism in Rats: Muscle Valine Metabolism and Growth Impairment, The Journal of Nutrition, 1991, 293-301.

Adams, Whitney R., Matrix-Assisted Laser Desorption Ionization Time-of-Flight Mass Spectrometry Analysis of Zeins in Mature Maize Kernels, Journal of Agricultural and Food Chemistry, 2004, 1842-1849. vol. 52.

Wu et al., "γ-Zeins are essential for endosperm modification in quality protein maize", Proceeding of the National Academy of Sciences, Jul. 20, 2010, pp. 12810-12815, vol. 107, No. 29.

International Preliminary Report on Patentability for PCT/US2009/038731, issued on Jun. 11, 2010, 11 pages.

Arcalis, Elsa et al., The Changing Fate of a Secretory Glycoprotein in Developing Maize Endosperm, Plant Physiology, Jun. 2010, pp. 693-702, vol. 153.

*Primary Examiner* — Elizabeth McElwain

(74) *Attorney, Agent, or Firm* — Thompson Coburn LLP; Charles P. Romano; Chunping Li

(57) ABSTRACT

Novel corn opaque modifier loci, associated molecular markers and methods for obtaining the loci, markers, and resultant seed are provided. Vitreous seed with reduced alpha-zein storage protein content that contain the opaque modifier loci are also described. Processes for obtaining milled corn seed products from the vitreous seed with reduced alpha-zein storage protein content that contain the opaque modifier loci are also provided.

12 Claims, 7 Drawing Sheets

CORN SEED COMPRISING NOVEL OPAQUE MODIFIERS AND RELATED METHODS

CROSS-REFERENCE TO RELATED APPLICATIONS

This application claims benefit of priority to U.S. Provisional Application Ser. No. 61/041,035 filed Mar. 31, 2008 and U.S. Provisional Application Ser. No. 61/072,633 filed Apr. 1, 2008, both of which are incorporated herein by reference in their entireties.

INCORPORATION OF SEQUENCE LISTING

An electronic form of the sequence listing is contained in the file named "38_15(55196)C_US.txt", which is 117663 bytes (as measured in MS-DOS) and comprises 111 sequences, is filed herewith and is incorporated herein by reference in its' entirety.

STATEMENT REGARDING FEDERALLY SPONSORED RESEARCH OR DEVELOPMENT

Not Applicable.

APPENDIX

Not Applicable.

SUMMARY OF THE INVENTION

This invention provides corn seeds comprising decreased alpha-zein storage protein content and genetic loci that provide for a vitreous phenotype in such seed. The invention further provides methods for obtaining seed with reduced alpha-zein seed storage protein content and a vitreous phenotype as well as molecular markers that are useful for introgressing genetic loci that provide for a vitreous phenotype in seed with reduced alpha-zein content. In general, these methods and molecular markers can be used to obtain seeds with the desired vitreous phenotype and reduced alpha-zein storage protein content from corn plants from the genus *Zea*. More specifically, seeds from the species *Zea mays* and the subspecies *Zea mays L.* ssp. *Mays* with the desired vitreous phenotype and reduced alpha-zein storage protein content are provided for and obtainable by these methods. In an additional aspect, seeds is from a corn plant from the group *Zea mays L.* subsp. *mays Indentata*, otherwise known as dent corn are provided for and obtainable by these methods. In another aspect, seeds from a corn plant from the group *Zea mays L.* subsp. *mays Indurata*, otherwise known as flint corn are provided for and obtainable by these methods. In another aspect, seeds from a corn plant from the group *Zea mays L.* subsp. *mays Saccharata*, otherwise known as sweet corn, are provided for and obtainable by these methods. In another aspect, seeds from a corn plant from the group *Zea mays L.* subsp. *mays Amylacea*, otherwise known as flour corn, are provided for and obtainable by these methods. In a further aspect, seeds from a corn plant from the group *Zea mays L.* subsp. *mays Everta*, otherwise known as pop corn, are provided for and obtainable by these methods. It is further understood that the seeds or opaque modifier loci of this invention can be obtained from *Zea* or corn plants that include, but are not limited to, hybrids, inbreds, partial inbreds, or members of defined or undefined populations.

In one embodiment, the invention provides corn seed comprising a vitreous kernel phenotype, at least one transgene that imparts to the corn seed an alpha-zein storage protein content which is reduced relative to control seed, and at least one opaque modifier locus that imparts the vitreous kernel phenotype to the seed comprising the transgene.

The invention also provides a corn seed comprising a vitreous kernel phenotype, at least one genetic element that imparts to the corn seed an alpha-zein storage protein content which is reduced relative to a control seed, and at least one opaque modifier locus that imparts the vitreous kernel phenotype to the seed comprising the genetic element, wherein a 27 kilodalton (kD) gamma zein storage protein content in the corn seed is not significantly increased. The corn seed of the invention can comprise a 27 kD gamma zein storage protein content that is less than 2-fold higher than that of a seed of the same variety that contains the genetic element but lacks the opaque modifier. Alternatively, the corn seed of the invention can comprise a 27 kD gamma zein storage protein content that is less than 1.8-fold, less than 1.5 fold, less than 1.2 fold, or less than 1.1 fold higher than that of seed of the same variety that contain the genetic element but lacks the opaque modifier.

In certain embodiments, the genetic element of the seed comprises recombinant DNA. In still other embodiments, the recombinant DNA reduces expression of both 19 kD and 22 kD alpha-zein storage proteins. The recombinant DNA can comprises in 5' to 3' order a promoter element operably linked to an anti-sense-oriented DNA element 1 from a 19 kD alpha-zein gene, an anti-sense-oriented DNA element 2 from a 22 kD alpha-zein gene, a sense-oriented DNA element 3 from the 22 kD alpha-zein gene that is shorter than the anti-sense-oriented DNA element 2 and is complementary to only the 5' end of element 2 and a sense-oriented DNA element 4 from a 19 kD alpha-zein gene that is complementary to at least a portion of the 5' end of element 1. In still other embodiments, the recombinant DNA can comprise a vector that provides for expression of a 24 kD alpha-zein protein obtained from a floury-2 mutant in the corn seed.

In certain embodiments, the genetic element of the seed of the invention comprise at least one genetic locus that imparts to the corn seed an alpha-zein storage protein content which is reduced relative to seed of the same variety that lacks the genetic locus. In certain embodiments, the genetic loci is a DeB30 locus, a Mucronate locus, floury-2 locus, a floury-3 locus, an opaque-2 locus, an opaque-6 locus or an opaque-7 locus.

Corn seed of the invention can comprise an alpha-zein storage protein content that is of less than 50% of an alpha-zein seed storage protein content of control seed. In other embodiments, the seed can comprise an alpha-zein storage protein content is of less than about 10%, less than about 5%, or less than about 1% of an alpha-zein seed storage protein content of control seed. Corn seed of the invention can have a total lysine content in the range of about 3000 to about 5300 ppm by weight. In certain embodiments, the corn seed of the invention can have a kernel density of at least about 1.24 grams/milliliter. In certain embodiments, the corn seed of the invention have a reduced alpha-zein storage protein content that comprises a substantial reduction in 19 kD and 22 kD alpha zein storage proteins.

In certain embodiments, the corn seed can comprises at least one genetic locus present in corn line I283669 germplasm, wherein the genetic locus is linked to a marker selected from Table 4. In still other embodiments, the corn seed can comprise at least one genetic locus present in corn line I226211 germplasm, wherein the genetic locus is linked to a marker selected from Table 3. In still other embodiments, the corn seed of the invention does not comprise an opaque modifier selected from the group consisting of in Pool 15, Pool 17, Pool 18, Pool 23, Pool 24, Pool 25, Pool 26, Pool 27, Pool 29, Pool 31, Pool 32, Pool 33 or Pool 34 QPM (Quality Protein Maize) opaque modifiers.

The invention provides for a corn plant obtained from the seed of the invention. The invention also provides processed products of the seed of the invention wherein the product is a feed, a meal, or a partially purified protein composition.

Methods for obtaining the seeds of the invention are also provided. In one embodiment, a method for obtaining a corn seed comprising a vitreous kernel phenotype and a reduced alpha-zein storage protein content that comprises the steps of: (a) crossing a corn line comprising an opaque kernel phenotype and a transgene that reduces seed alpha-zein storage protein content relative to seed of the same variety that does not contain the transgene with a genetically distinct corn line; and (b) selecting a seed harvested from a progeny plant of the cross of step (a) for both the transgene and a vitreous kernel phenotype is provided. In certain embodiments, the genetically distinct corn line of the method is a corn line that yields seed with a high density kernel. The high density kernel of the genetically distinct corn line can have a density of at least about 1.24 grams/milliliter. In other embodiments of the method, the transgene of step (a) that reduces expression of an alpha-zein storage protein is a transgene that reduces both 19 kD and 22 kD alpha-zein storage protein. In still other embodiments of the method, the genetically distinct corn line of step (a) comprises I283669 germplasm, I226211 germplasm, or a combination thereof. The genetically distinct corn line of step (a) can also comprise at least one genetic locus comprising an allele of the locus present in I283669 germplasm that is linked to a marker identified in Table 4. The marker identified in Table 4 can be selected from the group consisting of SEQ ID NO: 102-111. The genetically distinct corn line of step (a) can also comprise at least one genetic locus comprising an allele of the locus present in I226211 germplasm that is linked to a marker identified in Table 3. The marker identified in Table 3 can be selected from the group consisting of SEQ ID NO:1-101.

Methods for identifying an opaque modifier locus are also provided. The methods of identifying an opaque modifier locus can comprise the steps of: (a) crossing a corn line comprising an opaque kernel phenotype and a transgene that reduces seed alpha-zein storage protein content relative to seed of the same variety that does not contain the transgene with a genetically distinct corn line; (b) selecting a seed harvested from a progeny plant of the cross of step (a) for both the transgene and a vitreous kernel phenotype, and (c) mapping one or more genetic loci present in the seed harvested in step (b) that provide a vitreous phenotype to seed with a reduced alpha-zein storage protein content, thereby identifying an opaque modifier locus.

In other embodiments of the aforementioned methods of the invention, the genetically distinct corn line of step (a) can comprise at least two genetic loci comprising an allele of the loci present in I283669 germplasm, I226211 germplasm, or a combination thereof, wherein the genetic loci are linked to at least one marker identified in Table 3 and/or Table 4.

In certain embodiments of the aforementioned methods of the invention, the transgene is selected in step (b) by determining an alpha-zein storage protein content that is reduced relative to seed of the same variety that does not contain the transgene in an assay. The assay can be a chromatographic assay, an immunoassay, an electrophoretic assay, an mass spectrometric assay, a protein staining assay, or any combination thereof.

In other embodiments of the aforementioned methods of the invention, the transgene is selected in step (b) by selecting for a selectable or scoreable marker that is linked to the transgene. The selectable marker can be a gene encoding a protein selected from the group consisting of a neomycin phosphotransferase, a phosphinothricin acetyltransferase, a glyphosate resistant 5-enol-pyruvylshikimate-3-phosphate synthase (EPSPS), a hygromycin phosphotransferase, a dihydropteroate synthase, a sulfonylurea insensitive acetolactate synthase, an atrazine insensitive Q protein, a nitrilase protein capable of degrading bromoxynil, a dehalogenase protein capable of degrading dalapon, a 2,4-dichlorophenoxyacetate monoxygenase, a methotrexate insensitive dihydrofolate reductase, and an aminoethylcysteine insensitive octopine synthase.

In other embodiments of the aforementioned methods of the invention, a vitreous kernel phenotype is selected in step (b) in an assay that identifies translucent kernels or in an assay that identifies seed with increased density. In certain embodiments, seed with increased density are identified with a Near Infrared Transmittance (NIT) assay. In still other embodiments, seed with a density of at least about 1.24 grams/milliliter are selected.

Any of the methods of the invention can further comprise the step of determining a gamma zein storage protein content in the harvested seed of step (b) to obtain a seed with a vitreous kernel phenotype and a reduced alpha-zein storage protein content, wherein a 27 kD gamma zein storage protein content in the corn seed is less than 2-fold higher than that of seed of the same variety that contain the transgene but lacks an opaque modifier. Any of the methods of the invention can also further comprise the steps of growing a plant from the corn seed obtained in step (b) that comprises a vitreous kernel phenotype and a reduced alpha-zein storage protein content and obtaining progeny seed from that plant.

The invention also provides processes for obtaining corn seed products from the aforementioned corn seeds provided by the invention. In one embodiment, processes of the invention comprise the steps of: a) milling a corn seed that comprises a vitreous kernel phenotype, at least one transgene that imparts to the corn seed an alpha-zein storage protein content which is reduced relative to control seed, and at least one opaque modifier locus that imparts the vitreous kernel phenotype to the seed comprising the transgene; and b) collecting milled seed material from step (a) to obtain a corn seed product. A corn seed product of this process can be a feed or a meal. Alternatively, the process can further comprise the step of extracting proteins from the milled seed material of step (b) to obtain a partially purified protein composition. In this case, the corn seed product of the process is a partially purified protein composition. In another embodiment, processes of the invention comprise the steps of: a) milling a corn seed that comprises a vitreous kernel phenotype, at least one genetic element that imparts to the corn seed an alpha-zein storage protein content which is reduced relative to a control seed, and at least one opaque modifier locus that imparts the vitreous kernel phenotype to the seed comprising the genetic element, wherein a 27 kD gamma zein storage protein content in the corn seed is not significantly increased; and b) collecting milled seed material from step (a) to obtain a corn seed product. A corn seed product of this process can be a feed or a meal. Alternatively, the process can further comprise the step of extracting proteins from the milled seed material of step (b) to obtain a partially purified protein composition.

Also provided herein are corn genomic DNA having a genetic element that imparts to a corn seed (a) enhanced nutritional value from an increase in lysine and tryptophan, and (b) soft, brittle and opaque kernel shells, both resulting from a reduced alpha-zein storage protein content in the range of at least 10% to at least 50% reduction as compared to control, the improvement comprising the presence of at least one stably introduced opaque modifier locus on at least one chromosome wherein the opaque modifier locus restores kernel hardness and does not result in a significant increase in a 27 kilodalton gamma zein storage protein content, and wherein the kernel hardness is observable by the presence of a vitreous kernel. In certain embodiments, the opaque modifier locus is introduced by introgression from corn variety I226211 or I283669 or progeny thereof. In certain embodiments, the opaque modifier locus restores seed density to at least 1.24 grams per milliliter. In certain embodiments, the genetic element is one or more recombinant DNA(s) that reduce(s) expression of both 19 kilodalton (kD) and 22 kilodalton (kD) alpha-zein storage proteins. In certain embodiments, the recombinant DNA comprises in 5' to 3' order a promoter element operably linked to an anti-sense-oriented DNA element 1 from a 19 kD alpha-zein gene, an anti-sense-oriented DNA element 2 from a 22 kD alpha-zein gene, a sense-oriented DNA element 3 from the 22 kD alpha-zein gene that is shorter than the anti-sense-oriented DNA element 2 and is complementary to only the 5' end of element 2 and a sense-oriented DNA element 4 from a 19 kD alpha-zein gene that is complementary to at least a portion of the 5' end of element 1. In still other embodiments, the recombinant DNA comprises a vector that provides for expression of a 24 kilodalton alpha-zein protein obtained from a floury-2 mutant in the corn seed. In other embodiments, the genetic element comprises at least one genetic locus that imparts to the corn seed an alpha-zein storage protein content which is reduced relative to seed of the same variety that lacks the genetic locus. In certain embodiments, the genetic locus is a DeB30 locus, a Mucronate locus, floury-2 locus, a floury-3 locus, an opaque-2 locus, an opaque-6 locus or an opaque-7 locus. In certain embodiments, the 27 kilodalton gamma zein storage protein content in a corn seed comprising the genetic element and the opaque modifier is less than 2.0-fold higher than that of seed of the same variety that contain the genetic element but lacks the opaque modifier. In other embodiments, the 27 kilodalton gamma zein storage protein content is less than 1.5-fold higher than that of seed of the same variety that contain the genetic element but lacks the opaque modifier. In certain embodiments, seed having the genetic element and the opaque modifier comprise an alpha-zein storage protein content is of less than 50% of an alpha-zein seed storage protein content of control seed. In other embodiments, the seed has an alpha-zein storage protein content is of less than about 10% of an alpha-zein seed storage protein content of control seed, is of less than about 5% of an alpha-zein seed storage protein content of control seed, or is of less than 1% of an alpha-zein seed storage protein content of control seed. In certain embodiments, a total lysine content of seed having the genetic element and the opaque modifier is in the range of about 3000 to about 5300 ppm by weight. In certain embodiments, the opaque modifier comprises at least one genetic locus present in corn line I283669 germplasm, in corn line I226211 germplasm, or a combination thereof. In certain embodiments, the opaque modifier comprises at least one genetic locus present in corn line I283669 germplasm and wherein the genetic locus is linked to a marker selected from Table 4. In certain embodiments, the opaque modifier comprises at least one genetic locus present in corn line I226211 germplasm and wherein the genetic locus is linked to a marker selected from Table 3. In still other embodiments, the opaque modifier does not comprise an opaque modifier selected from the group consisting of Pool 15, Pool 17, Pool 18, Pool 23, Pool 24, Pool 25, Pool 26, Pool 27, Pool 29, Pool 31, Pool 32, Pool 33 or Pool 34 QPM (Quality Protein Maize) opaque modifiers.

Also provided are methods for obtaining a corn kernel having enhanced nutritional value comprising harvesting seed produced from at least one parental corn line comprising corn genomic DNA having a genetic element that imparts to a corn seed (a) enhanced nutritional value from an increase in lysine and tryptophan, and (b) soft, brittle and opaque kernel shells, both resulting from a reduced alpha-zein storage protein content in the range of at least 10% to at least 50% reduction as compared to control, the improvement comprising the presence of at least one stably introduced opaque modifier locus on at least one chromosome wherein the opaque modifier locus restores kernel hardness and does not result in a significant increase in a 27 kilodalton gamma zein storage protein content, and wherein the kernel hardness is observable by the presence of a vitreous kernel. In certain embodiments, the opaque modifier comprises at least one genetic locus present in corn line I283669 germplasm, in corn line I226211 germplasm, or a combination thereof.

DETAILED DESCRIPTION OF THE INVENTION

I. Definitions

Figure 1:
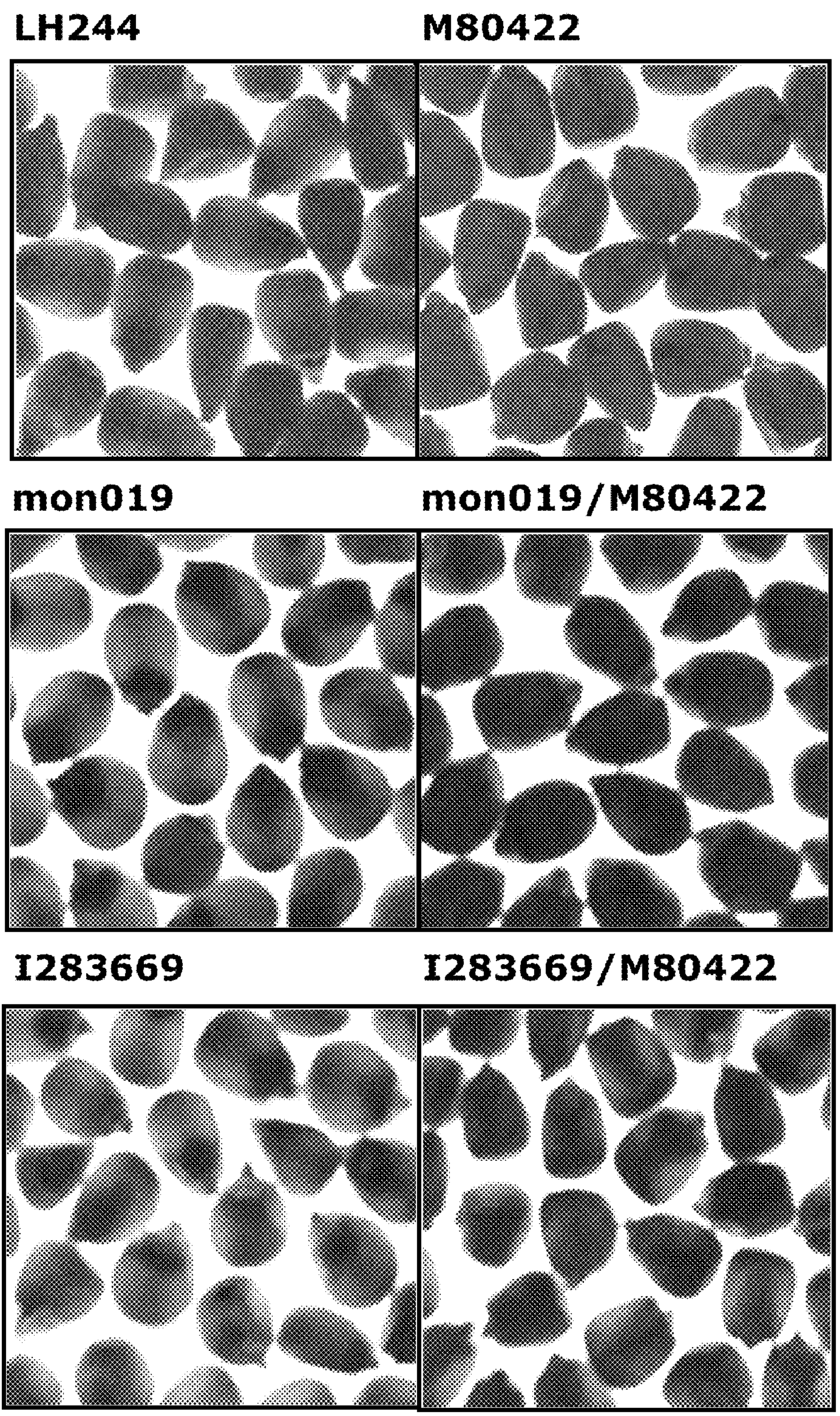
FIG. 1 illustrates the restoration of the vitreous kernel phenotype to corn seed comprising the MON80442 transgene insertion that reduces alpha-zein storage protein content by the I283669 modifier loci or locus. Backlit photographs of maize kernels are shown. LH244, mon019 and I283669 are the inbred parental lines. M80442 is a transgenic zein suppression event in the LH244 genetic background. Kernels of mon019/M80442 are the F1 seed from a cross between mon019 and M80442. Kernels of I283669/M80442 are the F1 seed from a cross between I283669 and M80442.
Figure 2:
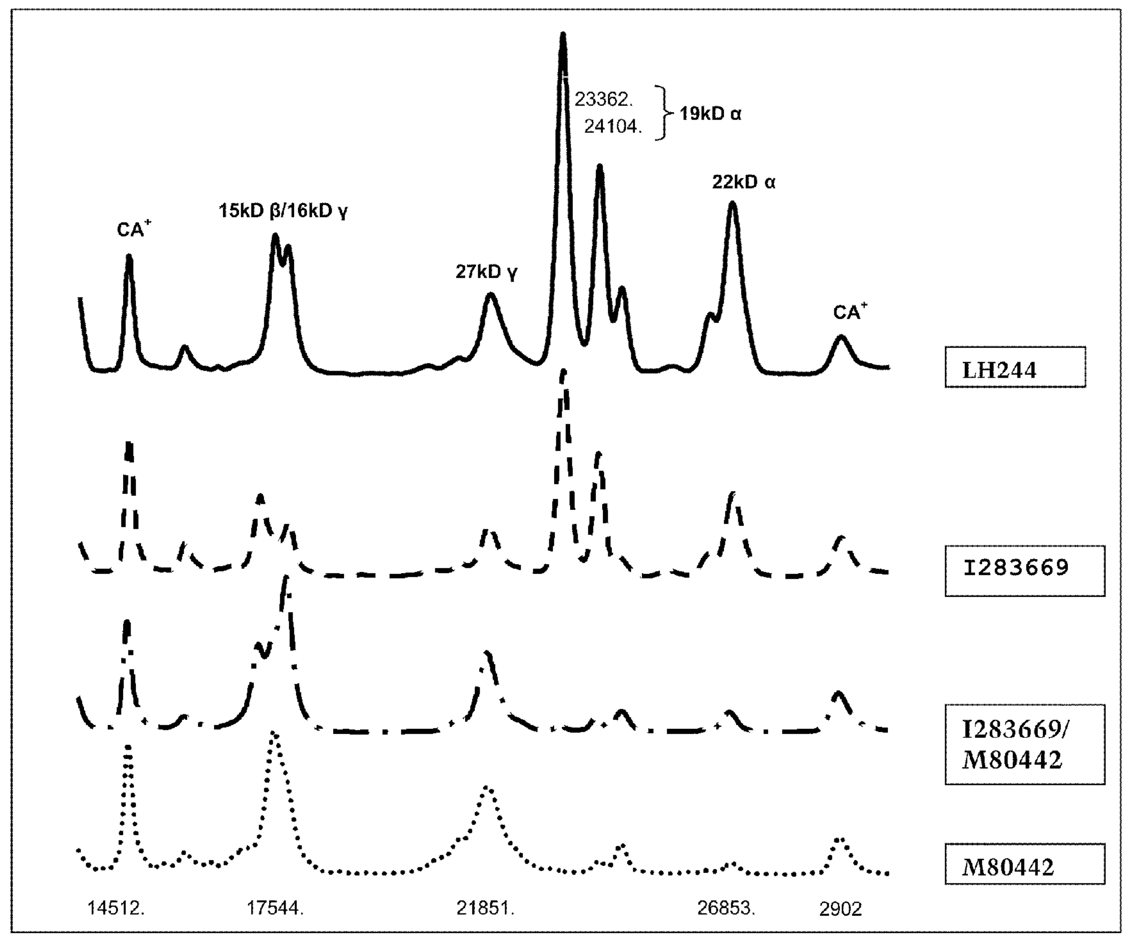
FIG. 2 illustrates the content of various seed and reference proteins in corn seed derived from various genetic backgrounds. MALDI-TOF MS traces from inbred line I283669, LH244, transgenic line M80442, and the F1 seed from a cross between I283669 and M80442 (I283669/M80442) showing the reduction in 19 kD and 22 kD zeins in M80442 and I283669/M80442. The content of the 27 kDa gamma zein is not significantly increased in vitreous I283669/M80442 kernels relative to the opaque M80442 or the vitreous LH244 parental kernels.
Figure 3:
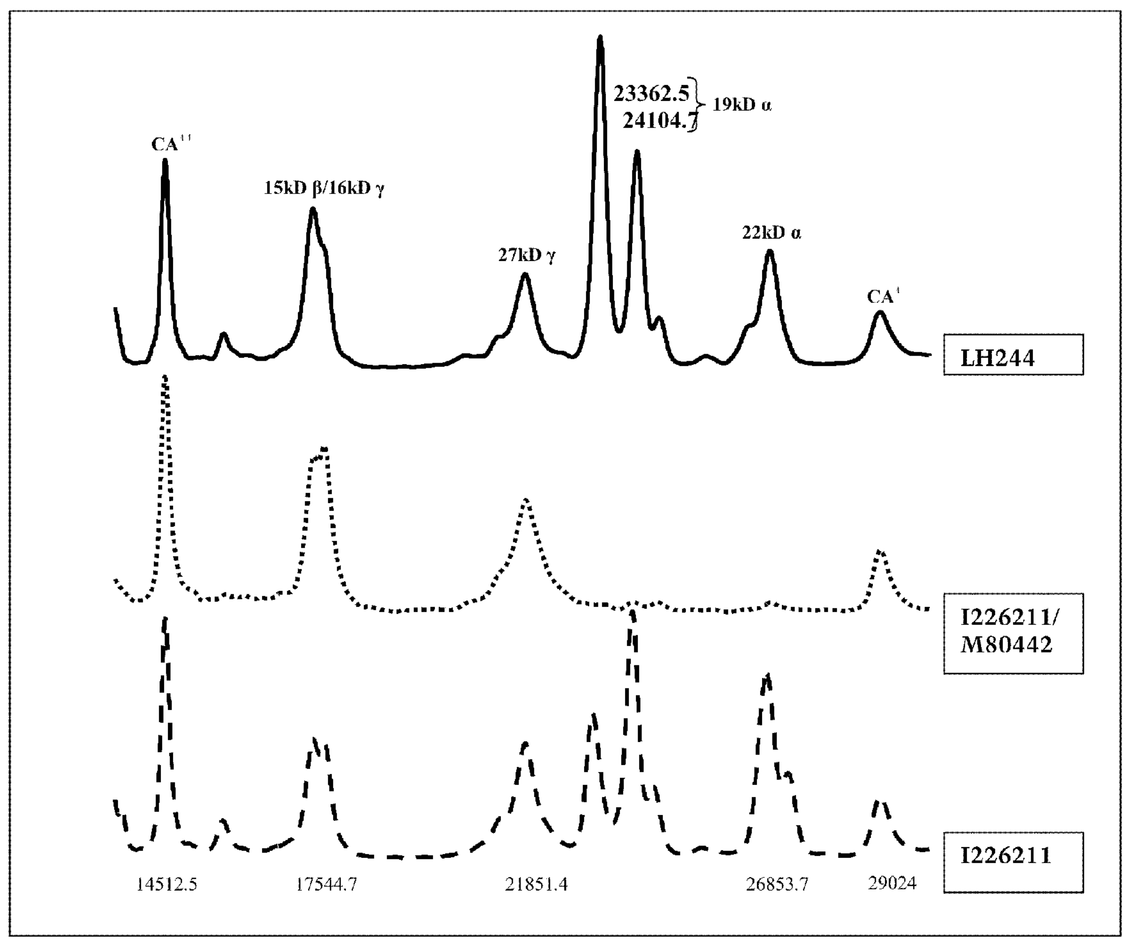
FIG. 3 illustrates the content of various seed and reference proteins in corn seed derived from various genetic backgrounds. MALDI-TOF MS traces from inbred line I226211 (dashed lines), inbred line LH244, and the F1 seed from a cross between I226211 and M80442 (I226211/M80442) showing the reduction in 19 kD and 22 kD zeins in the I226211/M80442 seed. The content of the 27 kDa gamma zein is not significantly increased in I226211/M80442 kernels relative to LH244 kernels. Peaks corresponding to maize zeins (15 kD beta, 16 kD gamma, 27 kD gamma, 19 kD alpha, and 22 kD alpha) and the reference peaks for carbonic anhydrase (CA++ and CA+) are indicated.

An "allele" refers to an alternative sequence at a particular locus; the length of an allele can be as small as one nucleotide base, but is typically larger. Allelic sequence can be amino acid sequence or nucleic acid sequence.

The term "construct" as used herein refers to any recombinant DNA molecule.

The term "control" means a reference seed or plant that of the same genotype as a transgenic seed or plant that is used to quantify a trait where the control lacks the recombinant DNA construct that provides the trait in the transgenic seed or plant. A control can be wild type or a negative segregant from a hemizygous transgenic parent.

As used herein, the phrase "a genetically distinct corn line" refers to any corn line that differs in at least one allele of at least one locus relative to a reference corn line. In the context of a cross, the genetically distinct corn line differs in at least one allele of at least one locus relative to the other parental line of the cross.

As used herein, the term "genetic element" refers to either a recombinant DNA construct (commonly referred to as a "transgene") that has been inserted into the maize genome or a genetic locus of the maize genome.

The phrase "a heterologous promoter", as used herein in the context of a DNA construct, refers to either: i) a promoter that is derived from a source distinct from the operably linked structural gene or ii) a promoter derived from the same source as the operably linked structural gene, where the promoter's sequence is modified from its original form.

The phrase "high stringency hybridization conditions" refers to nucleic acid hybridization conditions comprising a salt concentration of about 1×SSC, a detergent concentration of about 0.1% SDS, and a temperature of about 50° C., or equivalents thereof.

As used herein, the terms "linked" or "genetically linked", when used in the context of a genetic locus and a marker, refers to a genetic locus that is located less then 50 cM from the marker.

A "locus" is a short sequence that is usually unique and usually found at one particular location in the genome by a point of reference; e.g., a short DNA sequence that is a gene, or part of a gene or intergenic region. A locus of this invention can be a unique PCR product at a particular location in the genome. The loci of this invention comprise one or more polymorphisms; i.e., alternative alleles present in some individuals.

As used herein, a "marker" can be a detectable characteristic that can be used to discriminate between heritable differences between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics.

As used herein, "marker assay" means a method for detecting a polymorphism at a particular locus using a particular method, e.g. measurement of at least one phenotype (such as seed color, seed opacity, seed vitreousness, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, the term "mapping" refers to the process of using either genetic markers, molecular markers, or a combination of both to identify the position of a locus on a chromosome.

As used herein, the term "milling" refers to any method whereby a corn seed is ground, crushed, broken, sheared, fractured and/or disrupted. Milling can be performed under dry conditions, wet conditions, or under a combination of wet and dry conditions.

As used herein, a "molecular marker" refers to a polymorphic nucleic acid sequence or nucleic acid feature. A "polymorphism" is a variation among individuals in sequence, particularly in DNA sequence, or feature, such as a transcriptional profile or methylation pattern. Useful polymorphisms include single nucleotide polymorphisms (SNPs), insertions or deletions in DNA sequence (Indels), simple sequence repeats of DNA sequence (SSRs) a restriction fragment length polymorphism, a haplotype, and a tag SNP. A genetic marker, a gene, a DNA-derived sequence, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

As used herein, the phrase "opaque modifier" refers to a genetic locus that can restore the vitreous phenotype when combined with germplasm that produces opaque corn seed with reduced alpha-zein storage protein content. An opaque modifier that maps to one genetic locus can act either alone or in concert with additional opaque modifiers that map to distinct genetic loci to restore the vitreous phenotype to opaque corn seed with reduced alpha-zein storage protein content. Restoration of the vitreous phenotype to opaque corn seed with reduced alpha-zein storage protein content by the opaque modifier locus or opaque modifier loci can be either partial or complete.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter.

As used herein, "polymorphism" means the presence of one or more variations of a nucleic acid sequence at one or more loci in a population of one or more individuals.

As used herein, the phrases or terms "sequence identity" is used to describe sequence relationships between two or more nucleotide sequences. The percentage of "sequence identity" between two sequences is determined by comparing two optimally aligned sequences over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa. A first nucleotide sequence when observed in the 5' to 3' direction is said to be a "complement" of, or complementary to, a second or reference nucleotide sequence observed in the 3' to 5' direction if the first nucleotide sequence exhibits complete complementarity with the second or reference sequence. As used herein, nucleic acid sequence molecules are said to exhibit "complete complementarity" when every nucleotide of one of the sequences read 5' to 3' is complementary to every nucleotide of the other sequence when read 3' to 5'. A nucleotide sequence that is complementary to a reference nucleotide sequence will exhibit a sequence identical to the reverse complement sequence of the reference nucleotide sequence.

"Quantitative Trait Locus (QTL)" refers to a locus that controls to some degree traits that are usually continuously distributed and which can be represented quantitatively.

The term "regeneration" as used herein refers to any method of obtaining a whole plant from any one of a seed, a plant cell, a group of plant cells, plant callus tissue, or an excised piece of a plant.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

The term "transformation" as used herein refers to a process of introducing an exogenous DNA sequence (e.g., a vector, a recombinant DNA molecule) into a cell or protoplast in which that exogenous DNA is incorporated into a chromosome or is capable of autonomous replication.

The phrase "transgenic" refers to a seed or plant including progeny that contains a recombinant DNA construct.

As used herein, "typing" and "genotyping" refer to any method for determining the specific allelic form of a polymorphism.

The term "vector" as used herein refers to any recombinant polynucleotide construct that may be used for the purpose of transformation, i.e., the introduction of heterologous DNA into a host cell.

I. Seeds of the Invention

A. Transgenes that Provide for a Reduced Alpha-Zein Content

Transgenic seeds comprising recombinant DNA constructs that provide for reduced alpha-zein storage protein content are contemplated. The alpha-zein storage protein content in such transgenic seeds is reduced relative to control seed, e.g. reduced by at least 10%, more preferably by at least 50% of the alpha-zein content of a control seed. Recombinant DNA constructs for producing double-stranded RNA (dsRNA) are particularly contemplated for effecting zein reduction. Typically, such a DNA construct comprises as a minimum a promoter active in the tissue targeted for suppression, a transcribable that can form dsRNA and a transcription terminator element. A variety of different recombinant DNA sequences for producing one or more siRNAs that reduce expression of the 19 kD and/or 22 kD alpha-zein genes are contemplated by this invention. The recombinant DNA transgene sequence for producing a small interfering RNA (siRNA) may produce the siRNA either directly or may produce an RNA that results in the formation of an siRNA by the plant host. One non-limiting example of a sequence for producing an siRNA is described in U.S. Pat. No. 6,635,805, incorporated herein by reference in its entirety. U.S. Pat. No. 6,635,805 describes methods of silencing endogenous target plant genes with siRNA producing transgenes. These methods may employ transgenes comprising a promoter operably linked to DNA which can be transcribed in a plant cell. This RNA transcript in turn comprises an RNA plant virus sequence that can replicate in the cytoplasm of the plant cell. In general, the RNA transcript typically contains just those sequences required for its autonomous replication in the cytoplasm of the host cell. A key feature of the RNA transcript is the presence of at least one targeting sequence which causes post-transcriptional gene silencing of at least one target gene. This targeting sequence is foreign to the plant virus sequence, is 23 nucleotides or longer, and is at least 80% identical to the target sequence. In the case of this invention, the target sequence can be an 19 kD and 22 kD alpha-zein gene or a sequence that is at least 80% identical to the 19 kD and 22 kD alpha-zeins gene sequences.

Figure 6:
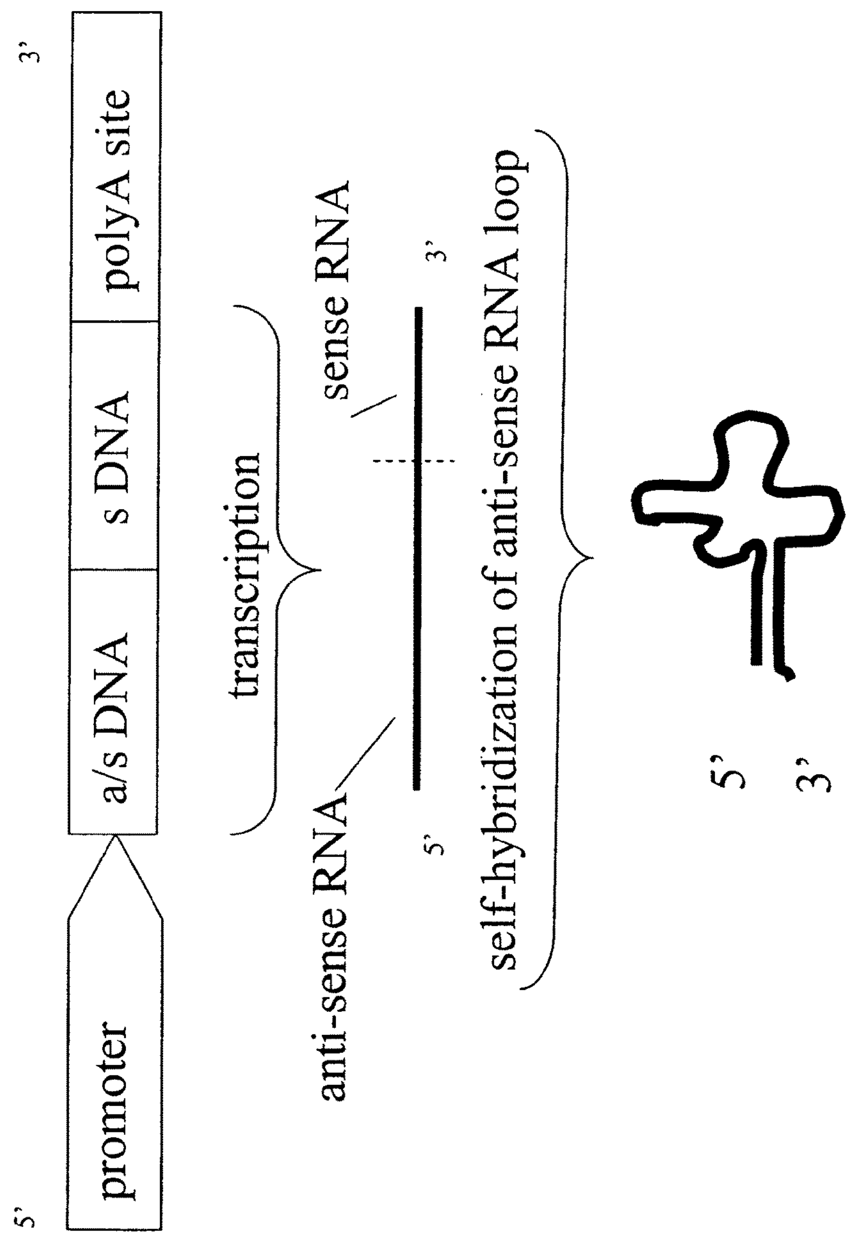
FIG. 6 illustrates a recombinant DNA construct useful in this invention to produce a double stranded RNA to reduce gene expression.

Other methods of producing siRNA directed against a target gene are also contemplated by this invention. For example, a transgene sequence for producing an siRNA may comprise a promoter that is operatively linked to an intron encoding sequence and a hairpin RNA derived from a sequence in the target gene (Miki and Shimamoto, Plant Cell Physiol. 2004 April; 45(4):490-495). Alternatively, a transgene sequence for producing an siRNA may comprise an RNA pol III promoter operably linked to a hairpin RNA (Lu et al., Nucleic Acids Res. 2004 December 2; 32(21):e171). The hairpin RNA may comprise a 5' sequence of roughly 19-24 nucleotides of sense strand target gene sequence followed by a spacer nucleotide of about 8-10 nucleotides followed by a sequence of roughly 19-24 nucleotides of antisense sequence that is capable of base pairing with the preceding sense strand sequence. However, it has also been demonstrated that transgene sequences for producing hairpin RNA-expressing plant transgenes containing sense/antisense arms ranging from 98 to 853 nucleotides can yield efficient reductions in endogenous gene expression in a wide range of plant species (Wesley et al., Plant J. 2001, 27(6):581-90). As illustrated in FIG. 6, an exemplary DNA construct is transcribed in the cell to produce RNA comprising an anti-sense oriented RNA segment and an RNA segment that is complementary to the 5'-most end of the anti-sense oriented RNA segment. The 5' and 3' ends of the anti-sense oriented RNA segment can self-hybridize to form a double-stranded RNA. Vectors and methods for effecting efficient inhibition of endogenous plant genes with transgene-mediated expression of hairpin RNAs are disclosed in U.S. Patent Application Nos. 2005/0164394, 2005/0160490, and 2004/0231016, each of which is incorporated herein by reference in their entirety.

Figure 7:
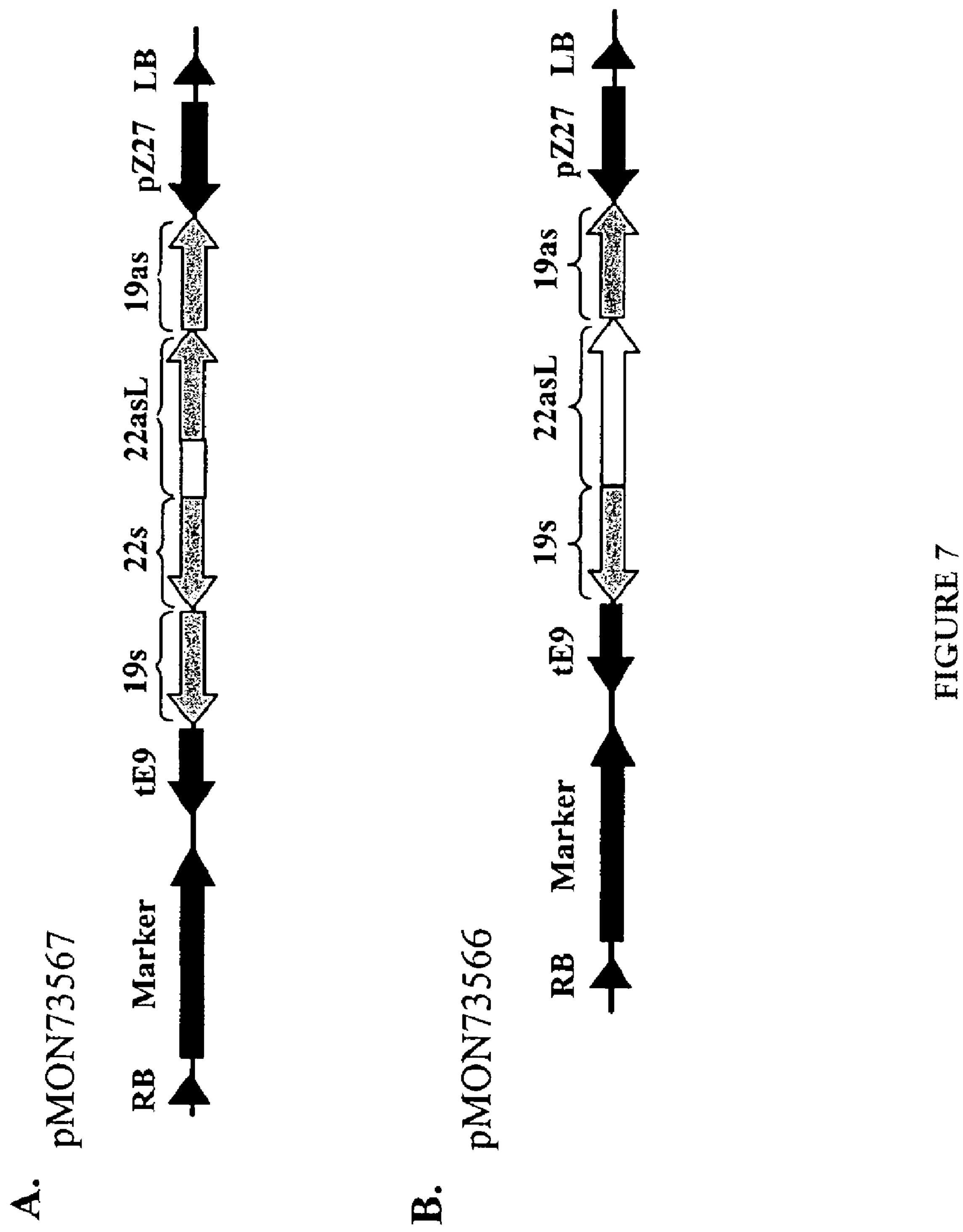
FIG. 7 illustrates the design of exemplary vector constructs pMON73567 and pMON73566 for reducing expression of both 19 kd and 22 kd zein genes in transgenic plants.

Recombinant DNA constructs can thus be useful in providing for suppression of the protein level of alpha-zeins, preferably of both the 19 kD and 22 kD alpha-zein proteins. There are numerous ways to suppress proteins that are expressed in a cell, e.g. including suppression of the gene encoding the protein by RNAi or by overexpression of a microRNA that has a recognition site on such gene. RNAi constructs can have a variety of arrangements of the DNA from the genes that encode 19 kD and 22 kD alpha-zeins, e.g. where sense and anti-sense DNA fragments from the genes are in the same or in separate recombinant DNA constructs. In one non-limiting embodiment the recombinant DNA construct comprises a promoter that is active in corn seed and is operably linked in 5' to 3' order to a segment from the anti-sense strand of the DNA coding for the 19 kD alpha-zein, a segment from the anti-sense strand of the DNA coding for the 22 kD alpha-zein, a segment from the sense strand of the DNA coding for the 22 kD alpha-zein which is shorter than the length of the preceding anti-sense strand and is complementary to the 5' most part of the preceding anti-sense strand and a segment from the sense strand of the DNA coding for the 19 kD alpha-zein having complementarity to the preceding 19 kD alpha-zein anti-sense strand, e.g. as disclosed in U.S. Patent Application Publication Number 2006/0075515 A1, incorporated herein by reference. Exemplary vectors that provide for reductions in expression of both the 19 kd and 22 kd zein genes are also shown in FIG. 7. In another non-limiting embodiment the recombinant DNA construct comprises a promoter that is active in corn seed and is operably linked in 5' to 3' order to DNA that is transcribed to a microRNA precursor having a recognition site in the gene for expressing the 19 kD alpha-zein and to a microRNA precursor having a recognition site in the gene for expressing the 22 kD alpha-zein; DNA for transcription to microRNA precursors are described in U.S. Patent Application Publication Number 2006/0200878 A1, incorporated herein by reference.

Alternatively, a recombinant DNA comprising a transgenes containing fragments of 19 kD and 22 kD alpha-zeins genes in either the sense or the antisense orientation that are operably linked to a plant promoter can provide for silencing of endogenous 19 kD and 22 kD alpha-zeins genes. Such methods for effecting the silencing of endogenous plant genes are disclosed in U.S. Pat. No. 5,231,020, incorporated herein by reference in its entirety. It is noted that the 19 kD and 22 kD alpha-zeins fragment need not have perfect identity to the endogenous 19 kD and 22 kD alpha-zeins genes to effect reductions in 19 kD and 22 kD alpha-zeins gene expression. In this regard, the 19 kD and 22 kD alpha-zeins fragment in the transgene will typically have at least 80% sequence identity to the endogenous 19 kD and 22 kD alpha-zeins genes. However, 19 kD and 22 kD alpha-zeins transgene fragments with 90% or greater percent identity to the endogenous 19 kD and 22 kD alpha-zeins genes are preferred. Although antisense or sense fragments of 19 kD and 22 kD alpha-zeins genes as small as 23 base pairs can be used in such constructs, 19 kD and 22 kD alpha-zeins sense or antisense fragments of 100 base pairs or more are preferred, and 19 kD and 22 kD alpha-zeins sense or antisense constructs with more than 500 base pairs are most preferred. However, sense strand fragments used in the silencing constructs would be designed such that they are incapable of producing functional 19 kD and 22 kD alpha-zeins proteins. This can be accomplished by any number of strategies such as placing the sense strand fragment out of frame with any translation initiation codons in the primary transcript of the 19 kD and 22 kD alpha-zeins transgene, using fragments of the 19 kD and 22 kD alpha-zeins transgene that lack key functional domains, and/or incorporating translational stop codons in the 19 kD and 22 kD alpha-zeins sequences. Without being limited by theory, it is further understood that the mechanism by which the transgene fragment may reduce expression of the endogenous 19 kD and 22 kD alpha-zeins genes can be by any one of a transcriptional gene silencing mechanism, a post-transcriptional silencing mechanism, a mechanism involving small interfering RNA molecule production, and/or a mechanism involving RNA-directed DNA methylation.

The use of DNA constructs that inhibit only one of the alpha-zein proteins are also useful. DNA constructs that provide for suppression of only the 19 kD alpha-zein are described in U.S. Patent Application Publication Number 2006/0075515 A1.

A variety of promoters can be used in the recombinant DNA constructs for suppressing expression of the alpha-zein genes. One broad class of useful promoters is referred to as “constitutive” promoters in that they are active in most plant organs throughout plant development. For example, a constitutive promoter can be the rice actin 1 promoter as disclosed in U.S. Pat. No. 5,641,876, incorporated herein by reference, or a viral promoter such as the well-known CaMV35S or FMV35S promoters.

Promoters that are active in seed tissues can also be used in recombinant DNA constructs to effect zein reduction. Exemplary seed tissue promoters are derived from seed genes such as napin (U.S. Pat. No. 5,420,034), maize L3 oleosin (U.S. Pat. No. 6,433,252), zein Z27 (Russell et al., (1997) Transgenic Res. 6(2):157-166), globulin 1 (Belanger et al., (1991) Genetics 129:863-872), glutelin 1 (Russell (1997) supra), and peroxiredoxin antioxidant (Perl) (Stacy et al., (1996) Plant Mol Biol. 31(6):1205-1216).

An intron may also be operably linked to the promoter in the DNA expression construct. For monocot plant use, introns such as the maize Adh1 intron, the maize hsp70 intron (U.S. Pat. No. 5,424,412) or the rice Act1 intron (McElroy et al., 1990, The Plant Cell, Vol. 2, 163-171) can be used. This group of exemplary introns is non-limiting and one skilled in the art could employ other introns that are not explicitly cited here in the practice of this invention.

A recombinant DNA construct for producing transcribed RNA in a plant cell are typically terminated at the 3' end by a non-translated region containing a polyadenylation signal. 3' elements include, but are not limited to, 3' elements from the genes within the host plant; *Agrobacterium tumefaciens* genes such as nos 3', tml 3', tmr 3', tms 3', ocs 3', tr7 3'; 3' elements from plant genes, such as wheat (*Triticum aesevitum*) heat shock protein 17 (Hsp 17 3'), a wheat ubiquitin gene, a wheat fructose-1,6-biphosphatase gene, a rice glutelin gene, a rice lactate dehydrogenase gene, and a rice beta-tubulin gene, and pea (*Pisum sativum*) ribulose biphosphate carboxylase gene (rbs 3').

Numerous methods for transforming plant cells with recombinant DNA and generating fertile transgenic plants are known in the art and may be used in the present invention. Two commonly used methods for plant transformation are Agrobacterium-mediated transformation and microprojectile bombardment. Microprojectile bombardment methods are illustrated in U.S. Pat. Nos. 5,550,318; 5,538,880; 6,160,208; and 6,399,861; *Agrobacterium*-mediated methods are disclosed in U.S. Pat. No. 5,591,616; and methods for transformation mediated by bacteria other than *Agrobacterium* is disclosed in U.S. Patent Application Publication Number 2007/0271627 A1, all of which are incorporated herein by reference for methods of generating fertile transgenic corn plants and progeny seed.

The seeds of transgenic plants can be harvested from fertile transgenic plants and be used to grow progeny generations of transformed plants of this invention including hybrid plants line for screening of plants having reduced alpha-zein. In addition to direct transformation of a plant with a recombinant DNA, transgenic plants can be prepared by crossing a first plant having a recombinant DNA with a second plant lacking the recombinant DNA. For example, a recombinant DNA construct can be introduced into first plant line that is amenable to transformation to produce a transgenic plant that can be crossed with a second plant line to introgress the recombinant DNA into the second plant line. A transgenic plant with recombinant DNA providing reduced alpha-zein can be crossed with transgenic plant line having other recombinant DNA that confers another trait, e.g. herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the recombinant DNA for both parental traits and some will carry recombinant DNA for one parental trait; such plants can be identified by markers associated with parental recombinant DNA. Progeny plants carrying recombinant DNA for both parental traits can be crossed back into the female parent line multiple times, e.g. usually 6 to 8 generations, to produce a progeny plant with substantially the same genotype as one original transgenic parental line but for the recombinant DNA of the other transgenic parental line.

In the practice of transformation DNA is typically introduced into only a small percentage of target cells in any one transformation experiment. Marker genes are used to provide an efficient system for identification of those cells that are stably transformed by receiving and integrating a recombinant DNA construct into their genomes. Preferred marker genes comprise selective markers that confer resistance to a selective agent, such as an antibiotic or herbicide. Examples of such selectable markers are illustrated in U.S. Pat. Nos. 5,550,318; 5,633,435; 5,780,708, and 6,118,047, incorporated herein by reference.

The regenerated transformed plant or its progeny seed or plants can be tested for expression of the recombinant DNA and screened for the presence of enhanced agronomic trait. In this instance such testing can comprise screening the transgenic progeny seed for an opaque phenotype and/or screening for the seed for reductions in the alpha-zein storage protein content.

B. Genetic Loci that Provide for Reduced Alpha-Zein Content

Seeds of the instant invention can also comprise genetic loci that provide for reduced levels of one or more alpha-zein storage proteins. The alpha-zein storage protein content in seeds comprising the genetic loci is reduced relative to seed of the same variety that do not contain the genetic loci. Genetic loci that provide for reduced alpha-zein content include, but are not limited to, certain alleles of Defective endosperm-B30 (De-B30) locus, a Mucronate locus (Mc), a floury 2 locus, a floury 3 locus, an opaque 2 locus, or an opaque 7 locus. In instances where the allele of the locus conferring reduced alpha-zein storage content is recessive, it is understood that the maize plant that produces the seed with reduced alpha-zein content is homozygous for that recessive mutation. Recessive alleles of the opaque 2 locus that provide for reduced alpha-zein content would be in the homozygous state. In instances where the allele is dominant or semi-dominant, the dominant or semi dominant allele may be present in either a homozygous or heterozygous state. Thus, semi-dominant or dominant alleles of the floury 2 locus, Defective endosperm-B30 (De-B30) locus, a Mucronate locus (Mc), that provide for reduced alpha-zein content could be in the homozygous state or heterozygous state. The floury 2 locus, the Defective endosperm-B30 (De-B30) locus, and the Mucronate locus (Mc) are described in Marocco et al., The Plant Cell, Vol. 3, 507-515, 1991 and references cited therein). The zygosity of the mutations could be ascertained by phenotypic assays for seed opacity when the locus that provides for reduced levels of one or more alpha-zein storage proteins is not in the presence of a genetically distinct modifier locus that provides a vitreous phenotype. When the locus that provides for reduced levels of one or more alpha-zein storage proteins is in the presence of a genetically distinct modifier locus that provides a vitreous phenotype, zygosity could be determined by a molecular marker assay when the polymorphism responsible for the reduced alpha-zein content is known. For example, alleles of the floury 2 and opaque 2 locus have been characterized at a molecular level and could be characterized by any suitable molecular marker assay that would reveal both wild type and mutant alleles of these loci (Coleman et al. Proc Natl Acad Sci, USA 92:6828-6831, 1995; Aukerman, M J and Schmidt, R J Plant Mol Biol 21:355-362; 1993).

C. Opaque Modifier Loci that Impart a Vitreous Kernel Phenotype on Seeds with Reduced Alpha-Zein Content This invention further provides opaque modifier loci that can restore a vitreous phenotype to opaque corn seed that comprise either recombinant DNA or other genetic loci that provide for reduced alpha-zein storage protein content. In certain embodiments of the invention, a single genetic locus referred to herein as an opaque modifier can restore the vitreous phenotype to opaque corn seed with reduced alpha-zein storage protein content. In other embodiments of the invention, more than one genetic loci referred to herein as opaque modifiers act in concert to restore the vitreous phenotype on corn seed with reduced alpha-zein storage protein content. In the latter instance, the number of discrete genetic loci that restore the vitreous phenotype can be up to about 100. In certain embodiments, the number of opaque modifier loci that restore the vitreous phenotype is up to about 10. In other embodiments, the number of opaque modifier loci is between 2 and 5.

An opaque modifier locus or opaque modifier loci of the invention can be obtained from a variety of corn germplasm sources including, but not limited to, hybrids, inbreds, partial inbreds, or members of defined or undefined populations. Germplasm characterized by a high kernel density is one useful source of the opaque modifier loci. Germplasm characterized by a seed density of at least about 1.24 grams/milliliter is considered to have a high kernel density.

Certain corn inbred lines have also been shown to contain one or more opaque modifier loci that act either alone or in combination to restore a vitreous phenotype on opaque seed reduced alpha-zein storage protein content.

One inbred corn line that is a source of opaque modifier locus or opaque modifier loci of the invention is described herein as "I226211". The inbred line corn variety I226211 has been described in U.S. Pat. No. 7,232,945. The seed of inbred Corn Variety I226211 was deposited with the American Type Culture Collection (ATCC; P.O. Box 1549, Manassas, Va., USA 20108) under ATCC Accession No. PTA-8214 on Feb. 21, 2007. The inbred line corn variety I226211 was also described as "mon020" in U.S. Provisional Application Ser. No. 61/041,035 filed Mar. 31, 2008 and in U.S. Provisional Application Ser. No. 61/072,633, filed Apr. 1, 2008. It is further contemplated that gernplasm used to construct I226211 also contain opaque modifier loci. It is also contemplated that molecular genetic analysis of mon0020 and other inbred corn lines could reveal genetic similarities and thus identify additional inbred corn lines that contain opaque modifier loci.

Another inbred corn line that is a source of opaque modifier locus or opaque modifier loci of the invention is described herein as "I283669". The inbred corn variety I283669 has been described in U.S. Pat. No. 7,414,181. The seed of inbred Corn Variety I283669 was deposited with the American Type Culture Collection (ATCC; P.O. Box 1549, Manassas, Va., USA 20108) under ATCC Accession No. PTA-8569 on Aug.

7, 2007. The inbred line corn variety I283669 was also described as "mon018" in U.S. Provisional Application Ser. No. 61/041,035 filed Mar. 31, 2008 and in U.S. Provisional Application Ser. No. 61/072,633, filed Apr. 1, 2008. It is further contemplated that germplasm used to construct I283669 also contain opaque modifier loci of the invention. It is also contemplated that molecular genetic analysis of I283669 and other inbred corn lines could reveal genetic similarities and thus identify additional inbred corn lines that contain opaque modifier loci.

In certain embodiments of the invention, the opaque modifier loci provided herein exhibit the unique and measurable property of providing a vitreous kernel phenotype to seed with reduced alpha-zein content in the absence of any significant increase in kernel 27 kD gamma zein content. In general, the 27 kD gamma zein storage protein content in corn seed comprising a genetic element that reduces alpha-zein content and the unique opaque modifiers of this invention is less than 2-fold higher than that of seed of the same variety that contain the genetic element but lack the opaque modifier. This property distinguishes the opaque modifier loci of this invention from previously disclosed opaque modifiers that result in significantly increased 27 kD gamma zein content (Geetha et al. The Plant Cell, Vol. 3, 1207-1219, 1991; Lopes and Larkins, Crop Sci 31, 1655-1662, 1991; Plant Physiol. (1990) 92, 191-196). In general, the gamma zein 27 kD gamma zein storage protein content in corn seed comprising a genetic element that reduces alpha-zein content and the previously disclosed opaque modifiers is typically 2- to 4-fold higher than that of seed of the same variety that contain the genetic element but lack the opaque modifier.

It is thus understood that certain embodiments of the invention comprise vitreous seed with decreased alpha-zein content that do not contain any opaque modifiers that result in a significant increase in 27 kD gamma zein content. In this context, it is understood that a significant increase in gamma zein content is an increase of 2- to 4-fold higher than that of seed of the same variety that contain a genetic element that reduces seed alpha-zein content but lack the opaque modifier. Thus, in certain embodiments of this invention, the opaque modifiers that do not provide for a significant increase in gamma zein content are opaque modifiers wherein the seed gamma zein content is less than 2-fold higher than that of seed of the same variety that contain the genetic element but lack the opaque modifier. In still other embodiments, the opaque modifiers of the instant invention provide seed wherein the seed gamma zein content is less than 1.8-, 1.5-, 1.2-, or 1.1-fold higher than that of seed of the same variety that contain the genetic element but lack the opaque modifier. Opaque modifiers that result in a significant increase in 27 kD gamma zein content include, but are not limited to, opaque modifiers identified in Pool 15, Pool 17, Pool 18, Pool 23, Pool 24, Pool 25, Pool 26, Pool 27, Pool 29, Pool 31, Pool 32, Pool 33 or Pool 34 QPM (Quality Protein Maize) germplasm described by the International Maize and Wheat Improvement Centre (CIMMYT) in Mexico. In embodiments of this invention the vitreous seed with reduced alpha-zein content do not contain any of the opaque modifier loci that result in a significant increase in 27 kD gamma zein content, e.g. such as an opaque modifier locus that is mapped on the long arm of chromosome 7 near the centromere proximal locus encoding the 27 kD gamma zein or that is mapped on the long arm of chromosome 7 near the telomere proximal locus as disclosed by Lopes, M. A. et al. Mol. Gen. Genet. 247, 603-613, 1995.

Corn germplasm that can be used as a source of the opaque modifier loci useful in the invention can be identified by use of molecular markers. More specifically, opaque modifier loci identified in corn germplasm I283669 that are linked to molecular markers identified in Table 3 can be identified by determining if a corn germplasm comprises an allele of the marker that is associated with the linked opaque modifier locus. In Table 3 the alleles of the molecular markers that are associated with linked opaque modifier loci are more specifically identified by a DNA sequence and the position on that sequence of an identified polymorphism. Corn germplasm comprising the markers identified in Table 3 are thus additional identified sources of the genetic modifier loci of the invention.

Corn germplasm that can be used as a source of the opaque modifier loci useful in the invention can be identified by use of molecular markers. More specifically, opaque modifier loci identified in corn germplasm I226211 that are linked to molecular markers identified in Table 4 can be identified by determining if a corn gernplasm comprises an allele of the marker that is associated with the linked opaque modifier locus. In Table 4 the alleles of the molecular markers that are associated with linked opaque modifier loci are more specifically identified by a DNA sequence and the position on that sequence of an identified polymorphism. Corn germplasm comprising the markers identified in Table 4 are thus additional identified sources of the genetic modifier loci of the invention.

It is further contemplated that the opaque modifier loci that restore the vitreous phenotype to opaque seeds and that are linked to molecular markers identified in Tables 3 and 4 can be separated from other loci present in the source germplasm that do not contribute to restoration of the vitreous phenotype. Separation of the opaque modifier loci from other undesired loci can be accomplished by molecular breeding techniques whereby additional markers to the undesired genetic regions derived from the source germplasm are used. It is thus contemplated that seed comprising one or more opaque modifier loci of the invention can comprise just the locus or loci, or can comprise the locus or loci and an associated molecular marker. Given that the opaque modifier loci of the invention can be identified in a variety of different germplasms by the molecular markers provided herein, it is thus understood that the essential element is the opaque modifier loci itself rather than the specific source from which it was obtained.

D. Composition of Seeds

In one embodiment, the vitreous seeds of this invention have recombinant DNA that imparts a reduction in alpha-zein storage protein content as compared to control seed, and at least one opaque modifier locus that imparts the vitreous kernel phenotype, i.e. restores kernel hardness to seed with reduced alpha-zeins. In another embodiment, the vitreous seeds of the invention have at least one genetic element that imparts a reduced alpha-zein storage protein content and the seeds do not display significantly increased content of the 27 kD gamma zein storage protein.

The degree of alpha-zein reduction obtained can be controlled by using genetic elements that are either genetic loci or recombinant DNA that effect different levels of alpha-zein protein reductions. In certain embodiments of the invention, the content of an alpha-zein is reduced in the vitreous seeds to less than 20%, less than 10%, less than 5%, or less than 1% of the total seed protein by weight. In still other embodiments of the invention, the content of alpha-zeins is reduced in the vitreous seeds to less than 0.5%, less than 0.2%, or less than 0.1% of the total seed protein by weight. In still other embodiments, the content of an alpha-zein is reduced in the vitreous seeds containing the genetic element that reduces alpha-zein content to less than 10%, less than 5%, less than 1%, less than 0.5%, less than 0.2%, or less than 0.1% of an alpha-zein seed storage protein content of seed of the same variety that does not contain the genetic element.

It is further understood that the content of either a single alpha-zein or multiple alpha-zeins can be reduced in the vitreous seeds of the invention. In one embodiment either the 19 kD or the 22 kD alpha-zein storage protein content is reduced. In another embodiment both the 19 kD and the 22 kD alpha-zein storage protein content is reduced. FIG. 7 is an illustration showing constructs pMON73567 and pMON73566 useful for reducing both 19 kD and 22 kD zeins in transgenic plants harboring these constructs. pMON73567 contains dsRNA against both 19 kD and 22 kD alpha-zein sequences. pMON73566 contains dsRNA against only a 19 kD alpha-zein sequence and which uses the 22 kD alpha-zein sequence as the loop.

Since alpha-zeins contain relatively low levels of certain amino acids such as lysine and tryptophan and relatively high levels of other amino acids such a leucine, a reduction in alpha-zein shifts adjusts the amino acid content of seed to higher levels of lysine and tryptophan and lower levels of leucine, as illustrated in Table 1.

The gamma zein storage protein content in vitreous seeds of the invention are not measurably increased relative to a parental corn plant seed with an opaque kernel phenotype and a reduced alpha-zein storage protein content. In certain embodiments the gamma zein storage protein content in vitreous seeds of the invention are not increased by a measure of more than 1% relative to a parental corn plant seed with an opaque kernel phenotype and a reduced alpha-zein storage protein content. In other embodiments the measurable increase in gamma zein content, if any, is less than 50%, 25%, 10%, or 5% relative to a parental corn plant seed. In still other embodiments, the gamma zein storage protein content in vitreous seeds of the instant invention are essentially equivalent to the gamma zein storage protein content in a parental corn plant seed with an opaque kernel phenotype and a reduced alpha-zein storage protein content.

The vitreous corn seed of the invention with reduced alpha-zein storage protein content and do not display significantly increased content of the 27 kD gamma zein storage protein can have a kernel density of at least about 1.24 grams/milliliter. In other embodiments, the vitreous of the invention can have a kernel density of at least 1.25, 1.26, 1.27, 1.28 or 1.29 grams per milliliter. In certain embodiments of the invention, the upper limit of the kernel density is not more than the kernel density of a parental line, where the parental line comprises one or more opaque modifier loci and does not contain loci and/or transgenes that decrease alpha-zein storage protein content. In such embodimenty where the upper limit of kernel density is not more than the kernel density of a parental line, the kernel density is not more than about 1.36 grams per milliliter. In still other embodiments, the kernel density is not more than about 1.35, 1.34, 1.33, 1.32, 1.31, or 1.30 grams per milliliter.

It is further contemplated that the content of alpha-zein proteins, 27 kD gamma zein protein, lysine, leucine and tryptophan in the vitreous seeds of the invention will be directly reflected in the content of such components in a meal obtained by grinding, macerating or otherwise disrupting the seeds of the invention. It also contemplated that the content of alpha-zein proteins, 27 kD gamma zein protein, lysine, leucine and tryptophan in the vitreous seeds of the invention will be reflected in the content of such components in a feed, a meal, or partially purified protein composition obtained by grinding, macerating and/or processing the vitreous seeds of the invention.

II. Methods for Obtaining Seed Comprising a Vitreous Kernel Phenotype and a Reduced Alpha-Zein Storage Protein Content Methods of obtaining seed comprising a vitreous kernel phenotype and a reduced alpha-zein storage protein content that use transgenes that reduce alpha-zein-storage protein content and impart an opaque phenotype are contemplated by this invention. One advantage of this method, is that the transgenes confer a dominant opaque phenotype as opposed to the recessive opaque phenotype conferred by certain alleles of the opaque 2 locus (o2) that were previously used to identify opaque modifiers other than those of this invention. Use of the dominant transgene permits opaque modifiers to be identified by visual screening for in the F1 generation rather than having to use an F2 or later generation as is necessary when using recessive opaque-2 mutants. Consequently, it is possible to more quickly screen a wider assortment of germplasms for the desirable opaque modifiers by using dominant transgenes as per the methods of the instant invention. Second, opaque modifiers that are dependant on a wild-type allele of the Opaque-2 transcription factor can be identified by using the dominant transgene rather than the recessive opaque-2 mutants. Any opaque modifier that operates through a wild-type Opaque-2 allele would not be identified in methods comprising use of recessive opaque-2 mutants. Finally, the methods of the instant invention also permit recovery of novel opaque modifiers loci that do not result in an increase in the content of the 27 kD gamma zein storage protein in the vitreous seed of the invention.

In practicing the methods of the invention, a corn line comprising recombinant DNA that reduces the alpha-zein storage content is typically crossed to a genetically distinct corn line. The genetically distinct corn line can be obtained from a variety of sources including, but not limited to, hybrids, inbreds, partial inbreds, or members of defined or undefined populations. Germplasm characterized by a high kernel density is one source of the genetically distinct lines that can be used in the methods. Germplasm characterized by a seed density of at least about 1.24 grams/milliliter is considered to have a high kernel density. It is understood that the corn line comprising the transgene and the genetically distinct corn line can each be used as either pollen donors or pollen recipients in the methods of the invention.

In certain instances, the genetically distinct corn line can differ from the corn line comprising the transgene in a subset of loci, especially when those loci comprise any of the opaque modifier loci identified herein. In particular, the use of genetically distinct corn lines comprising one or more loci selected from those that are linked to the molecular markers disclosed herein are specifically contemplated. In certain embodiments, those loci can comprise an allele of the loci present in I283669 germplasm, I226211 germplasm or combinations thereof. In other embodiments, the markers can comprise an allele of the markers present in I283669 germplasm, I226211 germplasm or combinations thereof. The use of markers described in Tables 3 and 4 are useful for identifying or obtaining genetically distinct corn lines for use in the methods of this invention.

Once progeny of the cross between a corn line comprising an opaque kernel phenotype and recombinant DNA that reduces expression of an alpha-zein storage protein with a genetically distinct corn line are obtained, a seed comprising a vitreous kernel phenotype and the transgene that confers on seed a reduced alpha-zein storage protein content is selected. Selection of such seed can be accomplished in a variety of ways. The vitreous phenotype can usually be selected by visual screening. Such visual screening can be facilitated by placing the seed of the cross on a light source. Vitreous seed typically transmit more light than opaque seed and are readily identified. However, selection for the vitreous phenotype could also be accomplished by other methods that include, but are not limited to, selection of seed for increased density. Density can be determined by a variety of methods that include but are not limited to, Near Infrared Transmittance (NIT). It is further contemplated that either manual, semi-automated, or fully automated methods where vitreous seed are screened and selected on the basis of density, light transmittance, or other physical characteristics are also contemplated herein.

With respect to selecting for seed that comprise a transgene that comprises a reduced alpha-zein content, any method that provides for either semi-quantitative or quantitative analysis of the alpha-zeins can be used. Such methods include but are not limited to methods based on a chromatographic assay, an immunoassay, an electrophoretic assay, a mass spectrometric assay, a protein staining assay, or any assay that is combination of the foregoing assays.

It is further contemplated that the crosses and/or selection of the transgene(s) conferring reduced alpha-zein content to the genetically distinct lines containing the opaque modifiers can be facilitated by linkage of a selectable marker that confers resistance to a herbicide. For example, in crosses of corn plants that are heterozygous for the transgene with plants that are either homozygous or heterozygous for the allele(s) conferring the vitreous kernal phenotype, F1 progeny that are heterozygous for the transgene can be selected by herbicide treatment. Also, F2 plants derived from F1 plants that are heterozygous for the transgene can be enriched for F2 corn plants that are homozygous for said transgene by subjecting said plurality of F2 plants to herbicide selection for the transgene. Molecular markers that can distinguish corn plants that are either heterozygous or homozygous for the transgene that provides for reduced alpha-zein storage protein content can also be used to identify corn plants that are homozygous for the transgene insertion. The selectable marker gene can be a gene encoding a neomycin phosphotransferase protein, a phosphinothricin acetyltransferase protein, a glyphosate resistant 5-enol-pyruvylshikimate-3-phosphate synthase (EPSPS) protein, a hygromycin phosphotransferase protein, a dihydropteroate synthase protein, a sulfonylurea insensitive acetolactate synthase protein, an atrazine insensitive Q protein, a nitrilase protein capable of degrading bromoxynil, a dehalogenase protein capable of degrading dalapon, a 2,4-dichlorophenoxyacetate monoxygenase protein, a methotrexate insensitive dihydrofolate reductase protein, and an aminoethylcysteine insensitive octopine synthase protein. The corresponding selective agents used in conjunction with each gene can be: neomycin (for neomycin phosphotransferase protein selection), phosphinotricin (for phosphinothricin acetyltransferase protein selection), glyphosate (for glyphosate resistant 5-enol-pyruvylshikimate-3-phosphate synthase (EPSPS) protein selection), hygromycin (for hygromycin phosphotransferase protein selection), sulfadiazine (for a dihydropteroate synthase protein selection), chlorsulfuron (for a sulfonylurea insensitive acetolactate synthase protein selection), atrazine (for an atrazine insensitive Q protein selection), bromoxinyl (for a nitrilase protein selection), dalapon (for a dehalogenase protein selection), 2,4-dichlorophenoxyacetic acid (for a 2,4-dichlorophenoxyacetate monoxygenase protein selection), methotrexate (for a methotrexate insensitive dihydrofolate reductase protein selection), or aminoethylcysteine (for an aminoethylcysteine insensitive octopine synthase protein selection).

It is further contemplated that the crosses and/or selection of the transgene(s) conferring reduced alpha-zein content to the genetically distinct lines containing the opaque modifiers can be facilitated by linkage of a scoreable marker. Scoreable markers include but are not limited to antibiotic resistance genes, reporter genes, and any molecular marker that can be used to assay for the presence of the transgene that provides for reduced alpha-zein storage protein content. Scoreable marker genes include, but are not limited to, a gene encoding a beta-glucuronidase protein, a green fluorescent protein, a yellow fluorescent protein, a red fluorescent protein, a beta-galactosidase protein, a luciferase protein derived from a luc gene, a luciferase protein derived from a lux gene, a sialidase protein, streptomycin phosphotransferase protein, a nopaline synthase protein, an octopine synthase protein or a chloramphenicol acetyl transferase protein.

III. Methods of Identifying an Opaque Modifier Locus

The invention further provides methods of identifying opaque modifier loci that restore a vitreous phenotype to corn seed with an opaque phenotype and reduced alpha-zein storage protein content. These methods take advantage of the dominant opaque kernel phenotype conferred by transgenes that reduce alpha-zein storage protein content in seed. In general, the initial crossing and selection steps of the method for identifying the opaque modifier loci and materials used are essentially the same as those used in the previously described methods for obtaining the vitreous seed with a reduced alpha-zein storage protein content. However, the method of identifying the opaque modifier loci entails the additional step of genetically mapping the modifier locus.

The opaque modifier locus can be mapped by using either genetic markers, molecular markers, or a combination of both to identify the position of a locus on a chromosome. Genetic mapping is the process of determining the position of a gene relative to other genes and genetic markers through linkage analysis. The basic principle for linkage mapping is that the closer together two genes are on the chromosome, the more likely they are to be inherited together. Briefly, a cross is generally made between two genetically compatible but divergent parents relative to traits under study. Genetic markers can then be used to follow the segregation of traits under study (i.e. opaque modifier loci that impart a vitreous phenotype) in the progeny from the cross, often a backcross (BC1), $F_2$, or recombinant inbred population. Backcrossing a corn line containing the opaque modifier locus to a corn line comprising a dominant transgene is advantageous as the progeny containing the opaque modifier can be readily identified by scoring progeny that contain the transgene for a vitreous kernel phenotype.

Coinheritance, or genetic linkage, of a particular opaque modifier locus and a marker suggests that they are physically close together on the chromosome. Linkage is determined by analyzing the pattern of inheritance of a gene and a marker in a cross. The unit of recombination is the centiMorgan (cM). Two markers are one centiMorgan apart if they recombine in meiosis once in every 100 opportunities that they have to do so. The centiMorgan is a genetic measure, not a physical one. Those markers located less then 50 cM from a second locus are said to be genetically linked, because they are not inherited independently of one another. Thus, the percent of recombination observed between the loci per generation will be less than 50%.

During meiosis, pairs of homologous chromosomes come together and exchange segments in a process called recombination. The further a marker is from a gene, the more chance there is that there will be recombination between the gene and the marker. In a linkage analysis, the coinheritance of a marker and a gene or trait are followed in a particular cross. The probability that their observed inheritance pattern could occur by chance alone, i.e., that they are completely unlinked, is calculated. The calculation is then repeated assuming a particular degree of linkage, and the ratio of the two probabilities (no linkage versus a specified degree of linkage) is determined. This ratio expresses the odds for (and against) that degree of linkage, and because the logarithm of the ratio is used, it is known as the logarithm of the odds, e.g. a LOD score. A LOD score equal to or greater than three, for example, is taken to confirm that gene and marker are linked. This represents 1000:1 odds that the two loci are linked. Calculation of linkage is greatly facilitated by use of statistical analysis employing programs.

The genetic linkage of marker molecules can be established by a gene mapping model such as, without limitation, the flanking marker model reported by Lander et al. (Lander et al., 1989 Genetics, 121:185-199), and the interval mapping, based on maximum likelihood methods described therein, and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, XXell University, Ithaca, N.Y.). Use of Qgene software is a particularly preferred approach.

In certain embodiments, a single opaque modifier locus can confer the vitreous phenotype and be mapped to a single location on a chromosome. In other embodiments, a plurality of opaque modifier loci that cooperate to confer the vitreous kernel phenotype can be mapped. In particular embodiments of the invention, the markers used can be located less than about 45, 35, 25, 15, 10, 5, 4, 3, 2, or 1 or less cM apart on a chromosome from the opaque modifier locus. In certain embodiments of the invention, the markers used can detect polymorphisms within the contributing opaque modifier loci themselves and are thus located at 0 cM respective to the opaque modifier loci.

IV. Marker Assisted Selection for Production of Vitreous Seeds with Decreased Alpha-Zein Content or Mapping of Qpaque Modifiers The invention provides genetic markers and methods for the introduction of one or more opaque modifier loci conferring a vitreous phenotype on corn seed kernels that display an opaque phenotype in the absence of the modifier loci.

Marker assisted introgression involves the transfer of a chromosome region defined by one or more markers from one germplasm to a second germplasm. The initial step in that process is the genetic localization of the opaque modifier loci as previously described.

When an opaque modifier locus that is a QTL (quantitative trait locus) has been localized in the vicinity of molecular markers, those markers can be used to select for improved values of the trait without the need for phenotypic analysis at each cycle of selection. Values that can be associated with the vitreous phenotype conferred by the opaque modifier include but are not limited to light transmittance measurements or density determinations. In marker-assisted breeding and marker-assisted selection, associations between the QTL and markers are established initially through genetic mapping analysis as described. In the same process, one determines which molecular marker alleles are linked to favorable QTL alleles. Subsequently, marker alleles associated with favorable QTL alleles are selected in the population. This procedure will improve the value of the opaque modifier trait provided that there is sufficiently close linkage between markers and QTLs. The degree of linkage required depends upon the number of generations of selection because, at each generation, there is opportunity for breakdown of the association through recombination.

The associations between specific marker alleles and favorable QTL alleles also can be used to predict what types of progeny may segregate from a given cross. This prediction may allow selection of appropriate parents to generation populations from which new combinations of favorable QTL alleles are assembled to produce a new inbred line. For example, if line A has marker alleles previously known to be associated with favorable QTL alleles at loci 1, 20 and 31, while line B has marker alleles associated with favorable effects at loci 15, 27 and 29, then a new line could be developed by crossing A×B and selecting progeny that have favorable alleles at all 6 QTL.

Molecular markers can also be used to accelerate introgression of the opaque modifier loci into new genetic backgrounds (i.e. into a diverse range of germplasm). Simple introgression involves crossing an opaque modifier line to an opaque line with reduced alpha-zein content and then backcrossing the hybrid repeatedly to the opaque line (recurrent) parent, while selecting for maintenance of the opaque modifier locus. Over multiple backcross generations, the genetic background of the original opaque modifier line is replaced gradually by the genetic background of the opaque line through recombination and segregation. This process can be accelerated by selection on molecular marker alleles that derive from the recurrent parent.

Alternatively, recombinant DNA that imparts an opaque phenotype and reduced alpha-zein content can be introgressed into an elite inbred genetic background that comprises one or more opaque modifiers. Simple introgression involves crossing a transgenic line to an elite inbred line with an opaque modifier and then backcrossing the hybrid repeatedly to the elite inbred line (recurrent) parent, while selecting for maintenance of the transgene and the opaque modifier locus (i.e. a vitreous phenotype in the presence of reduced alpha-zein content and/or a linked transgenic trait). Linkage of the transgene to a selectable or scoreable marker gene could, in certain embodiments, further facilitate introgression of the transgene into the elite inbred genetic background. Over multiple backcross generations, the genetic background of the original transgenic line is replaced gradually by the genetic background of the elite opaque line modifier line through recombination and segregation. This process can be accelerated by selection on molecular marker alleles that derive from the recurrent parent. In certain embodiments, the elite inbred lines used are I283669, I226211, or other elite inbred lines comprising at least one opaque modifier locus that is genetically linked to a marker selected from the group identified in either Table 3 or Table 4.

Exemplary modifier loci of the invention that can be introgressed into additional genetic backgrounds include loci that are genetically linked to markers identified in Table 3 and Table 4. In certain embodiments, the marker comprises an allele of a marker present in I283669 or I226211 germplasm. In particular embodiments of the invention, the markers used can be located less than about 45, 35, 25, 15, 10, 5, 4, 3, 2, or 1 or less cM apart on a chromosome from the opaque modifier locus. In certain embodiments of the invention, the markers used can detect polymorphisms within the contributing opaque modifier loci themselves and are thus located at 0 cM respective to the opaque modifier loci.

Still other methods of identifying markers linked to an opaque modifier locus comprise the previously disclosed steps of crossing a corn lines comprising an opaque kernel phenotype and a transgene that reduces expression of an alpha-zein storage protein with at least two genetically distinct corn lines and (b) selecting a seed harvested from said crossing which has both reduced zeins and vitreous phenotype. However, these methods can also further comprise the steps of (c) identifying from the genetically distinct corn lines one or more parental lines that provide a locus that restores a vitreous phenotype and one or more parental lines that fail to restore a vitreous phenotype, (d) genotyping said genetically distinct corn lines with a plurality of markers; and (e) subtracting any common markers present in both parental lines that restore a vitreous phenotype and parental lines that fail to restore a vitreous phenotype from the markers in said parental line or lines that provided a locus that restores a vitreous phenotype, thereby identifying one or more markers linked to a locus that restores a vitreous kernel phenotype to corn kernels with an opaque phenotype and reduced alpha-zein storage protein content. Those markers that are shared by both the genetically distinct lines that restore the vitreous phenotype to opaque seed and the genetically distinct lines that fail to restore the vitreous phenotype to opaque seeds are unlikely to be linked to the opaque modifier loci. However, those markers that are not shared by both the genetically distinct lines that restore the vitreous phenotype to opaque seed and the genetically distinct lines that fail to restore the vitreous phenotype to opaque seeds are more likely to be linked to the opaque modifier loci.

V. Molecular Markers Linked to Opaque Modifier Loci and Methods of Use

Nucleic acid analysis methods are known in the art and include, but are not limited to, PCR-based detection methods (for example, TaqMan assays), microarray methods, and nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; and 5,616,464, all of which are incorporated herein by reference in their entireties. Methods for simultaneous detection or typing of multiple SNPs are also well known in the art and include, but are not limited to, methods described in U.S. Patent Application Publication Number 2005/0089920. However, the compositions and methods of this invention can be used in conjunction with any polymorphism typing method to type polymorphisms in corn genomic DNA samples. These corn genomic DNA samples used include but are not limited to corn genomic DNA isolated directly from a corn plant, cloned corn genomic DNA isolated from a non-corn host organism, or amplified corn genomic DNA.

In a preferred method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' to 3' exonuclease activity cleaves the probe and separates the reporter dye from the quencher dye resulting in increased fluorescence of the reporter.

For the purpose of opaque modifier loci mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of opaque modifier loci, particularly in the case of haplotypes.

VI. Seeds, Feed, Meal, Protein and Products Comprising Seeds, Meal, Protein, and Amino Acids This invention also provides a container of over about 1000, more preferably about 20,000, and even more preferably about 40,000 seeds where over about 10%, more preferably about 25%, more preferably about 50%, and even more preferably about 75% or more preferably about 90% of the seeds are seeds derived from a plant of this invention.

This invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of this invention.

Any of the plants or parts thereof of this invention may be harvested and, optionally, processed to produce a feed, meal, protein, protein hydrosylate, amino acid or oil preparation. A particularly preferred plant part for this purpose is harvested seed, but other plant parts can be harvested and used for stover or silage. In one embodiment, the feed, meal, protein, protein hydrosylate, amino acid, or oil preparation obtained from the seed of the invention is formulated for ruminant animals. In another embodiment, the feed, meal, protein, protein hydrosylate, amino acid, or oil preparation obtained from the seed of the invention is formulated for monogastric animals. Processes for obtaining corn seed products from the corn seed of the invention are provided herein. Methods to produce feed, meal, protein, protein hydrosylate, amino acid and oil preparations are known in the art. See, for example, U.S. Pat. Nos. 4,716,218; 4,957,748; 5,100,679; 5,219,596; 5,410,021, 5,936,069; 6,005,076; 6,146,669; 6,156,227; and 6,433,146. The grain or meal of this invention may be blended with other grains or meals. In one embodiment, the meal produced from harvested grain of this invention or generated by a method of this invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

The corn protein(s), amino acids, protein hydrosylates and/or corn meal produced according to this invention can be used as is or combined with a variety of other ingredients. The specific ingredients included in a product will be determined according to the ultimate use of the product. Exemplary products include animal feed, raw material for chemical modification, biodegradable plastic, blended food product, edible oil, cooking oil, lubricant, biodiesel, snack food, cosmetics, and fermentation process raw material. Products incorporating the meal and/or proteins or protein products described herein also include, but are not limited to, fermentable mixtures, complete or partially complete swine, poultry, and cattle feeds, pet foods, aquaculture feeds, and human food products such as extruded snack foods, breads, as a food binding agent, food supplements, sport drinks, nutritional food bars, multi-vitamin supplements, diet drinks, and cereal foods.

The corn meal is optionally subjected to conventional methods of separating the starch and protein components. Such methods include, for example, dry milling, wet milling, high pressure pumping, or cryogenic processes. These and other suitable processes are disclosed in Watson and Ramstad, In: Corn: Chemistry and Technology, Ch. 11-12, Amer. Assoc. Cereal Chemist, Inc., St. Paul, Minn., 1987.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Use of RNA-Mediated Suppression in Event M80442 to Increase Essential Amino Acids Lysine and Tryptophan Transgenic plants with reductions in both the 19 kD and 22 kD zein storage proteins were obtained by *Agrobacterium*-mediated transformation using a binary vector, pMON73567, that allowed for integration of T-DNA for expressing an inverted repeat of fusion DNA fragments corresponding to the coding region of both 19 kD and 22 kD alpha-zein genes. The transgenic plants resulted in the reduction of both 19 kD and 22 kD alpha-zeins in seeds through RNA interference (RNAi). Details of pMON73567 construction and the characterizations of the transgenic plants are described in U.S. Patent Application Publication Number 2006/0075515 A1 and Huang et al., Plant Molecular Biology, 61: 525-535, 2006. The efficient suppression of both 19 kD and 22 kD alpha-zeins results in a significant increase in the essential amino acids lysine and tryptophan in corn lines with independent transgenic events designated as M80442 and M82186; see Table 1. A significant decrease in the content of the amino acid leucine is also observed. This decrease in leucine content is beneficial as excess leucine in corn seed can inhibit utilization of isoleucine and valine (Harper A E, et al. Physiol. Rev. 50: 428-558, 1970, Harper A E, et al. Arch. Biochem. Biophys 57: 1-12, 1955; May R C, et al. J. Nutr. 121: 293-301, 1991). The transgenic corn lines produced seed with soft opaque shells that were susceptible to breakage under normal conveying conditions.

TABLE 1

Total amino acid analysis of ground kernels.

| | | Zein suppression events | |
|---|---|---|---|
| Ave ± SD[a] | WT | M80442 | M82186 |
| Ala | 6687 ± 594 | 5862 ± 999 | 6458 ± 322 |
| Arg | 4342 ± 293 | **6665 ± 1203** | **7165 ± 655** |
| Asx | 5555 ± 377 | **10253 ± 2803** | **11143 ± 886** |
| Glx | 17788 ± 1623 | 16 860 ± 3617 | 18603 ± 1322 |
| Gly | 3400 ± 166 | **4973 ± 783** | **5290 ± 410** |
| His | 1498 ± 126 | **2305 ± 518** | **2470 ± 160** |
| Ile | 3265 ± 255 | 3373 ± 587 | 3578 ± 261 |
| Leu | 11265 ± 1074 | **7718 ± 1264** | **8270 ± 497** |
| Lys | 2438 ± 132 | **4533 ± 780** | **4800 ± 443** |
| Phe | 3760 ± 282 | 3288 ± 571 | 3455 ± 260 |
| Ser | 4067 ± 364 | 4355 ± 779 | 4785 ± 325 |
| Thr | 3062 ± 226 | 3783 ± 676 | **4130 ± 279** |
| Trp | 598 ± 48 | **940 ± 201** | **1040 ± 96** |
| Tyr | 3720 ± 307 | 3652 ± 624 | 4045 ± 270 |
| Val | 4710 ± 325 | 5977 ± 1030 | **6293 ± 483** |
| Sum | 76155 ± 5996 | 84535 ± 16220 | 91553 ± 6286 |
| Lys % (P)[b] | 2.83 ± 0.23 | **5.40 ± 0.37** | **5.33 ± 0.28** |
| Trp % (P)[b] | 0.69 ± 0.05 | **1.12 ± 0.11** | **1.15 ± 0.05** |
| Leu % (P)[b] | 13.00 ± 0.34 | **9.21 ± 0.56** | **9.20 ± 0.34** |

Samples were ground corn meal of bulked mature kernels from individual ears.

[a]Data (ppm) are averages of ears within an event ± standard deviations. Four homozygous ears from each event were analyzed and the data was averaged.

[b]Amino acid levels are expressed as the percent of protein measured without the subtraction of moisture.

The numbers in bold are statistically different from the wild-type (WT) numbers by Dunnett's test ($\alpha = 0.05$).

Asx, asparagine and aspartate;

Glx, glutamine and glutamate.

Example 2

Visual Identification of Modifiers of Opaque Kernel Phenotype in Zein Suppression Event M80442

A corn line with zein suppression event M80442 of Example 1 was used as a pollen donor for hand crosses with twenty-four genetically distinct maize lines with a range of kernel density from 1.292 to 1.361 grams/milliliter. For each of the twenty-four maize lines, at least ten ears were pollinated for each cross. Plants or each of the 24 lines is self pollinated for use as controls. Ears are harvested at approximately fifty-five days after pollination and dried for one week at 35 degrees Celsius. The ears are shelled and kernels visually inspected on a light box for opacity (FIG. 1). Of all F1 kernels inspected, only kernels from the progeny of crosses between (I283669×M80442) and (I226211×M80442) were found to be vitreous. As expected, all kernels obtained by self-pollination of the twenty-four pollen recipient lines tested were vitreous and all kernels obtained by self pollination of M80442 pollen donor plants were opaque.

Example 3

Density Measurements of Kernels from Crosses to M80442

Kernels from both the F1 progeny of the crosses between the transgenic line with the M80442 event as a pollen donor and the 24 genetically distinct pollen recipient lines as female plants and the control kernels obtained by self pollination of the parental lines were analyzed by Near Infrared Transmittance (NIT) to determine density. Kernels from ten ears for each cross and five ears from each self were analyzed individually and the average density reported in Table 2. For comparison purposes, the density of kernals a corn line homozygous for the opaque-2 mutation, LH244(o2), were also determined. Kernels derived from crosses of transgenic corn line with the M80442 event to the I283669 and I226211 germplasm displayed densities that were at least about 1.24 grams/milliliter or greater.

TABLE 2

| Maize Line | Inbred density (g/ml) | Inbred density (StDev) | F1 density from cross to M80442 (g/ml) | F1 density from cross to M80442 (StDev) |
|---|---|---|---|---|
| Mon011 | 1.331 | 0.010 | 1.211 | 0.012 |
| Mon009 | 1.310 | 0.013 | 1.226 | 0.015 |
| Mon001 | 1.337 | 0.006 | 1.232 | 0.013 |
| Mon017 | 1.347 | 0.007 | 1.228 | 0.009 |
| Mon010 | 1.323 | 0.009 | 1.217 | 0.016 |
| I283669 | 1.347 | 0.007 | 1.268 | 0.014 |
| Mon012 | 1.330 | 0.009 | 1.214 | 0.011 |
| Mon019 | 1.336 | 0.007 | 1.228 | 0.017 |
| Mon013 | 1.329 | 0.006 | 1.221 | 0.011 |
| I226211 | 1.338 | 0.006 | 1.267 | 0.019 |
| Mon002 | 1.323 | 0.010 | 1.198 | 0.014 |
| Mon003 | 1.338 | 0.006 | 1.201 | 0.014 |
| Mon021 | 1.310 | 0.004 | 1.203 | 0.018 |
| LH244 | 1.329 | 0.012 | 1.186 | 0.008 |
| Mon014 | 1.334 | 0.010 | 1.205 | 0.011 |
| Mon004 | 1.314 | 0.008 | 1.219 | 0.011 |
| Mon022 | 1.361 | 0.006 | 1.206 | 0.012 |
| Mon005 | 1.323 | 0.016 | 1.219 | 0.013 |
| Mon015 | 1.293 | 0.020 | 1.202 | 0.009 |
| Mon023 | 1.329 | 0.005 | 1.221 | 0.024 |
| Mon006 | 1.320 | 0.013 | 1.207 | 0.012 |
| Mon007 | 1.317 | 0.012 | 1.219 | 0.012 |
| Mon016 | 1.327 | 0.011 | 1.230 | 0.012 |
| Mon008 | 1.292 | 0.012 | 1.196 | 0.014 |
| Mon024 | 1.334 | 0.004 | 1.218 | 0.010 |
| WS541-38 | 1.302 | 0.008 | 1.229 | 0.019 |
| M80442 | 1.194 | 0.007 | na | na |
| LH244(o2) | 1.196 | 0.010 | na | na |

Example 4

Analysis of Seed Storage Protein Content in Seed

MALDI-TOF MS (Matrix-Assisted-Laser-Desorption Ionization Time-Of-Flight Mass Spectrometry) analysis was used to confirm suppression of the 19 kD and 22 kD alpha-zeins in the F1 kernels produced by the corn lines resulting from the cross I283669×M80442 and I226211×M80442 F1 kernels. This analysis was conducted essentially as described by Adams et al. J Agric Food Chem. Apr. 7, 2004; 52(7):1842-9). As expected, both the 19 kD and the 22 kD alpha-zeins were suppressed in the I283669×M80442 and I226211×M80442 F1 kernels. Surprisingly, the content of the 27 kD gamma zein protein in the vitreous I283669×M80442 kernels was not significantly increased relative to the content of the 27 kD gamma zein protein in the opaque M80442 kernels. The content of the 27 kD gamma zein protein in the vitreous I226211×M80442 kernels was also not significantly increased relative to the content of the of the 27 kD gamma zein protein in the opaque M80442 kernels. The absence of a significant increase in the 27 kD gamma zein in the vitreous I283669×M80442 and I226211×M80442 F1 kernels was unexpected as it had previously been reported that modifiers of the opaque-2 mutations result in either 2 to 3 fold (Geetha et al. 1991) or 2 to 4 fold increases (Wallace, et al. Plant Physiol. 92, 191-196, 1990) in the 27 kD gamma zein content. It was also reported that modifiers of the floury-2 mutation were related to increases in gamma zein content (Lopes and Larkins, Crop Sci 31:1655, 1991). The absence of significant increases in the 27 kD gamma zein content of the vitreous kernels comprising the decreased alpha-zein storage protein content was thus not expected.

Example 5

Identification and Mapping of Modifier Loci

Figure 4:
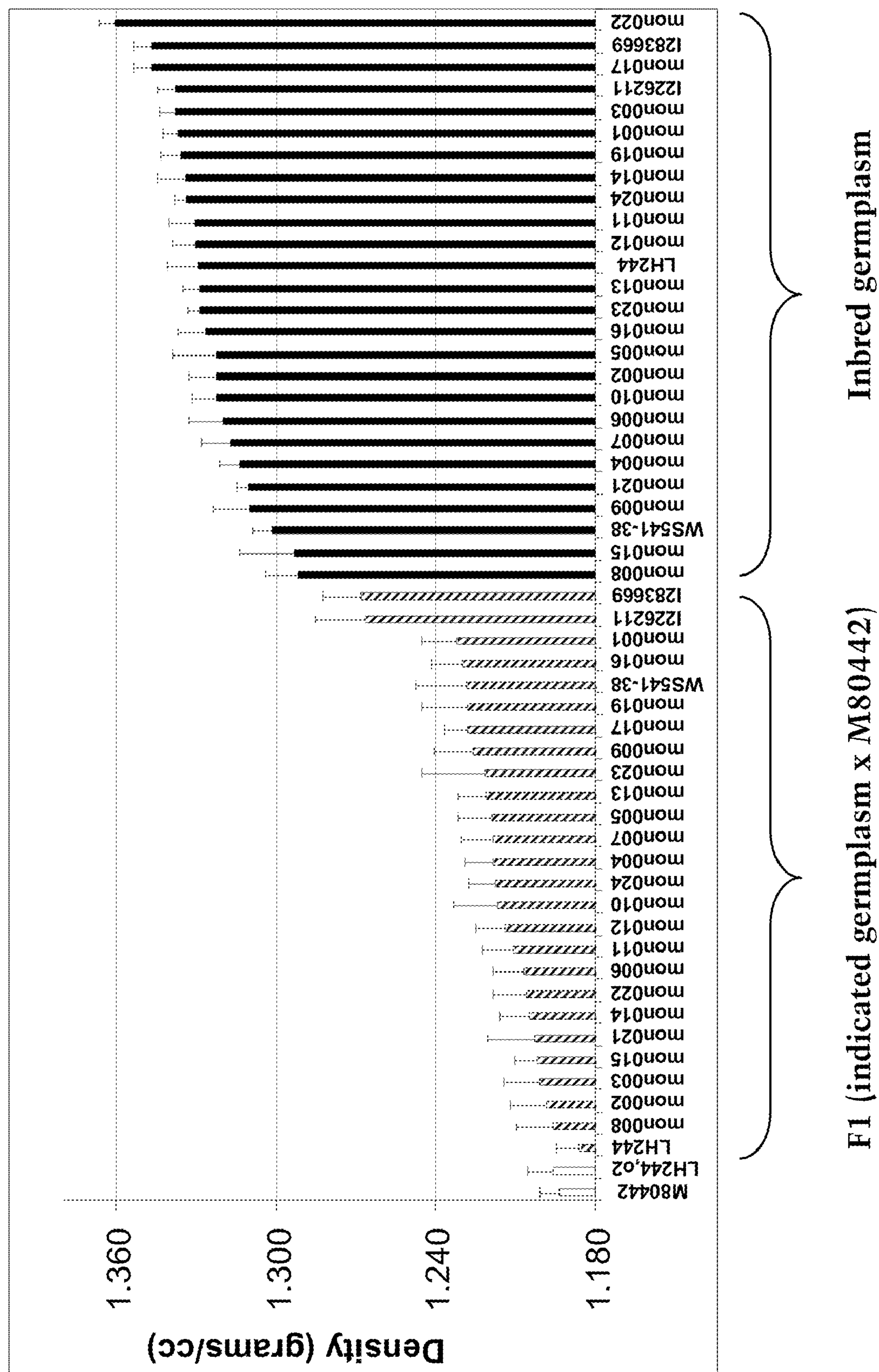
FIG. 4 illustrates the density of seeds of various genotypes. NIT density determinations for inbred germplasm (solid bars) that was crossed to the opaque transgenic line M80422 (open bar, far left) and for the F1 seed resulting from the gross of each inbred germplasm with M80422 (striped bars). The density for homozygous M80422 (open bar, far left) and for a homozygous opaque 2 mutant in LH244 (open bar, second from left) are shown for comparison.
Figure 5:
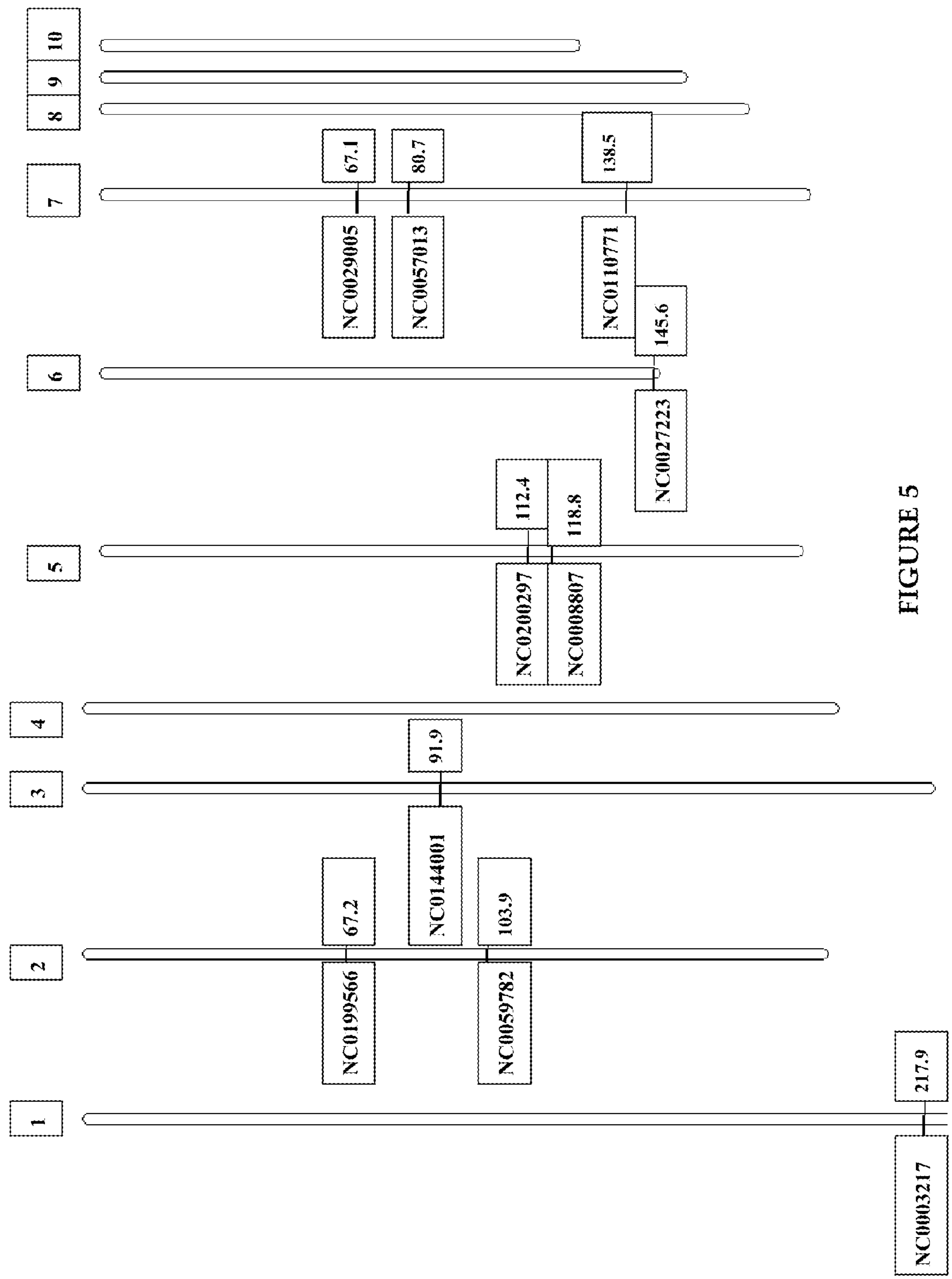
FIG. 5 illustrates a representation of the chromosome map of the maize genome showing the allele positions in common between I283669 and I226211 that contain linked opaque modifier loci and that differ from alleles in other lines tested that did not restore the vitreous phenotype to M80442 seed.

The 24 germplasm lines used for crossing to M80442 were also used to identify genetic loci and markers associated with the modifier(s) in I283669 and I226211 that provide(s) a vitreous kernel phenotype to corn lines comprising the M80442 transgene insertion. To do this, 6103 molecular markers were used to compare genotypes of the 24 lines tested lines. In addition, the molecular markers were also applied to parents in the lineage of I283669, mon019 and I226211. Line mon019 was selected because it belongs to the same high density group as I283669 yet failed to restore the vitreous phenotype in the F1 kernels. Markers that were identical between I283669 and mon019 were subtracted as non-informative. Markers that remained were alleles that differed between I283669 and mon019. These alleles were then compared to I226211 to find alleles from this set where I283669 and I226211 were identical. This shorter list of alleles were then compared with mon022. Line mon022 was the densest, non-transformed line but did not have the modifier. An allele count of this short set of markers where I283669 was identical to I226211 but differed from mon019 and mon022 was taken and those with counts of four or less out of a possible score of 24 were selected. This represents marker alleles that are putatively involved in the modification of the opaque phenotype, of which there were seven representing 6 regions. The putative alleles were mapped in relationship to each other and are shown in FIG. 4.

A complete listing of the markers linked to potential opaque modifier locus or loci in I283669 or I226211 that provide for restoration of a vitreous kernel phenotype to corn lines comprising the M80442 transgene insertion are provided in Tables 3 and 4.

TABLE 3

I226211 markers for opaque modifier loci

| Marker name | Allele and position in sequence[1] | Chromosome | Position on chromosome (cM) | SEQ ID NO. |
|---|---|---|---|---|
| NC0111829 | PO = G > T/PP = 142 | 1 | 0.3 | 1 |
| NC0024027 | PO = C > T/PP = 141 | 1 | 1 | 2 |
| NC0147202 | PO = C > T/PP = 535 | 1 | 6.7 | 3 |
| NC0148452 | PO = C > G/PP = 391 | 1 | 6.7 | 4 |
| NC0111443 | PO = A > G/PP = 367 | 1 | 10.3 | 5 |
| NC0145635 | PO = A > C/PP = 113 | 1 | 18.5 | 6 |
| NC0070876 | PO = C > G/PP = 470 | 1 | 19.7 | 7 |
| NC0043185 | PO = A > G/PP = 230 | 1 | 22.6 | 8 |
| NC0068027 | PO = A > G/PP = 365 | 1 | 23 | 9 |
| NC0025418 | PO = *** > ATC/PP = 225(227) | 1 | 26.4 | 10 |
| NC0028164 | PO = C > G/PP = 268 | 1 | 30.1 | 11 |
| NC0113465 | PO = C > T/PP = 80 | 1 | 34.6 | 12 |
| NC0106004 | PO = C > T/PP = 212 | 1 | 44.6 | 13 |
| NC0003429 | PO = C > T/PP = 449 | 1 | 49.5 | 14 |
| NC0052741 | PO = A > G/PP = 417 | 1 | 49.5 | 15 |
| NC0052744 | PO = G > T/PP = 569 | 1 | 49.5 | 16 |
| NC0036278 | PO = * > A/PP = 441 | 1 | 55.7 | 17 |
| NC0113273 | PO = A > C/PP = 118 | 1 | 58.2 | 18 |
| NC0000116 | PO = A > G/PP = 284 | 1 | 66 | 19 |
| NC0009159 | PO = A > G/PP = 273 | 1 | 66 | 20 |
| NC0014299 | PP = 488 | 1 | 70.2 | 21 |
| NC0033819 | PO = A > G/PP = 320 | 1 | 70.2 | 22 |
| NC0038788 | PO = G > T/PP = 402 | 1 | 70.7 | 23 |

TABLE 3-continued

I226211 markers for opaque modifier loci

| Marker name | Allele and position in sequence[1] | Chromosome | Position on chromosome (cM) | SEQ ID NO. |
|---|---|---|---|---|
| NC0143100 | PO = C > G/PP = 330 | 1 | 72.2 | 24 |
| NC0009578 | PO = A > G/PP = 196 | 1 | 73.5 | 25 |
| NC0068262 | PO = G > T/PP = 468 | 1 | 77.8 | 26 |
| NC0144090 | PO = A > G/PP = 410 | 1 | 108.6 | 27 |
| NC0143254 | PO = A > G/PP = 171 | 1 | 110.9 | 28 |
| NC0080733 | PO = C > T/PP = 804 | 1 | 111 | 29 |
| NC0002688 | PO = C > T/PP = 69 | 1 | 114.6 | 30 |
| NC0060430 | PO = A > G/PP = 63 | 1 | 114.8 | 31 |
| NC0111365 | PO = C > T/PP = 77 | 1 | 116.3 | 32 |
| NC0107701 | PO = A > G/PP = 377 | 1 | 121 | 33 |
| NC0036448 | PO = C > T/PP = 202 | 1 | 124.4 | 34 |
| NC0002635 | PO = C > G/PP = 199 | 1 | 254.8 | 35 |
| NC0144276 | PO = A > G/PP = 44 | 2 | 1.5 | 36 |
| NC0145267 | PO = A > G/PP = 57 | 2 | 1.5 | 37 |
| NC0110069 | PO = A > G/PP = 314 | 4 | 34.4 | 38 |
| NC0111464 | PO = A > G/PP = 115 | 4 | 34.4 | 39 |
| NC0019003 | PO = G > T/PP = 405 | 4 | 45.3 | 40 |
| NC0010671 | PO = A > C/PP = 72 | 4 | 63.7 | 41 |
| NC0105263 | PO = G > T/PP = 238 | 4 | 65.9 | 42 |
| NC0038855 | PO = C > G/PP = 74 | 4 | 67.1 | 43 |
| NC0070730 | PO = C > G/PP = 331 | 4 | 67.8 | 44 |
| NC0035683 | PO = C > T/PP = 245 | 4 | 68.4 | 45 |
| NC0038900 | PO = C > T/PP = 278 | 4 | 69.3 | 46 |
| NC0033483 | PO = C > T/PP = 163 | 4 | 69.5 | 47 |
| NC0034464 | PO = A > T/PP = 125 | 4 | 73.5 | 48 |
| NC0036528 | PO = **** > CATC/ PP = 356(359) | 4 | 74 | 49 |
| NC0038852 | PO = C > G/PP = 551 | 4 | 74 | 50 |
| NC0002585 | PO = C > T/PP = 224 | 4 | 74.4 | 51 |
| NC0015574 | PO = C > T/PP = 68 | 4 | 74.4 | 52 |
| NC0005451 | PO = A > G/PP = 224 | 4 | 74.8 | 53 |
| NC0014666 | PO = C > G/PP = 126 | 4 | 77.8 | 54 |
| NC0020374 | PO = G > T/PP = 397 | 4 | 77.8 | 55 |
| NC0066430 | PO = A > G/PP = 604 | 4 | 77.8 | 56 |
| NC0068131 | PO = C > T/PP = 387 | 4 | 77.8 | 57 |
| NC0078135 | PO = A > G/PP = 321 | 4 | 77.8 | 58 |
| NC0029788 | PO = C > G/PP = 172 | 4 | 80.5 | 59 |
| NC0037873 | PO = A > G/PP = 129 | 4 | 88.3 | 60 |
| NC0003695 | PO = A > C/PP = 329 | 4 | 104.2 | 61 |
| NC0005275 | PO = A > G/PP = 223 | 5 | 36 | 62 |
| NC0067802 | PO = C > G/PP = 242 | 5 | 36.1 | 63 |
| NC0020668 | PO = G > T/PP = 544 | 5 | 36.2 | 64 |
| NC0038726 | PO = C > T/PP = 652 | 5 | 40.1 | 65 |
| NC0079943 | PO = A > G/PP = 301 | 5 | 40.2 | 66 |
| NC0113172 | O = C > G/PP = 327 | 5 | 43.8 | 67 |
| NC0020401 | PO = C > T/PP = 175 | 5 | 48 | 68 |
| NC0111398 | PO = C > T/PP = 182 | 5 | 67.7 | 69 |
| NC0023808 | PO = C > G/PP = 271 | 5 | 73.8 | 70 |
| NC0051419 | PO = C > T/PP = 252 | 5 | 73.8 | 71 |
| NC0107549 | PO = C > T/PP = 372 | 5 | 79 | 72 |
| NC0078535 | PO = A > G/PP = 104 | 5 | 83.9 | 73 |
| NC0040366 | PO = A > C/PP = 119 | 5 | 84.1 | 74 |
| NC0146245 | PO = * > A/PP = 333 | 5 | 84.7 | 75 |
| NC0035956 | PO = A > C/PP = 246 | 5 | 85.1 | 76 |
| NC0145634 | PO = C > T/PP = 349 | 5 | 85.4 | 77 |
| NC0144687 | PO = A > T/PP = 261 | 5 | 90.2 | 78 |
| NC0027864 | PO = C > T/PP = 182 | 5 | 93.9 | 79 |
| NC0053792 | PO = C > T/PP = 384 | 5 | 93.9 | 80 |
| NC0110484 | PO = A > C/PP = 215 | 5 | 159.5 | 81 |
| NC0021585 | PO = C > G/PP = 234 | 5 | 175 | 82 |
| NC0029924 | PO = C > T/PP = 222 | 6 | 109.2 | 83 |
| NC0107449 | PO = C > T/PP = 285 | 6 | 118.1 | 84 |
| NC0068954 | PO = G > T/PP = 215 | 7 | 48.4 | 85 |
| NC0037029 | PO = C > G/PP = 396 | 9 | 119.9 | 86 |
| NC0154919 | PO = C > G/PP = 302 | 10 | 40 | 87 |
| NC0143754 | PO = C > T/PP = 177 | 10 | 49.2 | 88 |
| NC0005140 | PO = C > T/PP = 348 | 10 | 51 | 89 |
| NC0043776 | PO = A > G/PP = 74 | 10 | 53 | 90 |
| NC0039275 | PO = C > T/PP = 397 | 10 | 55.4 | 91 |
| NC0003640 | PO = C > G/PP = 445 | 10 | 58.9 | 92 |
| NC0016730 | PO = A > G/PP = 303 | 10 | 63.8 | 93 |
| NC0031358 | PO = ********* > CATTGTTGT/ PP = 507(515) | 10 | 64.2 | 94 |
| NC0011002 | PO = A > C/PP = 174 | 10 | 66.5 | 95 |
| NC0152708 | PO = C > T/PP = 137 | 10 | 74.9 | 96 |
| NC0027447 | PO = C > G/PP = 311 | 10 | 75.6 | 97 |
| NC0013745 | PO = A > G/PP = 52 | 10 | 79 | 98 |
| NC0113140 | PO = C > T/PP = 283 | 10 | 101.6 | 99 |
| NC0107333 | PO = C > T/PP = 176 | 10 | 113.1 | 100 |
| NC0109666 | PO = C > G/PP = 75 | 10 | 113.1 | 101 |

[1]Allele in opaque modifier germplasm is "X" where PO = X > Y. Position of allele in indicated SEQ ID NO is XXX where PP = XXX.

TABLE 4

I283669 markers for opaque modifier loci

| Marker | Allele and position in sequence[1] | Chromosome | Position on chromosome (cM) | SEQ ID NO. |
|---|---|---|---|---|
| NC0003217 | PO = A > G/PP = 464 | 1 | 217.9 | 102 |
| NC0199566 | PO = A > T/PP = 189 | 2 | 67.2 | 103 |
| NC0059782 | PO = A > C/PP = 167 | 2 | 103.9 | 104 |
| NC0144001 | PO = A > C/PP = 145 | 3 | 91.9 | 105 |
| NC0200297 | PO = C > T/PP = 241 | 5 | 112.4 | 106 |
| NC0027223 | PO = C > T/PP = 480 | 6 | 145.8 | 107 |
| NC0029005 | PO = A > G/PP = 244 | 7 | 67.1 | 108 |
| NC0110771 | PO = A > C/PP = 490 | 7 | 138.5 | 109 |
| NC0008807 | PO = C > T/PP = 291 | 5 | 118.8 | 110 |
| NC0057013 | PO = A > G/PP = 222 | 7 | 80.7 | 111 |

[1]Allele in opaque modifier germplasm is "X" where PO = X > Y. Position of allele in indicated SEQ ID NO is XXX where PP = XXX.

Example 6

Methods of Producing Corn Plants, Seed and Processed Corn Products

This example illustrates methods of producing corn plants, seed, and processed corn seed products of this invention from corn lines with reduced alpha zein content resulting in enhanced nutritional value, soft kernel and opaque phenotype. Corn lines with reduced alpha zein content include the transgenic corn line designated as event M80442 as produced in Example 1, a mutant homozygous corn line with the opaque 2 locus, a mutant homozygous corn line with the floury 2 locus, a mutant homozygous corn line with the De-B30 locus and a mutant homozygous corn line with the Mc locus. Each of the corn lines with reduced alpha zein content is crossed with each of the corn lines with an opaque modifier locus, i.e. corn line I226211 and corn line I183669. Seed from these crosses is analyzed for hardness and vitreous kernel. Seed with density greater that 1.24 grams/milliliter is analyzed for the presence of an opaque modifier locus. Progeny seed with an opaque modifier locus is selected for backcrossing with each of the parental corn lines with reduced alpha zein line. Backcrossed corn lines for each of the parental lines with reduced alpha zein content are used for making hybrid corn lines that produce corn kernels with enhance nutritional value and a vitreous phenotype. The corn kernels with enhanced nutritional value and a vitreous phenotype are processed into processed corn seed products with enhanced nutritional value. The corn plants, corn seed and processed corn seed products have genomic DNA having a genetic element that imparts to a corn seed (a) enhanced nutritional value from an increase in lysine and tryptophan, and (b) soft, brittle and opaque kernel shells, both resulting from a reduced alpha-zein storage protein content in the range of at least 10% to at least 50% reduction as compared to control, the improvement comprising the presence of at least one stably introduced opaque modifier locus on at least one chromosome wherein the opaque modifier locus restores kernel hardness and does not result in a significant increase in a 27 kilodalton gamma zein storage protein content, and wherein the kernel hardness is observable by the presence of a vitreous kernel.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A corn seed comprising a vitreous kernel phenotype, at least one genetic element that comprises one or more recombinant DNA(s) encoding one or more transgene(s) that reduce(s) expression of both 19 kilodalton (kD) and 22 kilodalton (kD) alpha-zein storage relative to a control seed, and at least one opaque modifier locus that imparts said vitreous kernel phenotype to said seed comprising said genetic element, wherein a 27 kilodalton gamma zein storage protein content in said corn seed is less than 2-fold higher than that of a seed of the same variety that contains said genetic element but lacks said opaque modifier, and wherein said vitreous seed has a kernel density of at least about 1.24 grams/milliliter, and wherein said opaque modifier comprises at least one genetic locus present in corn line I226211 germplasm deposited as seed under ATCC Accession No. PTA-8214 or wherein said opaque modifier comprises at least one genetic locus present in corn line I283669 germplasm deposited as seed under ATCC Accession No. PTA-8569.

2. The corn seed of claim 1, wherein said recombinant DNA comprises in 5' to 3' order a promoter element operably linked to an anti-sense-oriented DNA element 1 from a 19 kD alpha-zein gene, an anti-sense-oriented DNA element 2 from a 22 kD alpha-zein gene, a sense-oriented DNA element 3 from said 22 kD alpha-zein gene that is shorter than the anti-sense-oriented DNA element 2 and is complementary to only the 5' end of element 2 and a sense-oriented DNA element 4 from a 19 kD alpha-zein gene that is complementary to at least a portion of the 5' end of element 1.

3. The corn seed of claim 1, wherein said recombinant DNA comprises a vector that provides for expression of a 24 kilodalton alpha-zein protein obtained from a floury-2 mutant in said corn seed.

4. The corn seed of claim 1, said seed comprising an alpha-zein storage protein content is of less than 50% of an alpha-zein seed storage protein content of control seed.

5. The corn seed of claim 1, wherein a total lysine content of said seed is in the range of about 3000 to about 5300 ppm by weight.

6. The corn seed of claim 1, wherein said opaque modifier comprises at least one genetic locus present in corn line I283669 germplasm and wherein said genetic locus is linked to a marker selected from Table 4.

7. The corn seed of claim 1, wherein said opaque modifier comprises at least one genetic locus present in corn line I226211 germplasm and wherein said genetic locus is linked to a marker selected from Table 3.

8. The corn seed of claim 1, wherein said corn seed does not comprise an opaque modifier selected from the group consisting of in Pool 15, Pool 17, Pool 18, Pool 23, Pool 24, Pool 25, Pool 26, Pool 27, Pool 29, Pool 31, Pool 32, Pool 33 or Pool 34 QPM (Quality Protein Maize) opaque modifiers.

9. A corn plant obtained from the seed of claim 1.

10. The corn seed of claim 1, wherein said corn seed comprises a 27 kD gamma zein storage protein content that is less than 1.8-fold than that of seed of the same variety that contain the genetic element but lacks the opaque modifier.

11. The corn seed of claim 1, wherein said corn seed comprises a 27 kD gamma zein storage protein content that is less than 1.2 fold higher than that of seed of the same variety that contains the genetic element but lacks the opaque modifier.

12. The corn seed of claim 1, wherein said corn seed comprises an increase in 27 kD gamma zein storage protein content that is less than 5% relative to the gamma zein storage protein content in a parental corn plant seed with an opaque kernel phenotype and a reduced alpha-zein storage protein content.

* * * * *

SEQUENCE LISTING

```
<160> NUMBER OF SEQ ID NOS: 111

<210> SEQ ID NO 1
<211> LENGTH: 733
<212> TYPE: DNA
<213> ORGANISM: Zea mays

<400> SEQUENCE: 1

tggcggctac tagggcatgt catgaccaga cgtggtcagc tcagtgagtt gtgatcctgc     60

aataactcaa ttggtgctct ctagagttat tggagaatat caacttagat tggattctct    120

ctttgttgtt ctactgtctt tgcttagtta agcacttcag ccatatgcca ttcgtaatga    180

aatagctttg gatgttgcag aaaattttga ttgacataga gagtcctatt ttgacctttg    240

taccactgct ttaatttgaa tgtggtacaa ggagaaacat accaaagttc gaggtaagac    300

actggatcat ttgaactttc tagcgttgtt tagtttcata tttctgccat catgcatact    360

taaattgtga aatgtgtata tgtagttctt aacatatgtt aagtagcatg tggttttagt    420

tttttaccct cttctaaatt gggatatagt ctttccgtac ctttatgatt gaggttatag    480

cagttttttg tgctcaaatt aacaaaaaag tatagaataa ccacatgctt ctattaaacc    540

tgccttttc tactttgcaa cttaaattaa ttctcctaaa atgcatacat ttgcattgtt    600

caaaactata aatttgtcga ttgttccact atttaagata catttttaga tactgtgatt    660

gatctcatta aaccatgttg gtttctacaa ccaacttaac agtcaaggaa aatttacatt    720

ggtaccggac gca                                                       733


<210> SEQ ID NO 2
<211> LENGTH: 800
<212> TYPE: DNA
<213> ORGANISM: Zea mays

<400> SEQUENCE: 2

aagttacatt tactacatgt agaaaatcct ttaggtacct tgagaaccat aaccacaagc     60

tttgcatatg aatcaatgga gaaatatgaa atgtgaggtt gctgtggtga ttgctgagat    120

gatccaccag gagcaacgat ttgctcggag actagagagt gtgtaacagc aagttcctga    180

acgattcaaa ataagtatct gagtatgaca aagtgtactg cataatctgg tacaaaggta    240

gatccatcac cgtgagaata cggaagaagc gttcagagat atcatccccc ttcagcagac    300

catcttgctg caactgtgtg acaaaacgag tgtatgccgc atcactagca cttacatgat    360

tacacatctg acaccattca gaaaacagga ctgccacctg tacatcgaac aatttaacag    420

attaattaac agtccagcaa atagattcaa ggtatagttg tgagaatggc ttgagcaaga    480

acagcaacaa aatacaggta acaccaccat tggaagacta caactatctc ctagttgaac    540

taacatgcta atatgtgacc acatcaccgc aatcatgaga ggaaattcta tgagtagaaa    600

aaggaacatc caagatacaa acaaaatcgt tgcttattta tactaaggaa ttctgatccc    660

atacccaaca aattgaaaaa tggaatcaaa gaaaacagaa acagaaccaa aaccaaaaca    720
```

```
tctaactaaa aataaagaga ataggtttat gtaaattaaa caaaggttct tgtaaatctg    780

taggattcat gatgcataaa                                                800


<210> SEQ ID NO 3
<211> LENGTH: 772
<212> TYPE: DNA
<213> ORGANISM: Zea mays

<400> SEQUENCE: 3

cttcagacac actctgttta ttcggtgtac ctagtatcct tcagcagtgg caatgacaca     60

aacaaagtca gacaggtcta aaatacgcaa atacagaata agaaatttaa tgccagcaca    120

atcatagaac ctgaatatct taaaaagttc gtcgatctca gaatcgccag ggaatagtgg    180

cttttggttc accatttccg caaagataca gcccacagac cacacatcaa ctggtgtgga    240

atactgcctc gctccaagca gaatttctgg agctctgtac cataatgtca ctacctgaaa    300

aatacttcca tagatatgta ctgtgaatta atgtgactag aatatacagc aaaaggttac    360

gttattcggg taaaaaattg tgggaatcca taactttggc atccctcaca atattttttc    420

cctaacagga caattcaaac tccctttctc aagttagagc ataacaatta acaaatgtac    480

ctcatgagta aatgtacgga caggaattcc aaatgccctg gctaaaccaa agtctgcaag    540

cttcagtgca ttagtgcgcc gatctatcaa taagttttga ggtttcaagt ctcgatgaag    600

aactctatga gaatggcagt acgcaacacc atggagtatc tggtagaggt atgactggag    660

aaagaagaaa atagttacat ttcagaatgc acccacaggc acctgcacct cattcatttt    720

caggttatga gatataatgg aaatgaggaa agggaaaaaa aatgggatga aa            772


<210> SEQ ID NO 4
<211> LENGTH: 835
<212> TYPE: DNA
<213> ORGANISM: Zea mays

<400> SEQUENCE: 4

ctgctcttcg gtgtacctag tatccttcaa cagtggcaat gacacaaaca aagtcagaca     60

ggtctaaaat acgcaaatac agaataagaa atttaatgcc agcacaatca tagaacctga    120

atatcttaaa aagttcgtcg atctcagaat cgccagggaa tagtggcttt tggttcacca    180

tttccgcaaa gatacagccc acagaccaca catcaactgg tgtggaatac tgcctcgctc    240

caagcagaat ttctggagct ctgtaccata atgtcactac ctgaaaaata cttccataga    300

tatgtactgt gaattaatgt gactagaata tacagcaaaa ggttacgtta ttcgggtaaa    360

aaattgtggg aatccataac tttggcatcc ctcacaatat tttttcccta acaggacaat    420

tcaaactccc tttctcaagt tagagcataa caattaacaa atgtacctca tgagtaaatg    480

tacggacagg aattccaaat gccctggcta aaccaaagtc tgcaagcttc agtgcattag    540

tgcgccgatc tatcaataag ttttgaggtt tcaagtctcg atgaagaact ctatgagaat    600

ggcagtacgc aacaccatgg agtatctggt agaggtatga ctggagaaag aagaaatagt    660

tacatttcag aatgcaccca caagcacctg cacctcattc attttcaggt tatgagatat    720

aatggaaatg aggaaaggga aataaatagg atgaaaaact tctagtcaca ttaatcttgt    780

tcactatgta acacactccc accaagtaga agtaatttgc tgcaatgcat tgaat         835


<210> SEQ ID NO 5
<211> LENGTH: 735
<212> TYPE: DNA
<213> ORGANISM: Zea mays
```

<400> SEQUENCE: 5

```
tgacaaacac ttcttgtatt accgtgctcg gttgattgaa gagactggct gcgcgatgta      60
ttttatcttg acgtgtgtga ggctgaccac gttatcctat ccaggaagtg gctgtgcaag     120
ggcaagacaa ggtgtacaaa gatgtgatag agcctctcga gagtgtgagc gtcaactcta     180
ttccaactag caaggaggat atccgtgatc ttggtcctcc ggataaggtt tactattctc     240
ttttccataa ataaacttgg atagtccata ggtatctagt ggaaaaaggt ccaattttga     300
tgttttaact cctgtttgtc aggttgccga ggctctgatt aaaaaagttt tggcaccatc     360
aacacaaaag acaaagttaa ttgaggcgaa agaggtgtgc cttccgtcca attttccgtg     420
cttggcctaa ctattcctgt taatattctt ggacaccagt gcgtgtcaaa tctttgagga     480
tcaggcaatg atgatttgtg acatagcatg gttctttaaa taagttcatt cacgcatgcc     540
gattggttta cgtggacaga attataaaag acggaatgag cttagttggt gctgattgac     600
gaatctctct gagtccattt tatttaggtt gagcagtaag ctgaacagct actctctgaa     660
aatagcaaat gtactaatga atggtttcca cctacaacat gtattgagat ttgttgcctg     720
gtttccaagt ttcag                                                      735
```

<210> SEQ ID NO 6
<211> LENGTH: 535
<212> TYPE: DNA
<213> ORGANISM: Zea mays

<400> SEQUENCE: 6

```
acttcttatt ctaccaccac ccgcctcctc tcgagttcga tctgtttgct cccccagaca      60
tgtcgggccg cggcaaggga ggcaagggcc tgggtaaggg cggcgcgaaa cgacaccgca     120
aggtgctccg cgacaacatc cagggcatca cgaagccggc catccggagg ctggcgcgca     180
ggggcggcgt gaagcgcatc tccgggctca tctacgagga gacccgcggc gtgctcaaga     240
tctttctcga gaacgtcatc cgcgacgccg tcacctacac ggagcacgca cggcgcaaga     300
ccgtcacagc catggacgtc gtctacgcgc tcaagcgcca gggccgcacc ctttacggct     360
tcggcggcta gggcgctagg ctaggccatg ctcgacccgc cccccactct ctccctctgg     420
cgtcgtcact ggttccttga cccctgtgcg ggtcggtcgg tggtgctagg gtcagcagtt     480
gtctggtgtc tgtagcctct ctggctatcc gttctttggt gtgaaatgaa attcc          535
```

<210> SEQ ID NO 7
<211> LENGTH: 1232
<212> TYPE: DNA
<213> ORGANISM: Zea mays

<400> SEQUENCE: 7

```
cttgcatgcc tgcagcgaca ataccggcac gctcaccctc aacaagctca gcgtcgaccg      60
caccctcgtt gagatcttcg ccgcgggcgt tacgaaggac gacgttatct tgttcgccgc     120
cagggcgtct agggtggaga accaggacgc catcgacgcc gccatggtcg gtatgctggg     180
tgacccgaag gaggccaggg acggcatcga ggaggtgcac ttcttcccgt tcaaccccgt     240
cgacaagcga acggctctca cctacatcga tctggccgat gggagctggc accgtgtcag     300
caagggtgca ccagaacagg tacgtagtcg tgcatggctt tctcatgcat ctcttctttt     360
ttttctgaat tttctgttgg attttcttcc gagaccctgt gcatgcggat gcatgagatc     420
agatggattt tctgttggag cagccatgca ttcggtgccc gagaatagac gagttttacg     480
tttttctgtt atttattttc tgattttcaa aattcatttc ctgagctttt ttttaatgtt     540
```

```
actctcctat ggcacgcaga tactggctct ctgcaactgt ggagacgacg tgtgcaactt    600

ggttcacact gtgatagaca aatatgccga gcgtggtctt cgatctcttg cggttgcaag    660

acaggtatgg ttttatgact ctcagagttt gcaagacagg tatggttata tgaatacatt    720

agataatgct ttatcctgct ttcctacagc aagttccgga gaagagcaaa gagagcctcg    780

gagatccatg ggaattcgtt ggtctgcttc ctctgctgga ccctccgagg tcggacagct    840

ccgacacaat caagcgcgcg ctcgacctcg gtgtcaacgt caagatgatc accggtacgc    900

ctcgcattcc gagaggtttc tttcactcac gttgctatgt tctgacaatg gtcgcaacct    960

gcttgcattg caggtgacca gctcgccatt gccaaggaga ccgggagacg gctagggatg   1020

ggcaccaaca tgtacccgtc gtccgctctg ctcgggcaga gcaaagatga agccaccgct   1080

tcggtccccg tggacgactt gatcgagaag gccgacggct ttgctggcgt cttcccaggt   1140

agggaggagg gagggggttt gcattgcaat gtgcatgaac tgctataaca agtgcgttct   1200

tgatgcagag cacaagtacg agatcgtcaa ga                                 1232
```

<210> SEQ ID NO 8
<211> LENGTH: 796
<212> TYPE: DNA
<213> ORGANISM: Zea mays

<400> SEQUENCE: 8

```
ctgacttgct gggagtcaaa atgtctgtct ggccgggcag ggggtggaaa cttggaggcg     60

ctgtcgtgga gccggaggct caagatcgcc acgggcgcgg cgcgcggcct cgccttcctg    120

cactcgtcgg agaaacaggt catccacagg gacttcaagg cgtccaacat cctcctcgac    180

tcggtaatct tcagcaaaag caagcatgcg atatgaaggt cttctcctta gctaccatgt    240

ccactaacca aagacatgcc aggatttcac cgcgaagctg tcggacttcg ggctcgccaa    300

gaacgggccc tccgcgggga cgtcgcacgt cacgacccgg gtcatggtcg cctacggcta    360

cgcggcgccg gagtacgtcg ccaccggtat gtaggttcct gcacccgcac gagcgtgacg    420

gcggtgatga tgcacggcgc ggccaccagg cgcagccgcc ccacgtacgt acgttgacgc    480

cgtgcatgca gggcaactgt acgtcaagag cgacgtgtac ggcttcagcg tggtgctgct    540

ggagctgctg acgggactgc gcgcgcacga cctgaaccgg ccgacccacc agcacagcct    600

ggtggagtgg gcgcggcctt atctctccgc cggcgccggc aagctcaaga gcctcatgga    660

cgagcggatg gacggccagt accacaccaa ggccgcgctc tcggggtcgc caggctcgcc    720

ggcaagtgcc tcaacagcga ccgcaagagc cgcccttcca tggacgacgt cgtcgccgcg    780

ctcgaggaca tcgagg                                                    796
```

<210> SEQ ID NO 9
<211> LENGTH: 901
<212> TYPE: DNA
<213> ORGANISM: Zea mays

<400> SEQUENCE: 9

```
aagactagac ttcacaaaaa atactgaact taagctgcat aagacaggtc tcatagtaga     60

ctatgcctac tcccagcctt gggctgtcgg cggggctgct tggtcccaac cagtaggagc    120

aaccactgga tgtacagtac cgtccgcagg tacaggggcc ccggcttgat cccagccttc    180

accggtagga actggagctg caaacgaaat tgggaatcgt catgttagga caacagtaac    240

tcggtacaaa gtagaactgt cagtgttata gttttcttgt gaacacaaca tgcatgggct    300

caagaagtct aataccaaag atgagaaaat tttaaaagta aggaggaggt aaccgtatat    360
```

```
acccagagca gcaccccaat cagcaccagt aggagcaaca ggtggtgcag ccacatcaga    420

ggtccactga tcaccacccc actgatcagc tccttggtaa tcagtgattg cggcaaactc    480

aggggccgcg gcagcttcct cctcctgctc ctttgcttcc tctgggtctc tgtagaagaa    540

cagatcgacc tgcaaacaac attatcatat aagaatgcaa aggttaccaa aaaaatctgg    600

actcatagca tctccaatgt cattttgaac agcgtcataa gctagcatac catgacttcc    660

cacttgtgcc caggaaggat agtgcccctc atttgcagaa ccatcctgga cagaagccag    720

aacagacatc caatgctgtt cctccccttg ttgttcgctg ggatgccgat atcgacgtac    780

cgcatgggag agtcagtgtc acaaaaggca atggtcggga tgttccccag agcagactcc    840

ttgattggct gcaaacgatt accagcataa caattagttc accatcacac tgcaggcatg    900

c                                                                    901
```

<210> SEQ ID NO 10
<211> LENGTH: 805
<212> TYPE: DNA
<213> ORGANISM: Zea mays

<400> SEQUENCE: 10

```
tgtatcatgg acacattttc attggtgtgc ttatctctta tgcagtgcca ttgttatgtc     60

tgtgattgtc ctgctccctg tgccctatgg gacaagcatt gtcatgctac ggacaaggat    120

agaaagtgga agagacttag ggaaatatcc aaaaataaaa gccagccaaa tcctaaacga    180

agaatacccc agcatttcaa acgctcagtc acaacaggac catcatcctc acagtattcc    240

gcaaatatga ctggttttac tggaagattt cctgcttcgg gtactgcgaa ccaaattcaa    300

caggtggata tctctgttat ggttgcacag gatatggtga ggggtatcag tctgccgagt    360

gcaccatctc ctacgccaag aactaaaaat cggagctatg gatccaaagg tgcccagatt    420

gctcctccaa tttatacatt ctcaaatgat aatcatttcc agccttctgt tcctagctat    480

ggtctggtgc ggcctcatgc atctaaaact gcacatgttt catcaggagg tcatgttagc    540

gctaagactt ttcagagtaa cccatctcag ttttgtgttc gtgcaccaat gggatctcat    600

ggacacaggt accgaccacc atcatatcct cagcctcctc ctaacacagt tgttggcact    660

ggtgtgcccc tctcacggtg cgcctcgctg aacgctgagg gctcagggaa cacaacgccc    720

acaagttccg ccggcaggta caatatcgaa ggaatcactt gcaaatttgg cacgtcggct    780

gggattacct tattacaata ctaat                                          805
```

<210> SEQ ID NO 11
<211> LENGTH: 853
<212> TYPE: DNA
<213> ORGANISM: Zea mays

<400> SEQUENCE: 11

```
tcggctcccg gttttcctct agagccgacc tgcagcggat gcgaagggat cggccgcagc     60

agcagctgcc gtcggttggt cggggaaccg gaactcgctg ccaaacccgc gggactgctg    120

gagtgtctgg gcgaaggcct ggtacttgcg gatgtcggcg tcactcacgc tgcgacgggc    180

gtacttcatg gactcctcga agtgagcagc cttgatctca gcgatgtcgt ctacctcgtc    240

ttcctccata gcctcggggt tgtctttgct gcgcctctcc ctctcgatat cctgaaatca    300

aatgtcccgg ttagcaaaca ggtatactac tctacgaaac caaatgctgc aaaaaaccga    360

ttatgggcca agagattact acaccttctc gatgttctcc ctgatggcat acttgcacgc    420

gcgctggcag atctctgtga tatctgcacc gctgaaaccc tgggtgtatt tggcgagagc    480
```

```
attcaagtca acatccttgg ccacaggaga cttcctgaga caggctttga agatctgaag    540

cctggactgc tcatcgggca gaggaatata gataagctga tcaagacgcc caggcctcag    600

caaggctggg tcaatgatgt ccggtctgtt agttgcaccg ataataaaaa ccgtcttctt    660

ggcattcatg ccatccatct cagtaagcag ctgggtcaac accctatcag cagcaccacc    720

ggcgtcacca acactgcttc ctctctgaaa atcgcaatag ctgtcagtta caactcattt    780

gcaggttgtg tcagtgcgtg agcacaatgc ataatcgaga gaccatacct gagtagccat    840

ggagtcgagc tca                                                        853
```

<210> SEQ ID NO 12
<211> LENGTH: 682
<212> TYPE: DNA
<213> ORGANISM: Zea mays

<400> SEQUENCE: 12

```
tgttgaattt gctactctat acccccgctc aaaacgaatt tgctactcta tttctaatct     60

tcacggccac aggtaaaaac cctatatttg agggcatgtt aaccactgca caacacttta    120

cgactctgaa gaatgattaa tttgcagact caaagaaaag cacttggggt tgcaagtgac    180

ccttttcaca catcacgagc acatcacccc aactacctac aacctgcaca aataacatgg    240

aaccaaaatt gggccacatt agtacgaaca gtaaaaagga tgctcaaagt agtatggtta    300

ttgggttacc ttgactgtct ggtcatcata catgatccat cgtccatcct tgaaggcaaa    360

acaatgataa tgctggccat agtagcaaac ctgcaggagt aaaaaagcaa taatgttata    420

tatctaatgc tccttgcatc gacagacaga tgccaagcac cagctttaga taaaagacta    480

tgtaaagaca tgatgtttac ttcaaaatgc aacacacctt tactgtaaat ccattatatg    540

gagaaaatat gtcatttggt aggtatagta atgaagctaa atgggaaaaa aaattgacaa    600

caaatggaaa gattgacaat aatgttacac ctttttttacc acaatcagca ataacaatac    660

agtcacatta acgttatatg ca                                              682
```

<210> SEQ ID NO 13
<211> LENGTH: 513
<212> TYPE: DNA
<213> ORGANISM: Zea mays

<400> SEQUENCE: 13

```
tcgagctcgg taccccctgta atgcaacgtg ccaaatttgc attccctttt acaccacgga     60

acgtaggaaa cggaaacatt tttttcccga acagaataaa tataaaacaa tggtagaaag    120

cgtaacctga gtcattcagc gctgatcagc ccataaagta aacacgcctt tgtgcgaggg    180

cgagtccaag ctccaaagtc cataccaaac atgccggttt gactttgtgc gaggagcaga    240

tgggctgggc attggctgct accagccctc aaccgcaggc ccttgttttt gggctagtcc    300

aactttcttt taaatgtgcg tttgggccag attgttagcg gagcaaagtg gagtgcccag    360

taggcccgca tcagaagaaa tggccttgtt ttgctgggcc acagcttgca cgtgcagccc    420

atgcacggaa cggatgcaca tgcacctgag cacagcactc gcttcacatc aactccggta    480

aatgagctct gcggtaagtc gaaaacatga aca                                  513
```

<210> SEQ ID NO 14
<211> LENGTH: 774
<212> TYPE: DNA
<213> ORGANISM: Zea mays

<400> SEQUENCE: 14
tgtctgcaca atcgaaatac aaatgtaaga aacatctaaa tgccacattc aattgttaca 60
taaaagcaat taatcgttga gtgatgatgt gattttattt ggtagggagc cagagtacta 120
catgtgtgca tgtaaagtta aaataaataa acctgcaaag attcagtatc gaagactcaa 180
aactcatctt caatgttgag attcaaaaca acacaaatgt ccttgtcaaa acatgatgaa 240
cagtccctga ttggctactg atctattttg tttcttaaca tctaggtcaa atttgaaaca 300
gaattgttgc agctatactt aaatttatgt gccaatcatc cggtccaacc atgagggatg 360
ccggtctgcg aacaccccca agagcaaaaa agtaatgttc agaatatcaa tacccaagcc 420
gaggttaaat tgagccctac tacatgagtg atgtggcaac aagacttcca tcaattcacc 480
aggatggatg cagaattcag aaaaggtcaa tatgatggat gtatttcaga aatccttgtt 540
cttgaaacaa aaaggctttg tgatgtgttg tcttcttcgt ggtgtgcgca agggagaatg 600
cagcagcagc gaggattggg gaagagagca cagggcatac ggaggacgat taccgccggc 660
cagattgccg aaggtaatcg ccccagaaca gggagactta tttttttctc gaaaacgcgc 720
aggagaactg tgccccttta tatattaaga agatagaata aaaaggtcta aaat 774

<210> SEQ ID NO 15
<211> LENGTH: 815
<212> TYPE: DNA
<213> ORGANISM: Zea mays

<400> SEQUENCE: 15
aagagctggc agccaagcgt gttaacgggg aatgctacca ctgtactgag aagtacagcg 60
cagatcataa gtgtacatca aaaggagtgt ttttgctgga attagaggat gggatggaag 120
atggggacac cacagatgaa ttgggcatct cacttcatgc tctcattggt attgactatg 180
gagaaacaat gaaactgcat atttccatca atggtacagc tatggtggct cttgtggact 240
cgggagcgac acatactttt attagggaat acttagcaac taagattggc atgccagtgc 300
agccatgttc ggggctatct gttaaggtgg ccaatggtga caaaattacc agttccggca 360
tttgtattgg gcagcagatc atcatcgaca aggaacaatt caacatgacc tgctacgtgt 420
tacctcttgc agggtttgag gtcgtacttg gagttcaatg gcttcgctca ttgggaccaa 480
tcctttggaa cttcagggac ttatctatgg cgttctggca caatggtcgt tcagtacgtc 540
tagcaggaat tggaggttct gagcctcatt gcacttcatt acaaacaacc aaggatctgc 600
tggccactct tctggaatcc tttgctgaca tttttgaagc accatagggg ctgcctccga 660
tgcgccggca tgaccatcat atccggttgc tgcctggatc attgccggtg gctgtccggc 720
cctatagata cccccaattg ctcaaagatg agatagaacg acaatgtgat gatatgctac 780
agcaggggat catttcggga atgcaacttg ctttt 815

<210> SEQ ID NO 16
<211> LENGTH: 815
<212> TYPE: DNA
<213> ORGANISM: Zea mays

<400> SEQUENCE: 16
aagagctggc agccaagcgt gttaacgggg aatgctacca ctgtactgag aagtacagcg 60
cagatcataa gtgtacatca aaaggagtgt ttttgctgga attagaggat gggatggaag 120
atggggacac cacagatgaa ttgggcatct cacttcatgc tctcattggt attgactatg 180
gagaaacaat gaaactgcat atttccatca atggtacagc tatggtggct cttgtggact 240
cgggagcgac acatactttt attagggaat acttagcaac taagattggc atgccagtgc 300

```
agccatgttc ggggctatct gttaaggtgg ccaatggtga caaaattacc agttccggca    360

tttgtattgg gcagcagatc atcatcgaca aggaacaatt caacatgacc tgctacgtgt    420

tacctcttgc agggtttgag gtcgtacttg gagttcaatg gcttcgctca ttgggaccaa    480

tcctttggaa cttcagggac ttatctatgg cgttctggca caatggtcgt tcagtacgtc    540

tagcaggaat tggaggttct gagcctcatt gcacttcatt acaaacaacc aaggatctgc    600

tggccactct tctggaatcc tttgctgaca tttttgaagc accatagggg ctgcctccga    660

tgcgccggca tgaccatcat atccggttgc tgcctggatc attgccggtg gctgtccggc    720

cctatagata cccccaattg ctcaaagatg agatagaacg acaatgtgat gatatgctac    780

agcaggggat catttcggga atgcaacttg ctttt                               815
```

<210> SEQ ID NO 17
<211> LENGTH: 689
<212> TYPE: DNA
<213> ORGANISM: Zea mays

<400> SEQUENCE: 17

```
cttgcatgcc tgcagcacat cacaatgcag ccccgtcaga gcgcgtcgtc gggcgatagt     60

atagatttgt cccggacgga cggacgggac gtaccggcgc gtagttggcg atggtcttga    120

ccccgccggt gccgccgggc atcgcgcggt ggaactcgtc atgcaccacc aggttgatgg    180

gcgccaggcc ctcctgaaaa aaaaagaaca aaaaaaaaac aaggtcgcgt ctcgttctct    240

gttcagcagg aacggaaccg gtgtggcagt ggaaactaac tgaccttgaa gtagttccca    300

acgggtgcgg cgtagatgag gaaggtgtac tcgggggccg gagccagccc aaggatcggg    360

ccgctcccca cgagcagagg ccggaggtac agggctccct tcccctgcgg cggcacctgc    420

aaacggaacg catggcacgc aaagtgatcg ctggtcggcg ccggcgcgtg gctggggcgg    480

ggcgggcaaa cagcggaacg tacgcacgta cccagcgcct gttggcgagg actgtctgcc    540

tgacggcgtg gacgaactgc tccaccgacg gcgccggcat gcacatgcgc tcggcgccgc    600

gctgcatccg ccgcgcgttc tcctccggcc ggaacagcgt gtacccggcc cggtccggcc    660

gccggtacgc cttcattccc tcgaacagg                                      689
```

<210> SEQ ID NO 18
<211> LENGTH: 682
<212> TYPE: DNA
<213> ORGANISM: Zea mays

<400> SEQUENCE: 18

```
ctggagtatt ggactcaccc tggcaagcat cgttatgact ggagaggggt ggcgcctcga     60

ggcaattact tagccaattt gctgaaggtg cgcactccga acacagccat gtcagtgcgg    120

gtgaaaggaa gctcgtttta tagaaccttt ttttgttgtt gttgttctgc gatgcaggat    180

ctggatgtgg ctatgaagaa atcaactgca aggtggaaga ttgtggttgg gcatcacacc    240

atgaggagtg tgagtgagca cagggacacc gaggagcttc tggaattact acttccagtc    300

ctcaaggtta catttcagaa gctatctcaa actcaatcgg tttcaacttt cagaaaggtc    360

cataataata acactgtttc tgtgggaaaa aaattcacac cgttcaggac aatggcgtcg    420

acttctacat caatggacac gatcactgtc tggagcacat tagcagcaga gacaggtaca    480

agcaccatac gatacagaga tgaattcaag taactttcag tccgtttcca agatactgaa    540

ccttgtgaaa ttgcttcttc tgtctcagtc cactccagta tttcacgagc ggaggcggtt    600

ccaaggcatg gagaggagtc ttccatccaa acaaggacaa gctccgattc ttctacgacg    660
```

ggcaagggtt catgtccctc ca 682

<210> SEQ ID NO 19
<211> LENGTH: 458
<212> TYPE: DNA
<213> ORGANISM: Zea mays

<400> SEQUENCE: 19
actaagctgt acatggacag cctcaaggag cccggcgact cggggaagcc ctactccgcg 60
cggtacatcg gcagcctcgt cggcgacttc caccgcactc tgctctacgg agggatctac 120
gggtacccca gggacaagaa gagcaagaac ggcaagctgc ggcttctcta cgagtgcgcc 180
cccatgagct tcatcgtcga gcaggccggt ggcaagggct ctgacggcca ccagagaatt 240
cttgacatca cacctacaga ggtatcaaac tacttgatct tgaatgtaga actgtgtcca 300
gctgatagat taaccagttt gcgtcgtgca gatccaccaa agagtgcctc tgtacattgg 360
gagcgtggag gaagtggaca aggtggagaa attcctggct tgaatgccag agcctctctc 420
atcagatgga ctcccgaaga catcaagttt agggagga 458

<210> SEQ ID NO 20
<211> LENGTH: 430
<212> TYPE: DNA
<213> ORGANISM: Zea mays

<400> SEQUENCE: 20
gggcaagtag tgctggagtc catggcttct ggagtcccag tcgttgctgc tcgtgctgga 60
gggatacctg atataatacc gaaggacaag gagggtaaga caagctttct gtttacaccc 120
ggagatctcg atgagtgtgt gaggaagata gagcagctcc tcagttcaaa agatctcagg 180
gaaaccattg gaatggctgc cagagaagag atggagaagt gtgactggag ggcagcctcg 240
aagaaaatcc gcaacgagca ctacagcacc gcaatatcgt actggcggaa gaagatgggc 300
aagactaact aggcctcctt gtttccggat tcttctgtcg ctgccctctc caactagttg 360
ctgttaataa ctaaagaatt tgtacattgt acccaaacag cttgcgagtt ttgtgtggct 420
agctgcattc 430

<210> SEQ ID NO 21
<211> LENGTH: 777
<212> TYPE: DNA
<213> ORGANISM: Zea mays

<400> SEQUENCE: 21
agtacgtcac ttacgatgtt gttgtccagg attcattgtg ttcattgctg ttgtttgggt 60
catacaagaa tttacatctt tccatgttct gaaatatgtg atcttattca taggtgagac 120
agaagatgtc gtacaatcat gttctcttta ttttaatttc tggaatgcaa attgtatgct 180
tgaaatttaa tctttatgtt tatttatgtg caacaggtgt gatgaacagc ttattttcag 240
tttacggtaa agaaacaaaa aaaacctttt ccttattatt ccatgctaga ataatccatg 300
tgttactctc aatgaaatat tctcaaatta tatagatatt tatgatgact tgatatcccg 360
aagagttaac acaagtgatg ctgaaaagtt tgctgaaatc tgcccttgcc cctgcaatgg 420
ttttgcatgg ggtgttatat ggtctgctcc aagtttcgat agttatattt ttctgtatac 480
cttgatgatg tgttaagata ttcctgatgt aacgacacca atgctaacgt tttctgttct 540
ttgtttcagg ggattcatct cgtttatctt tctctgcgct tcaatatacc ttggactggt 600
catattgtct tgaggtgatt cctatgtttt catatcactg catttttatt ctccttgtgg 660

```
tgacatggta gttcactgtt gcactgcaac acagaacaca atcacacagg tgctactaac    720

ttagttgtta ggaagacatg tcccagaact aaatatacat tgcaacattt tgggctt       777
```

<210> SEQ ID NO 22
<211> LENGTH: 810
<212> TYPE: DNA
<213> ORGANISM: Zea mays

<400> SEQUENCE: 22

```
tctattccag cctcctcctc cgtactgcgc gctacctttt gctcctccgc cggcttcggc     60

tcgtcttctc cgtcctccat attcggcgac gccaccgagg tcgccaacgt gccaccgctc    120

accacgccca acctcttcgt cagtggtaac gtctctccgc ttcgccccgt cccaccaaac    180

tcgtcgcact aatacaaaac aggtgtgtgc gtgaatttaa agctgcgggc acttggatac    240

cttaatgcta tgtttgtgag caatccattt ggggaactag ggataaccac taaccagtaa    300

gctttatcga tgaagcacag catttaaacc tgttacagac tcctagtttg catcccatcc    360

tgcagtgttg atgtcagagg ttggcaatgg tgcgaatact ctttttttggg tggataaatg    420

gattaatggg aaaaaggtag ctgatatagc accaagattg ttctgcacca tatcaaaaag    480

aattgccaat aaaagaacag tgcaagaggc aatggacaat aggagatgga ttagtgatat    540

taggggcgct ctctcagcag gggccttgat tgattttttg catctctggg aagctttaac    600

ggatttccaa ctgcatcctg atattgaaga cagacacatt tttaccatag cgccagatgg    660

taactactca gcaaaagttg cttatgaagg gctcttccag ggatcgtgct cctttcttca    720

ccacaaaaga atctggaaat cctggatgcc acccaagtgt catttcttcc tgtggctggt    780

ggcacatgat aaatgctgga ctgctgatag                                     810
```

<210> SEQ ID NO 23
<211> LENGTH: 851
<212> TYPE: DNA
<213> ORGANISM: Zea mays

<400> SEQUENCE: 23

```
cttgctcgcc tgcaggaggc gacgtgcggg ttcgacgagg gcatggtgat cggcgtgggc     60

gggttcggga aggtgtacaa gggcacgctg agggacgaga cgcaggtggc cgtgaagcgc    120

ggcaaccggc ggtcgcagca ggggctgaac gagttccgca cggagatcga gctgctctcc    180

cggctgcggc accgccacct ggtgtcgctc atcggctact gcgacgagcg cggcgagatg    240

atcctggtgt acgagtacat ggccaggggc acgctccgga gccacctcta cgactccgag    300

ctgcctcccc tctcgtggaa gcagaggctc gacgtgtgca tcggcgccgc caggggcctg    360

cactacctcc acaccggctc ggccaaggcg atcatccacc gtgacgtcaa gtccgccaac    420

atcctcctcg acgacagctt catggccaag gtcgccgact ttgggctgtc caagaccggg    480

ccggagctgg acaagacgca cgtcagcacc gccgtcaagg gcagcttcgg gtacctcgac    540

ccggagtact tccggcggca gatgctgacg gacaagtccg acgtctactc cttcggcgtc    600

gtcctgctgg aggtgctctg cgcccgtcca gtcatcgacc cgacgctgcc ccgggagatg    660

gtcaacctgg cagagtgggc cacgcagcgg ctcaaaaacg gcgagctcga cagcatcgtc    720

gaccagcgga tcgctgggtc gatacggccg gagtcgctca agaagttcgt cgacaccgcg    780

gagaagtgcc tcgcggagta cggcgtggag cggcccgcaa taggggacgt gctctggtgc    840

ctcgagttcg c                                                         851
```

<210> SEQ ID NO 24
<211> LENGTH: 1092
<212> TYPE: DNA
<213> ORGANISM: Zea mays

<400> SEQUENCE: 24

```
cagaaatatt atcttcacat tcgctcataa aatataggtc agcaaacacg cacaccaaat     60
caaataaacc agatctatac atcactcaac ttatattctc tgacagtctg aaaatataat    120
aatttgttta caatcataat atatattata atattataaa atcatatata taatttataa    180
atatttataa aaaattttat ataaacgata aaacacaaca aaaatataca tttctaataa    240
caataacatt attcaggtta aagatatgct gttctgctca catcgcagca tagttgacac    300
atcctgtgct gtaacctgca taaggtttgc cacgggatca catcagaatt gagccatcat    360
ccaacaaact gcagcagggc gtaaaagata gtttgatcag gcaatgaaac ctcctcacct    420
ggaagctccc atcaccaatg aaggcaatca cacgcttgtg gttcgcaccc tgagcatatc    480
cgagcaatgc acccactgac catccaatcg aaccatactg catttggaat tcatacctgc    540
agcatgcaga cagttctcat gagaacccag gaacagaaca gagttcaaga gaaacaaaca    600
gaacagagca ccatcagaat gctcacccac agccttctgg cagcttaagc ttctggcagt    660
tgaaccagga gtcaccagtc tcagcaatca ccgcactatc accagtcaac atcttctgga    720
cgtgcttgaa gagcacattc actcgcagtg gctcatttgg ctcgctttcc agcggctggc    780
cctcaggtac aaagatcctc ttgtaattct cataggcagt ggtgttctta ttaaccctct    840
tagccaattc agacaagaac tctttcatca tacaccatcc cgatgattgt gtagtatcat    900
tcattttttt gtgtttgttt tttaaatcaa atttatttct tatataaact catttttctat   960
aaggtatggt ttcggcgtgt caaacttatt gttttgtgtt atgtttcggt gccggtcgtt   1020
tggttgactg ggtgttgaat gttgtcgaat gtactttttg agatatacca aatataacat   1080
aactatacaa ac                                                        1092
```

<210> SEQ ID NO 25
<211> LENGTH: 611
<212> TYPE: DNA
<213> ORGANISM: Zea mays

<400> SEQUENCE: 25

```
ccatgtgcta tcctacatct ggctaagctt ttcctgtaac ctaaaccgat ttaactttgt     60
agaagaacat cacatcaagt gacctctatc tccatgatgc gatcgtctct ttgaagaaaa    120
aaacatatag gctggaattg gctaccttgg ccagccagtt atccaagtcc ctctgcaaaa    180
gagaacaaag acaacaaaac tgtcacggag ttgtatcttc tggaaaatcg aacagtcaca    240
cgtgattaac ttctcatgca ttcaaagcag attatcactc catttctgaa caataacagt    300
cgcttatgga aatttgaatc gtctctgttt gctagaggtg agacaggaga tttcagcagg    360
ggtaagcttg cataatgagt agtttcatca gaaagatcag cattcctaca ctactacata    420
ccaaacgata tgagcaacca attcgatgcc cattctagaa attaagaatg tctagccaaa    480
tcgagtgatc atgtgttagc tgatattctc atagtgaagt ggaaatttct agccgcgctg    540
cctcacaatt ccaacatgaa ccaaccatta tcgaacgtga atcccgcaat aatcatttcg    600
tgacctggtc c                                                         611
```

<210> SEQ ID NO 26
<211> LENGTH: 858
<212> TYPE: DNA
<213> ORGANISM: Zea mays

<400> SEQUENCE: 26

```
agtgctgatg acaccagcgt agtctgcggg aagggattgt gcacgaggca ggcgacgctt     60
ctgccggtct agatgcagct gatctaagcc gaaaccagtg ggaggactaa ggagggtacg    120
tatctggctt tctgctgcat accgcggcgt tgtttttgcg cgcgctgctg ctttctctgc    180
gctgtttcca ttccagtccc gagtcccatt ctccaacccc aaaccccaat ggcccaatcc    240
caacgcggat agcgagcgtc atgggtgtgc agtgtgctcg taaagtcgtt ggggcctgat    300
cttgagtacg gctaggtata gatataaatg gtactgatat tatttgtctg tatttgaatt    360
tgaaccgtct aagagggcta aaacccgatc tatatttcga gttcgagtat tagtagccga    420
tccgtatcag aattatatct gtacactcaa agttagatat ttaagatttc gatattaatt    480
ctaattttat ccgacacaac tcgacaatat ctgtatccga tctgaattcg aagagaaaat    540
atgaaaacaa atatgttaca agtactatcc gtccgtatcc attacactcc tacggctacg    600
ggtgtcaatg agttctaaat tatgaagaag catttagatc gtggtttatt acctcctcta    660
agtacggctc aaccactatt ggcgtggccg taagtgttag accctgttcg atggttcgtg    720
taaaatagag tatgtctcgt tgtagatgac attatttgat attgtttata atttgcagag    780
taaaccttta aatagaggaa gatatatatg agctgtttga gacggagcgc gagaggaatg    840
tcgtgttcca ggtttagc                                                  858
```

<210> SEQ ID NO 27
<211> LENGTH: 1264
<212> TYPE: DNA
<213> ORGANISM: Zea mays

<400> SEQUENCE: 27

```
gttgccccag tagttaacat tgacaggtac tactgctgct gcagagcact tcattttgca     60
acttgaaaag gttgagataa acttctgtat tgtgcaaaca aatttataat gttgcaattt    120
agtgtgtata tagatatgtt tttattgtaa ttttgcactt gtcgaatttt atgttatttg    180
ttcgactcca aatttatata tgaatagcct atctatcaag agcttaatgc tctaattttt    240
ctctcccact taggcatttg agtcccccaa cactcatgct gagtgcttca catatctgcg    300
gcaatacgcg gagaattgtt ctgcgaaggc tgcttgtatg gtggcaccta agagcatcat    360
ctcctaccca caggtttcaa ctcacctact cctgctcttg ttttgctgag ctatacgtcc    420
acaatgcgtc gctgctagct tcacactttt ttgttgcttt tcatgacaag ttggtgttga    480
gcattgtcag tattggcact tcagagttta gattggagag gaaggctaac acgttgtatc    540
acgaacacag gtctggaaag ggcaagggtc gaggaagtgg aagcttgacc agagcgacgg    600
gttcttcgtg caattcgagg caccggcgct gaggaagata tggtttgtgc caagcacaaa    660
agagaaggga cggacattgt gcaggtaaat ctctctctcc ctcccccttt tttttcctac    720
ttgacagttc taaagtagtc ggttcagaac tagtttcagc ttccaaaacc agtgtcttct    780
aaaattaaaa tgctgtccat gcgctgccgt actgctcacc ttgttcagac gatcatgctt    840
actagagtag gaccaagacc aacaagtgaa ctgtgcctgt aatcgcaaat ggaaaacaga    900
aacggcaaac cttgtcatcc accttccacc atgaaaagcc tcacgtcctt ccctctttat    960
ggtagtcaca agaggtagga caacgtactg tactgtactg actggagtac atcgcgctcc   1020
ccctctttat tgcccgtgca cgcaggagcc ctgaggcctt ggacatcggc atccatgaag   1080
tgctcccccg tatattcaag gaggcagctt aagcccaata atggaggact gtccatggat   1140
tcctgatcct gcacagcgct tgctggatgt tctccctggg acctgggagg aggaaagagc   1200
```

```
tcgcccgaca tacatttgtt aaccagtgaa tcggctacgc tggcagacgc agactcggaa   1260

gaaa                                                                1264


<210> SEQ ID NO 28
<211> LENGTH: 607
<212> TYPE: DNA
<213> ORGANISM: Zea mays

<400> SEQUENCE: 28

cagtcactac tgtgcttttg actggaactt gtgtcgtctt atggacatca gagaagaatg     60

atggtagcag gccatctcgt gccatggcca tcaatattct tggctgaagg aagtatcaaa    120

gtggaagtat gaataccaat agcagcataa actgaagttg tgcaatgcat atgcttgttg    180

cgagaacaga taaagcagaa aactgatgat atatatccag attatatgcc agtattcttc    240

agatgttact cattttaaaa ccatgcccac ttggctgatg actcatattt tccatcaatt    300

tgaatcacag aagaaatttg atgatacatt ggttaagata tgcttatacc tgtggcaata    360

tagaccccat caaggttgag cagagagcaa gaacagcacc agttgttaca agatacctaa    420

aacaagataa gcacatgaaa acaatctcag tcagacgcac accagatcat ccatgaaaaa    480

aatgagaaga agtccttaca ttgcccagtg catcccatgt ttggcaaagg cagatgaaat    540

aggggtgtct gggtccatag caaagtatgg taccagacca acaataacaa ctgaaaccaa    600

catgtac                                                              607


<210> SEQ ID NO 29
<211> LENGTH: 1025
<212> TYPE: DNA
<213> ORGANISM: Zea mays

<400> SEQUENCE: 29

ctctagagga tccccctggt ggttgagagg tactaccagc aagtgacgat gtactgaggc     60

cagtagattg ggctggggag ctgaacccaa aaaggttgtt tccagagctc ggaaatgtaa    120

atgaaggggt tgaagcagac tgtaaacctg gtgcagtgga agtactagat ggtgcagcca    180

cagatattcc agcagcatca cttgaaggtg caactgcggt gaaagtaggc gtagatgtgg    240

cgggggaact tgaaaagctt gcaatacttg atgacacagg tgaaataaaa agttccgatg    300

atgccttgct gcttgcatct ggtgcaacag atttcacttc agcttttgta ccccctatac    360

caaatgataa ggtgctagtg ccatcagatt tagctgatgt taccaatgac aatccaaccg    420

gagcactgga agaaaaacta aatcccgtaa atgcaggaga cgatgaaata gctggactgc    480

tactggatac ggcaaatatg gaagtggaaa caggggcttc atggattcag tttgatgagc    540

ccactcttgt cctcgacctt gattctgaca aattggctgc attctctgct gcatacgcag    600

aacttgaatc tgtactttct ggattgaatg tgcttgttga gacttacttt gctgatgttc    660

ctgctgagtc ctacaagtat gttatttatg ttgctagctc accctttttct cagccattgc    720

tcctcctaga cccttttgtg atgacatcat acttgctgtt cttttgaatg caggacccta    780

acatctctga gcagtgtgac tgcttatggt tttgatcttg tccgtggaac ccaaactctt    840

gggcttgtca cgagtgctgg tttccctgct ggaaagtacc tctttgctgg tgttgtggat    900

ggacgcaaca tctgggctga tgatcttgct acatctctca gcactctcca gtctcttgag    960

gctgttgttg ggaagggtaa tcatgcttgc acttattgtc tgccataaaa ttggatttag   1020

ttaca                                                               1025
```

<210> SEQ ID NO 30
<211> LENGTH: 210
<212> TYPE: DNA
<213> ORGANISM: Zea mays

<400> SEQUENCE: 30

```
ctcatatgct gctttggctg aatattttcc attagccgcc aatctgaaga tatgcttatc     60

ttcttggttt ggatgtaaag aaactgcctc cagaacatcc cagaggtcca ggaagtcagc    120

aagaaccccc actgtcaagg cgcccctaat atccatcgac cattttctgt ctgttagagc    180

ctattggact gttttgcaac tcttgattcc                                      210
```

<210> SEQ ID NO 31
<211> LENGTH: 829
<212> TYPE: DNA
<213> ORGANISM: Zea mays

<400> SEQUENCE: 31

```
acctgctctt tttgcgccgg ctcccggtgg gggcttagcg tggtcgttcc aatgggaata     60

tgatcgttct tatagcgtgt gtggcgcgga ctatctagtt gtggatattt ggccttttag    120

ccttgtaata ggggttgaca aatattgtcc ccctacctat ttttttctcc ttaatgaaat    180

gacacacagc tctcctgtgt ttgttaaaaa acacaccaaa tgactcttag tagcccacag    240

tacacgcgga taaggcaaaa ggttaaaagg attactccac acagattaaa tcaaatgata    300

aagtgggcct aataagcctc tacttgttca agaagtagaa atagaaagac tcactggcaa    360

aagcatgagt attcctatag gaacgacaga cgccaaatct gtcaatgttc tttgaagagc    420

ctgcttttcc ttctgagtta gttcatcccc aataagagct ctttttagca aacccatagc    480

agctcctgta tcaattgcta atagttgtgt cccctgcaac acagtctgtg cagaaaaaaa    540

tatgaataag gaacaagttt ttctttaaac tagtacagtg ggaagtatgg agctaacaat    600

actttgagtg tgtgtttgtg tgagtggtgt ttaggtcatt gtaattatca tccttctttg    660

aatgaaatga tacgcagctc tcctgcgtgt tcgagaaaaa aaaacaatac tttgatgagc    720

ggctttggat tggcaaatag tcttttggat aaagttaatt cgattattca acccccctac    780

tacaatcttt cacaatgata ccatgtcttc aagtgtcatt atcgtcagc               829
```

<210> SEQ ID NO 32
<211> LENGTH: 711
<212> TYPE: DNA
<213> ORGANISM: Zea mays

<400> SEQUENCE: 32

```
tgctactgtt ctgtccttga cttggaaccc cacgggcagg taaaacaacc aggcaataaa     60

attacaatga cgaaggtgac aagagtaaaa ttaccatcca tcatccaaat cgatacgcca    120

tcctttcaag gagatccttg ctatccgagg gagaaaccat aacgttaatg gtccccttcc    180

ctctccagca aacaacggca attgtggagg gatccttaca aatggaatct acacgcctat    240

tccctgaaat accagagaaa gttagattat gaactaactc atggtttctt ttatctttac    300

tcttcaggta gggcataaac attaccttcg agtaacacta caacacagca accgggcgtc    360

aaggacgcag cttgctcccc gaatctggtg tcggtaaaat gagcaaagct tatgcttcgg    420

tactgtacga ggcggtggaa ctcaagtgcg gatgcatata gtatcctctc gctgatggat    480

ggaagcacca gcgataatcc atcataagac aacctatatg cacatggaca gggatccttt    540

gatctatgcc tttcctgaaa cagaacagag tacctcagag tctgagtaaa atatgcaatg    600

ctgaatcttc ctacgagatc ttgaatcggt aagggacacc gcgtgtttag agcgcttaca    660
```

aacattttaa caccaagtga agctatcttc agggggatcc tctaaagtcg a 711

<210> SEQ ID NO 33
<211> LENGTH: 483
<212> TYPE: DNA
<213> ORGANISM: Zea mays

<400> SEQUENCE: 33
ctgaactcta tgatgtgaat tccaaacagg acctaactct gtgatgtgaa attgaaatca 60
aagtgccgac tgccaatgga caggactggt aaagagtttt attgggatcc catctatttt 120
aggtagttga tcaaggttaa gctgcacttt ggtgacccaa gcagccctac taaatttggt 180
aaatttggtg gtagttaatg aatggcaaga tcattgaact caaaagctta tctcagacat 240
gacaactcaa aagcttacct tgaacacgag taccaatcag aatcggtaca agatggttac 300
ctagagagaa ctataaaacg actaaattac cacataaata gggaaacgca ccaccgaact 360
gcactctact caaggtaaag acagtagcag catcatggaa aggttgccaa acatgcatca 420
ggagccactc gcgaaccaaa aaccttttcc ccactccatg acacaaatca agaaacggta 480
aca 483

<210> SEQ ID NO 34
<211> LENGTH: 697
<212> TYPE: DNA
<213> ORGANISM: Zea mays

<400> SEQUENCE: 34
tcccggtgat ccggtagagc caacctgcag gctcgcctcc acctccaccc gctcgatccc 60
tgcatacgca tgcgtgcgtg cgcattgagc catccacgcc aggatcaggt gaaaaaaaca 120
acaacaacac caccgacaac aacaaaggcc cagccgccca ggctttgggt aaagaagaag 180
gagctagaat taaaggacgt ttagaatcca gatccagcag ctctctacac agggagggac 240
gatggcagca gcagctgctg ctgctgcata ccgatcgtac tggaagtaat gatcgatctg 300
ccggccgggg gggccctggc agctggttgg ccggccggcc ggaatggacg gcggcgggat 360
ggggtgggct ttgttgaagc ctgaaggcgc tcatcacgga cgtaacgtac gtacctttca 420
ctttggacag gcatctgcgt acccgcttct catgcaacgc caccatctcc actttcagct 480
ccgtgctctg cgaaacgcca ccagcgatca ggaaacgcgc acaggattgg gttgttcgtt 540
gtcgcaacaa tgctgccttt catgcatctg catgtgcagt gcagtcccag ctagctagta 600
gcttgcgttg cttgcttgct cgcgagagct agttcatcat gcaaagggaa aaggcagcac 660
tgcaggtcga ctgtagagct caccagggta ccgagag 697

<210> SEQ ID NO 35
<211> LENGTH: 844
<212> TYPE: DNA
<213> ORGANISM: Zea mays
<220> FEATURE:
<221> NAME/KEY: misc_feature
<222> LOCATION: (782)..(782)
<223> OTHER INFORMATION: n is a, c, g, or t

<400> SEQUENCE: 35
aagaacggag aggagaagat caacggggag atgttaagag acggaaacca cacgctaacc 60
gcaatgtgga tgggggacac acggcgaaag ctttgcaaac ctgtcaggcg cttcctcttt 120
gttgataagt gaaatgtttt ttgaggagag aagttgaaag aacttggcag catcaccttc 180
cttcaatctc tcgtaaatgt tcgttaggaa ctggttgaat tcctgtggtt cctgatcacg 240

```
gatggcgatg cccagtgtaa acagagaggc aatagctaat ttgctacgac aactgaccag    300

ttttatggag accgagcaag catgctaatg aactaatagt tagcggcccc tctaaccaat    360

agttggcagg tctattagca ggcatgtttt gatccatacc tattaattta agctgctagc    420

tattttagca ctactcatgt aactatcatg agcttttcga gaaaaaaaat gtaactatca    480

tgagtgctta cctgttcaat aatacaggcc ttccgcagag aagcaaaaca ttcaagtgct    540

ttttgatagt tgcccccatc actggagttc tgtaacaaag ctgctatgta attctgcata    600

tctccaatag ccttctgagt ccatgttgag ctagatctct tagcccgcat ggcctcaaaa    660

tcttgaactg gatttgaatc tctgattgcc acaacactct cttgtgaagg atgtggattt    720

ttcaaaacct tgtcctctac agatttagct tgatcacctg caccagtata tgccaacatg    780

tnctgtggtc gtgctttctt tttctgtaat caaaattaaa ccagtcaaac gatgtagttt    840

tttt                                                                 844
```

<210> SEQ ID NO 36
<211> LENGTH: 827
<212> TYPE: DNA
<213> ORGANISM: Zea mays

<400> SEQUENCE: 36

```
gcagatggta ctatctctct ggccgttctg tcttgcgatc ctgatgctgg aactgtgcgg     60

tgtaggtgtg agaacactgc aatgcttggt gagagaaaga actgcaattt gccaggaatt    120

gttgtggatc ttcctacatt gactgagaaa gataaagaag atattttggg ctggggtgtt    180

ccaaatgaca ttgacatgat tgctctatcc tttgtccgta aggatcaga tttggtgact     240

gtcagacagg ttcttgggca gcatgccaag cgcattaagt tgatgtcaaa ggtttgtata    300

tactatcact gtcgaccttt aaagggttat atcagctata tttctgtcca taatttggca    360

cgactccatt ttttttgttt tctgttgaaa ccatatatgc agaacaatga tttttgtttg    420

catctctcga atgaaacctt cccatcttaa tttttgctgt gaacacatga taaccacatg    480

ttatgttatt tatcatgtaa catatgaaag tagtatgttg agtacccttt taccaactag    540

gatatactgc ttgcccaggc tgcaacttca caagaatttt tactttacag ttggatagcg    600

aaatgcaatt ctgttaactt gactctacat ttccacctgg taggctgctt tactcctaac    660

cgaattctct ggaatactgg ataattcctt tattgtaaaa aaatgggttc tgcctatctg    720

tcaaagctag aaaggtcatc ttccctgatt acgaagcaca agaatttttt gaattctcaa    780

attgctcaga atagttccat gtcatgcatt gcttatttac tgcaatg                  827
```

<210> SEQ ID NO 37
<211> LENGTH: 854
<212> TYPE: DNA
<213> ORGANISM: Zea mays

<400> SEQUENCE: 37

```
tattcaactc tgcgcagatg gtactatctc tctggccgtt ctgtcttgcg atcctgatgc     60

tggaactgtg cgttgtaggt gtgagaacac tgcaatgctt ggtgagagaa agaactgcaa    120

tttgccagga attgttgtgg atcttcctac attgactgag aaagataaag aagatatttt    180

gggctggggt gttccaaatg acattgacat gattgctcta tcctttgtcc gtaaaggatc    240

agatttggtg actgtcagac aggttcttgg gcagcatgcc aagcgcatta agttgatgtc    300

aaaggttcgt atatactatc actgtcgacc tttaaagggt tatatcagct atatttctgt    360

ccataatttg gcacgactcc attttttgtt tgcatctctc gaatgaaacc ttcccatctt    420
```

```
aatttttgct gtgaacacat gataaccaca tgctatgtta tttatcatgt aacatatgaa    480

agtagtatgt tgagtaccct tttaccaact aggatatact gcttgcccag gctgcaactt    540

cacaagaatt ttttacttta cagttggtta gcgaaatgca attctgttaa cttgacgcta    600

catttccacc tggtaggctg ttttactcct aaccgaattc tgttaacttc acatggatct    660

gatttcctta atgatatggt tctgctatgc aggttgagaa ccaagagggt gttgtaaact    720

ttgatgagat cttgagggag actgatgctt ttatggttgc tagaggtgat ctgggaatgg    780

agattccagt cgagaagatt ttccttgcgc agaagatgat gatctacaag tgcaacattg    840

ctggcaacct gtgt                                                      854
```

<210> SEQ ID NO 38
<211> LENGTH: 635
<212> TYPE: DNA
<213> ORGANISM: Zea mays

<400> SEQUENCE: 38

```
tgcagcagta taattttagg gttttagctc tagtagtact catccattca taattctggt     60

ttatatatgt tcaatattcc acatgtttat gagaggacaa ctaaacgtat tttgttgaaa    120

tgaagtcatc ggtcaacaac ataggtacat gttctttcta tcagatggca ttatgaaagc    180

atatttcata gttgtaagaa tgtgaagtcc ctgttgtatt gcataggatg gttacatata    240

tatatataga ctcggaaccc taaccctaat aggtcagcag cccaacagtg gtgccagtct    300

aactacatat ataggaacac acacacactc caacaatagt tgcgtccatg gtaagcagtt    360

tcatgttttt atcagggttc aggatgcttc acatagtggt tctaaatcct gaatttgtta    420

ttaactgatt tttagttact tctccttttg agcagctctg aggcatccta gtttgtatcc    480

gttttcagtt aaccgctttg tacgaaaaca agcattaatc ctatcttgat ttcctttta    540

acttgtaatt tatgtttttt ggtcaattgt catgaatagg catttggctg ggcgtatgtt    600

aacaattggc acaacacatg ggagcagggg tacaa                               635
```

<210> SEQ ID NO 39
<211> LENGTH: 715
<212> TYPE: DNA
<213> ORGANISM: Zea mays

<400> SEQUENCE: 39

```
tgctttcttg agtattttat acttgagtca atttagttca cagcttggag gcttgagttg     60

ttgagcttta gcctgactgg ttggcccatc aaccaaacta ccaaaaaaga gtgaaaattg    120

aatagacttg gccaacccta tatgcccaaa gaaagtaaga tacaacggcc aaaatacaac    180

tacacataga aatagtgatt ggcttattgt cagtaaaaaa acatttgttg ggtggggtac    240

attctccagt ttcaaagtaa tagctcttcc agcaaaaata cattttggtt tagatttaga    300

aacaaaatta aatagtctat caataacttc taaaaatatt cagcttcaga gaatgaaaat    360

tatgtgtaga tccattcatg gtcttagtga tgatgtgata taactttgca cagtaaataa    420

taccaattta acagtaaaac tctgaaagtt tttttaaaca aattagtaat cttcatcttg    480

ttaggcctgg tgcagtggtg agagctgtct cattgagtct ctagatcatg ggttttttct    540

tgaacacgca agagagttac gtatcatttc attatgaaag gaaaaaaata cacagggaaa    600

ggaatcccta aacaccaaga caaactaaca atgtgacgaa ccgaccagcc gtcctgagaa    660

caggtgacaa cgcaacaaca ctagcactag cctctgttcg agacccttac aaaca         715
```

<210> SEQ ID NO 40
<211> LENGTH: 751
<212> TYPE: DNA
<213> ORGANISM: Zea mays

<400> SEQUENCE: 40

```
ggtcggctga tgcagaaaca aataattagg ttacatatgc atgactacaa atatactact     60

catcaaaatg ataacatgaa cagataccaa acttattgta cgcacaaaga aaaaaaatag    120

ttgaactttg cttacctgga tacaaggtat tccaatttct ttgaaacaaa agaagctgct    180

tcttcaggcg taccaataaa atctaaatca gaaacttcaa cggctaatgc tagtgccgct    240

gctatggcta ttgctggagc accacggaca accatgtctc ttattgcatt cctgggtaat    300

atttaggggt cagtataaaa caagcattat ccagtggtat ttataactag ttacatttca    360

atggttgcag taggcctatc accatgggag catataacac aatttctgga aattatgtga    420

ttgtttttc ttctctagtg tgatcaaggt caatccagaa taccgaaatt tctactgatc    480

acagattcaa tatgaatata tgatagcctt gtacacctct attgatgaaa ttaccaaaaa    540

aaaaatgcca ctgttttact tgaacacaaa agtaagccac tgtgataacc acaaagcagc    600

aaaatctgct ttagatttaa gcaacacgaa gaaaattaac agttatcaca agccccaccc    660

aaatcaatta gaaatgtata caaatcaatt gaacaaaaag aagtaacagt tttgaaacaa    720

accaaataaa aagggatccc ttgtcctact t                                   751
```

<210> SEQ ID NO 41
<211> LENGTH: 804
<212> TYPE: DNA
<213> ORGANISM: Zea mays

<400> SEQUENCE: 41

```
tcctcatgga gtgctgaagc tccagcccca caccagaggc tgctggaatt ggacacaacc     60

tccataatag catggataca cgaccttgca gcatcgaaca cacaagcatt cctgtgtttc    120

cgtaactccc aagcatcagc ggaattctac aaaatattca agattgtgct aagctgtggg    180

gtttggctgg agcaaaagct cttaaaaggc tctggcctta atctaggatt tagttcccct    240

gtactttgag gtttggtttt tggtgtttta gctcagtttt ttttagtttc tgctgccatt    300

cattttggcg gcttgtactt ggtctatttt agagctttct gttcttaata tagtgataca    360

caattctcct gcgtattcga gaagaaaaat aactcccaag cgaccaagat gatcaacaaa    420

ttgagacaat gagacctttc ttaaactcct ttgaaactct ctttgacagt ccggctccac    480

caaccggaga aactattagt gtcaggtagg ggggcagcag cctgacagac caaccctatg    540

caaaactgat gcccagacct gtctagagaa catacaggaa actaggatgt gctgaattgt    600

ttcttcagct tgatcacata acgggcatgc tcaggatggg gcagtccatt ttcattaatt    660

gaaaacataa acattttcct ttctttttga aactaataaa ttaaaatggg ttgcttttag    720

gtgatggatt ttgagtggta cagcaatgcc tcaaaattgg ttggaagatt taaataaagt    780

ggcaaattat tctatggggt ttta                                           804
```

<210> SEQ ID NO 42
<211> LENGTH: 506
<212> TYPE: DNA
<213> ORGANISM: Zea mays

<400> SEQUENCE: 42

```
aaattttcag ctctgatcaa gctaaaccgt gagcaacgtt tgccctccaa gcaacaattt     60

cttgtaaagt aataaagatt attagagggg ggtattaacc aaacataata ttggctacta    120
```

```
ctagcctaca gaaaacatta ccaacgtcag aaaaaagaat gtgctccaag acaccgaaat    180

gtcaagatga aacctgaagg gctacagcat aatcaatttg tcgaaacgaa cagcacagga    240

agcatttaca ccatgctcta cacatctgtg aaacagatat ttcatgtaac caaacacagg    300

caaaactgtt ccctcaatca gcaggttcct gcctccacct gcggctttta tttcacactt    360

tatttatggg ctgaatcgac aaagagaccc ctagatccat cacaaatgtc actacattga    420

gaaccaggtc gctagccctg ggaacatgga gcctgccact gccattgtgg gtcaaacggt    480

gtgtgatctt gcctcagtta tgcgca                                         506
```

<210> SEQ ID NO 43
<211> LENGTH: 1005
<212> TYPE: DNA
<213> ORGANISM: Zea mays

<400> SEQUENCE: 43

```
gctccatgct cgagaagcag tgggagctcc ccttcgagga cgacatcatt tccactgacg     60

acgagcagga cgacagggtt agcaaggcca cggtggtggc ggcgcggtcg ggcgtctcgg    120

cgcggcagcg gcggatgagc ggccggcggc ggggagctgg tcggaagagc gttgccatca    180

gcccggagct gatgcagagc cggaaccgca tctacctcag gggcaccgtc agcaaggacc    240

tcctcacgca caagcaggtc atccagctct ccaggaagat caaggacggc atctggcttc    300

agcaccaaag atcaaagtaa cgtttcaatc caagatgcat gcccatcaat tgcacaactt    360

cagataatta gcatttgaaa gctgacatcg tatctcccaa aaccattcaa aatgctctat    420

aggctgaaat gtattaaaca aaagtccatg tagtataact gtgatcaaaa ttgcacgctg    480

aagattgtgg gcgcctaatg aaattacatt ccctatctga ttctgattcc ccgctgcccc    540

caattttgag ttcaggctga aggagaaact ggggaacgag ccatcataca agcagctggc    600

acagtcactg cggatatcag ctcctgaact gcgcgcaagg atgcgcgagt cgtttctcgc    660

gagggagatg ctgacaatga gcaacatccg tctggtcata tccattgccc acaagtatga    720

taacctcggt gtcgacttgg cagaccttat tcaggtgatg gcatgagatg tgtcgaccga    780

ttgaaatgta tctgggtatt ccagctgttt aatttgtttg ttttacactg caaattactc    840

attactttac ctcaaacgtt gaaatggaat gtgttcatcc acgttgcagg gtggtctgat    900

agggctactc cgagggatcg aaaaatttga tgcatcgagg ggattcagga tttccaccta    960

tgtgtattgg tggattcgtc aggttatttg agcagatttt cttgt                   1005
```

<210> SEQ ID NO 44
<211> LENGTH: 1140
<212> TYPE: DNA
<213> ORGANISM: Zea mays

<400> SEQUENCE: 44

```
cttgctgcct gcagggcttc ttgatatact gctctctcag cgtaatctaa gaccctattt     60

tcaggattaa ggcgactgtg tgtctcaaag cccttagcaa cttcactgtt attagaattg    120

gttgcctcaa acgttgaagg cagtacccta tgtgagctag aacctccata tacaatgaca    180

tcatctgcca tataaaaagg ggtaaagatt aatcttacta cagaaaatct acaccatttt    240

ccaatgcttg tgttattgat caaattacat catgtgatgc tagcataccc accatcatca    300

tccactttat gggtattaag tgtactagaa gttcctcttg ccattattga agatgaaggc    360

tgcaaatttc cattggcaat atttgtcccc attctgtttt caccaatatt tggtgacttt    420

ttggtggata aaggcagtgg gagcttgcgt gtttcgctag caacaattgg atgcatagat    480
```

```
tttgatgtgt tgccatttga aaaggatgat ggaaggaccc tcttgttatt gtcatttgca    540

tctgctgtag aactgttgtg cttttccact acgctatcaa ttctactgga agtagaatgg    600

cccggtcgca tagccatata aggatttgca tggggatgaa tcctgtccac tgaaccaaat    660

gtataacgac tactctcagc atgtctacca ttcgtaaggg atgctggaag aatcctgtat    720

tgaccattgt tgttctcagt aggcttagtc gatggtggag caggagcgct cctttgccaa    780

tcttcatcct caaaattgat tattcgtcct tcagcatttt gatcaagcct tgcgattgca    840

gacgctggct ggtcgtcatc atcgaatatt gagccaattg agtcatcatc actatccgaa    900

ataataatgg cagagttttc attcatattg ccagcaagca cgtgcactgt atatgtgttc    960

ttagaacttt gtttttctta gcatgactaa accattcatg aaccaatggt ttgctttcta   1020

tcttacagaa ataaacagca cttccttttt tcagatgatc accaagctaa aagagagagc   1080

acaccaccca tctcagagta gcactcacag ttattcgagt taccctcact gtgggagtaa   1140
```

```
<210> SEQ ID NO 45
<211> LENGTH: 432
<212> TYPE: DNA
<213> ORGANISM: Zea mays

<400> SEQUENCE: 45

aacagggcac ttatgtctcc acgaactccc caaaaatgtc gaggcaccca tcccagaagc     60

ccctctctct tgtttcccag tatccacctt tgtagcaata cgtcccgtcc tcggtgtctt    120

gctcgaacca ccgggatttc cagccattgt cttgaagttt agtagactgc aatgagacag    180

agaacatgaa gaaacaacat gtatggattg tgatctatga agcgagagcg gataccattc    240

tttgtcgtcg ttccaacctc agcttctctg cattcgcttt ctcgtattca ccattctcta    300

ggtggcgctg gtctggtctc agccgtgaat cagtaggtgg aagtttctcc tgaatccagg    360

aatggccaag caattaagga caaaaactta gttaccaaac acttttatgt ggcaatccac    420

atgtagatcc at                                                        432
```

```
<210> SEQ ID NO 46
<211> LENGTH: 964
<212> TYPE: DNA
<213> ORGANISM: Zea mays

<400> SEQUENCE: 46

cttgcatgcc tgcagggtac ggctgttgaa aggatgccac aggttatgta cagaagaccg     60

cacaccaggt tgacgccagg aacccatgtg cgcaaaatgt catgccttgc accgcaccag    120

gatagatttc atacccatcc atatgtccca acacagagaa gcaggagcag agccaccgga    180

agaaccagcc agatgatgta tgattggaag cctcccttct gcattggtgc tctcacgtgt    240

ggctcgagac aactctcctg cttgacatcc ttgttgcctt cctcagaagt cttccgcaac    300

ctcagaacag atttggcttc tggagaagtc atttcagcac cttcagttca acaatatatt    360

taactagttt agcaaaaaca gaagtcatca caagagacac aatatacaaa agttccaaag    420

catattacca tattcaggga tgttcttttg ctcatcatca tggatattac caggtagatc    480

atcagcactt ccagcgaggt ttgtactcgc atcctcttca atctgacata acataaaaaa    540

ggtcagatgg tatcatttac taaaatagat cacccagggc caggatcaat gaagatttaa    600

gaagaaaaca ctgcaaaata gtagcagtac actaacagaa ctagtatcta tggaatatcc    660

tagataccga tcatcactag cataaaaaac agatgtaaat ttagcttctg ggtaacaaaa    720

agaacaatca cctccgcttt ttctgctttg tgctgacttc ctggttcgtc tataatgcag    780
```

cttgatgaat catcagtact aggacgctgg cctttgttaa ggcctgactg tagccgcagc 840
ctttgcatag cagttccctg ttgagtgaat gaactctctg agcttgatct tggagcaggg 900
tgatggcttc taataacaat ccctgttgac tcagcctcat ccccatcaga agccacatcc 960
ttct 964

<210> SEQ ID NO 47
<211> LENGTH: 421
<212> TYPE: DNA
<213> ORGANISM: Zea mays

<400> SEQUENCE: 47
caggtgatgt tgttgcatag aggattttct tatggaacca acactggcag gcacattgcc 60
cacctgccct gaaccaagaa gccgttgcca gccgtacgta cgaggacgat tgcagttgca 120
gggaagatca ggcgacaggt tctcatggat ccagcaaatc atttgaatta caaaaaaaaa 180
aacagaataa atgcacactg caagtcaagt caacgtaaac acgggagtgc ttcgtgtatt 240
atccaaaaag aagaagcaaa gcgtcttccg cgcagcattg tgagcctgcc aggcaaatca 300
cattgctatt gctctcaacg ccgttgttaa acattgggag gtggccagat cttcccaaag 360
agctcctcaa cgcggcgtgc ttggttcacg taccccctcta gccctgaagc aagcagttct 420
t 421

<210> SEQ ID NO 48
<211> LENGTH: 361
<212> TYPE: DNA
<213> ORGANISM: Zea mays

<400> SEQUENCE: 48
aaacagaatc atcattctgt gagccaaacc agtaactatt ttacatgaat aaacacaaat 60
ccaaaaaaat tacttggcaa gctgcgaagt ttgattcgaa gtgaatagga attaggatgt 120
ttatagtcac agttaaccaa cgaactacta gtaggtgcta ctacagagat gccaagtatc 180
actaatcaag gagttacaca atctcttccg ataaccaagg atgcatccgg aaggtgcaaa 240
tattgagcac gatattgcta ccagcgagcc atgtttgagg ttcgaggagg gtcatgctgt 300
ccactgccca ccagcaccat atgcagcagc accaccacca ggctgtggcg agaccccttt 360
t 361

<210> SEQ ID NO 49
<211> LENGTH: 624
<212> TYPE: DNA
<213> ORGANISM: Zea mays

<400> SEQUENCE: 49
aagaaggtta tctatatgtg gacatctggt caacagggat tgcttgcgtt tttttgggta 60
aacttcttgc tagtcattag gttttagtat aacaattccg tggaaactat cttttttttgt 120 agtttggtga tgaataactt cctctcttgc taatttcagg ctgggctcta aagttgctat 180
gtttcggtac tcatctgttg agatctacac tacctgcaaa ccacaaccta ctctccagtt 240
cgtcaacccc atcagacagg attggtttga aggacaaagg aggaatgtat ggttcttttg 300
actgttctgt tcatttactt aagttaatgt acaatggtgc ctgacgctta tactccatct 360
tttaaggttc atgctaaagg tatggcgctt ttctctgggg ttgcaagatt tctacagaac 420
ttgaagaatg aacatcctga tgcaataacg ttagcaatcc attgtggcct tgcattccct 480
gttaaggact tcactgaact agaagagttg ttgataaaag aaaaggccca gtttgaggtg 540
agtatatgca ttctattgac cttggtattt gttctatcta ttattttcta tcgaatttta 600
aatgtattgt tctgcagggc agca 624

<210> SEQ ID NO 50
<211> LENGTH: 1023
<212> TYPE: DNA
<213> ORGANISM: Zea mays

<400> SEQUENCE: 50
agaaagaaat ttggttaata agtgctcatc aattgataat atatataaaa agcacattct 60
ttgttacttc ttcaactaga taaatgaagc ctaaatgttt gccaatgtaa caagtaacaa 120
gaattagtgt aaagcaaatg cattctagat ttcatgtcta gcggtccatg tatatttgat 180
aaagagacaa gctcacagaa aaatatacaa gggtaactaa atatgttgct ttatccagat 240
aataccatac atgcagaaat tttttacagc atgggacctc aatttaaata cagaaacata 300
gcagtgaatc tcagtcgacg taaatggcaa gttgcaaagt gactaagtga gccagtgatt 360
tgatcagaca tttgctagca tctagcgcca caactaaagt tgcgacaatg actcggataa 420
ggcatgaaaa tataaagcct atggggtgta atcaattaat catgctcata tccatcgaac 480
tgcacaaaac caacggtcca acgccactgc ctaactcagc tatctgacac ctcccagttt 540
gtcacacgat gtaatgagga aattaagaaa atttcaatgc gagaacaaat gatttagaca 600
ttagactaat tccccaagag aaagaacact tctgctcaca aacaaaccca caaggacaca 660
acgcagtcca aaagcagatg aaactcggaa gagtaactaa attcaggaac atgcacagac 720
ccaatctaca gctggaacta attcctacaa ttccaccaat gtgaaccctt agaatcgcaa 780
caatgcagaa tgcacacatc cctctctcag gagggtaact tgccaacact cagttagtca 840
agctccaacc aaagcccaaa actctgcctc aaaaatcaag caaacgcaag catgccaagc 900
atcacacctc caccagtcaa caggggagat aacaaacatg gagagggaaa ggtgtgtaac 960
cttgccgcct ccaagtcagc cggctggcct gaaaccctag gcaaccaagc accagcgcca 1020
cca 1023

<210> SEQ ID NO 51
<211> LENGTH: 710
<212> TYPE: DNA
<213> ORGANISM: Zea mays

<400> SEQUENCE: 51
gctcttgctc ctcctctgac caccctcccg gcctcccctc gctcaccatg aagatgaaat 60
gaagctcttg tactgtaagg ttcactcact gacggtatag tccccaactc cccatgcgta 120
gcagcggtag taaaaccatc catcatgccc agtggggacg gaaacatgta cagaatacag 180
atacagactg gatccgttta cgtatagatt acgacgacca aaacaggctg ttcatcgttt 240
gttccatgaa cattgtttct ctcacttctg taccgtatgt gtgtactatg gattcataga 300
tctttcatga tgatgatgag gaggaggagg ggacgacaat aggagccggc ggcacggagt 360
cctccagcgg ccagcactcc cagtcgccgc tcttgttctg cgacagcgag aagtgcttgg 420
gcgtccacac ctcccctctg tcgttcctct ccttggcgaa cctcctcgcc gtgtcctcca 480
cccgccgctt cgcctgctgg gctgtctccc agtccttctt caggatcgcg ttgctcacct 540
tgccccagac cacggtcgac tccgaggccg acacgccctg tgaattgtga tgtgacacga 600
tccatcattt gatccatgac atgacatgca tgttcaccat caaccaccac aatcagcatt 660
agatccatgc tacctttttcg tcttgcacca cgggcgtggc gaggtcaccg 710

<210> SEQ ID NO 52
<211> LENGTH: 770
<212> TYPE: DNA
<213> ORGANISM: Zea mays

<400> SEQUENCE: 52
ttttgatgcg ttattaccag ctgtgagtca aggaagactt gtgcaagggt cgggtcatgt 60
gttgtgttgc agactcaaca accacgccac caccggaatc aaatgctagg aaagatgtgt 120
cctgctactg gctgtttaga agggaccata tggacagtgc agaaatgaac aaccgtatga 180
acacattacg gagggattac cccaaaggat aaggcttacc ttatcgagcg aagactgcac 240
ctgttggatc gagcttccag tgtggccatg agcactcata aggacaccac cctttctctt 300
gtccttcttc aggaaaaggc ggaaagttag gatagattcc tctaacagtt tgatgaggtc 360
gtgcgccgaa atcgctggct ccatctgatc gtcggtgttg tctttcctat ctgcgactga 420
atcgagagaa aggaaatgat aagcagaata atagtattaa caaacgttac cgagcgtgaa 480
tcattccggt atgcaataca aacaaccgat caaatacgta acactaaaaa cagacgttag 540
gacgccacag atttggaaac ctagtaaaag aaaaggaagc ttacgcacgc aaaagagtaa 600
ctaagagatt cgtgacagaa tgaaacaaag atatagctgt gtttactgtg ctactgcact 660
cagtaattgt ttctttactg tagaataaag tacaatctat tgcatgattc ggtatgggat 720
tataagtacc ccacattaaa catgttgcag cagtaactgg aaagaactca 770

<210> SEQ ID NO 53
<211> LENGTH: 799
<212> TYPE: DNA
<213> ORGANISM: Zea mays

<400> SEQUENCE: 53
acttctcata cctctgcatc ccgttcgccg acctccatgc actacacggc gtgcagaacc 60
atttacctct cgggacagaa ctgcgcggtg gatccatgca gtaagtgtgg taagcttcgt 120
cacagccatc acacaacact attttctcgt cgtccttgtt cttgaagcag cgtctgcaca 180
ggcaagatgg gcagtaccag cattttagat tcctctgctt ctcgcttgca atctggcttt 240
ctttcaggca cagggcatga tagaacttga aagaacagta gccatgcccg cataccacaa 300
acttcttgtt ctcatcttca cacgtgccac aaagcttgca caagtttgct agagcagtta 360
tcgagaggtc tggttcactg tcttcgacaa tgcttgacac tgagctctcc tgtgttttga 420
cggccaattc aggttcttcg gcaggttctt ctggcttctc cacctcaagc cactcgcata 480
catcgcagcc ttcatgtgct ctgccatggt tgttgctctt taaaggtacg tccggttcga 540
cgcaggtggg acagtaccat tttgctgggg cctcttcatc aatggcaagc ttgagacatg 600
aaacatggta cacggcttca cacctatcac agataattct ttctttggtt gtctgccttt 660
ctaccacaaa tccttgcaaa ttcccattcc gatcccaaaa tgtcccaatt tcggtctttg 720
ttatccgtag aaaatagccc agaaatccgc atgggggga gttggaactt tccctttagg 780
ggctttggcg gggtggact 799

<210> SEQ ID NO 54
<211> LENGTH: 626
<212> TYPE: DNA
<213> ORGANISM: Zea mays

<400> SEQUENCE: 54
caatcttgca tgcctgcagc agcagtggtg gagaatggga caacattgtc tttggccgat 60

```
gcccgatggt gtgtccatgg gaagagggta agggttgggc agaagcattt aggtagagga    120

ttggcgctct gataccatta aattcaggat atagctcttg aataatagat tgattagaag    180

tatacagtac atgaatatat aggcaaggat tccttgggtt tggtttatag aagtatgacc    240

aatcatctat caagaggctc agggcctgtg gccatgggcc caaagggcac agtccgctaa    300

gcctaacagc tgcctaacat actaaattca cagtgaattg ttaaaaatat atcactagac    360

catttactct cttttgtgaa caagttgtcg attcctcttt gattggggtt ttatattgta    420

attgcttttt gatcaggatt ttatattgta atttagattt catctaaact atcgtgcagg    480

ctgctgtcct caaggaaaat atgaacattg atttgcgtgt catgggaata gctggttcta    540

ggacaatgct tttaagtgat atgtaagtga aaaagtggtg gttttcccct atggcatttt    600

acatatgtaa ctctactttt atctgc                                         626
```

<210> SEQ ID NO 55
<211> LENGTH: 759
<212> TYPE: DNA
<213> ORGANISM: Zea mays

<400> SEQUENCE: 55

```
aaagtatcaa aacttgaaag caaatttgat acacgctgat attcgagtgc accaccaaga     60

atcaagattg gaggcttttc ctttttgat gacatacgcc ggtgagcaac attcttctta    120

caaacaactc cttttacaac gaaactgcaa ataaaggaag atgtataaaa ccaaaaaaaa    180

agaactagtg gaaaccaaag aaatgcacag ataaatacag tatgaaactc aaaacgtaat    240

agatcaataa aacaaagaaa gttcacatca agtgtcatca actatgtctt tctagtatga    300

attacaaagc ttcagtttca attaacttaa ggttatggat gctcaagcat attgatgtaa    360

aatcataaag gcatatgaag gtaaatagtg atgcatggaa attggaaaat agatttgttt    420

acctttcact tgggtgacca caagctaagc atttcacctt aacatagcca ccagggtcca    480

tctgaccgcc tttgctggtg gtatctggct tcaaaagaga tgcagcttcc caagacagag    540

aagtaactat atctagccaa ctttctttgc cactcccatc aactaatggt accttttcag    600

cctgaagaag ttgagaaact aacgcccgaa agtggccatc aactatgtct ttcatggctt    660

tcttgtgttc ctcagctgac ttatctctac ttcgacagtg cccactgcca aagctgtttg    720

agcgtagata tccccactct cctgtagcat ccaccccct                           759
```

<210> SEQ ID NO 56
<211> LENGTH: 837
<212> TYPE: DNA
<213> ORGANISM: Zea mays

<400> SEQUENCE: 56

```
cgcgatcctc tatatcgatc tgcagttttg aatataaaat aaattaaggt ttaatccata     60

aacccatccg aaatttcaca caggtcgcaa aattgatcga tatgaactga gtttgataag    120

caacaataaa ctttgcgaac aggggcacat gcgcatagca caccgtaact tattttgtca    180

ccatatttca tataataagc agacacacta ccaaggtaaa taattatatg aatctcagat    240

gaatgagata gtacaatgca taggtcatgg cttagtggca gactactttt tttgctcata    300

gagtcaggct caaggatgct ggcagacaat aatattaggt gtcactaatg tcaaggtaaa    360

tatcttctaa gtaaagtaga tatgtaaatg ctatggcatc aatctgccgc tttaaataaa    420

ataacaataa ttcaagaatg ccttggtaca catcaatttt tatgtcctac ctggtttgaa    480

gaacacggat agaccaaaat cgattgcttc tattgacaaa tcatcttctt tatccaagtg    540
```

```
gaggaagttt tctggtttca gatcacggtg cataaccca agtgaatggc acatagccac    600

aagactaata ataattctta tgagctatgt agccctctct tcgctagaat gccctttctc   660

ctgaaatatt ttcaaacaaa gtgttcagca attgccagaa taaccaggtt ccaaatgcct   720

gttcgagtcc atgaaatcgt ttggcaagtg gaactgcact cagacatgct gagttttttt   780

cacaggcgtc ggaagcaaag caagttgtgc attcacatga caccctacat gatagtt      837
```

<210> SEQ ID NO 57
<211> LENGTH: 895
<212> TYPE: DNA
<213> ORGANISM: Zea mays

<400> SEQUENCE: 57

```
ttgctgccgt agctaagagc tctctgcatt gatcaagggc gacgttttcc tctcttgccg    60

tagccgaaag tcccgaaacc aaacatgtcc tgtcttcgac ctggcacgca cgcatgtcct   120

agcgtcaata acggcagcaa ggacgtcctc ccatcttcca ccaaaccatg tagtactaat   180

aatataaaca gttcatagat tatagttgtt tccttttaaa catatataat tagtttacaa   240

tgattctgag gctcgttcca aatcatcata gtagagacat actgtggaag aaccgaaagc   300

taaaaaaaaa cccaaccttc gattgcacgt agtagataga ggaactcaga gcttgcatga   360

catcaacggc tgagcttata gcgttcctga ctgcaattcc gtcagcctgc tcacgcagta   420

gcaatgccat tattatatat atcctagtag aaacaataaa gaccactgtt cattagttgg   480

aagatgtttg tttggcacac acctgtgctc ctgatgtgac tggaaggcga agcgtgcttg   540

ctttgagagc ctccgtcgcc tcaactagtg tgccattgca ttcttcttct agtgcaggcc   600

attgctcaag gtaacaaatc tgaatcatac tagtgtatgc atggtcagta aaccgaatta   660

tgggagaaaa caaggctgcc cataaggttt ccacacatat atatctattc aatatggttg   720

gttctttcca ttatctaaaa aacatatatt tattaatatg gttttttttc aaaaaaaaaa   780

tgtctatgca tgggtcctcc gatcctaaac aggtcgagat gcaaaaacaa agtgactggt   840

ttctgaatat tgcactgcac ctgctctgtt agaatgtgat acagcttcac ttgtt        895
```

<210> SEQ ID NO 58
<211> LENGTH: 408
<212> TYPE: DNA
<213> ORGANISM: Zea mays

<400> SEQUENCE: 58

```
tgtcgacaat cagccccaaa gcttcgtctg tcagttcacg gcagaaggaa agatccagag    60

cctccaatga aacataacac ttgcgagaaa ttgcaagcgc agtaaggtct ccaacctaaa   120

tgaaatgcgt cagatgagaa ctaattatga ggtggacatc accaaaattg gtcaaggaaa   180

cagcacgtgc taacaaactt aataaaattt cccagtcaca tcgagaagaa acaaacaaaa   240

taaagagaat ggcagtttag gttgttatgt acttcaacca acgatcatgg cctgtttgga   300

tttatggatt tactaaacct ggcatcgcta actattagca ccagggccca taaggctcaa   360

gtgcaagtgg agagcttgaa caaggcacca aaaattctag ggtcccca                408
```

<210> SEQ ID NO 59
<211> LENGTH: 749
<212> TYPE: DNA
<213> ORGANISM: Zea mays

<400> SEQUENCE: 59

```
ttgaggtgga caaactacct gaggccggac atcaagaggg gcaagttcag cttgcaagaa    60
```

```
gagcagacca tcatccagct tcacgctctt ttaggcaaca ggtgagtacc aatgaaatta    120

gtcaactcca gatcgttaca aagtgatcct ttggcttatg tatcttatct gccctctttc    180

tgctaagaga agactgctgc cagccactta gtgacaattt acaaattagc aaagagaaga    240

aatgatagcc agtgtattta tactgaatta gaaacgattt tctagtgcat ttgtactttt    300

taatctgcca tttcatctcc ccttccttca caacgtagaa tttcggcaca catggtatat    360

tggtagatga aaacaagatg ttaatttcaa agtatacctt tgtttcatgg tactgtttca    420

ggtggtcggc cattgcaaca catctaccaa atcgcacgga caacgagatc aagaaccact    480

ggaacacgca cctcaagaaa aggctggcca agattgggat cgatcctgtc acccacaaat    540

ctacctgtgg cactctcact ggcaccacga acgacagatc agccaaggcc gcggcaagcc    600

tcagccacat ggcacaatgg gagaatgccc gcctcgaggc tgaggcacgg ctggctcgag    660

aatcgaagac acgaacagca acaccgacgc catctgcact ccatgcgcag ccaatggatc    720

tacctgcctc tgctggttct cctggcttg                                      749
```

```
<210> SEQ ID NO 60
<211> LENGTH: 966
<212> TYPE: DNA
<213> ORGANISM: Zea mays

<400> SEQUENCE: 60

gtgaatgtga actcataaaa caaagcttac tctttgaagt gctgaaagca ggtccatttc     60

agctttccgg attttgttag attcatcatc atcagcttca tcctttaaca acttagcttc    120

aatgcatgga tcttgaagct tctcatactt ttcttcatgt acactgggtt cgtcttcctg    180

tatgatacca tccatccgat tattttggtg tttccatatt gagtaatagc attaccatct    240

tcttagttgt aaaatgctag caacatacct gattatatgt tgatgctagc aacaagtagg    300

tgctatcagg ttcctgagtt gtaaaatgca ccacttgtgt tgtttcatgt gtatcgccaa    360

taactgaagg tagagcagca gtttcagaga agctgacagc atcgtcagtt cctgatgacc    420

cgtaaactat cattctccaa tctgtgttat catcgcagtg gaaaatcagt gtgactacct    480

tcaaaatggt tgcatggctg aaagaagctt cattttgctc acatagtaaa cctctccttt    540

ttgtagacat gtatcgcatg tgagagtggg tgcttttcca tgatccaaaa atggttgctt    600

tgatttttgg catctatcta aaaatggttg gtttgggtgc aaaccctagg tttcatttat    660

catattactt tgagcatagg taaataatta atacaattga ttacaaacat acataagctg    720

taatgtcttg aatttatttg taagcatcac tagtcactga tgcctaaaat tcatgttaga    780

tgacttcaca actaaatttc aatctcttag gcattctatg aaaattttat atgtgagtac    840

ataatatttt gactaaatta tttgaggcaa agaactacat aacttttttt ttgcaagaat    900

tacatctcgt ctgtatattt aggatagtca cctccaaaaa gataatccca ttccgtcatt    960

tgtgcg                                                               966
```

```
<210> SEQ ID NO 61
<211> LENGTH: 778
<212> TYPE: DNA
<213> ORGANISM: Zea mays

<400> SEQUENCE: 61

tggtgaccat gtttactttt aaccaaggtt aggggcggca aatgatttga aatcgaggtc     60

caagcaatag cgtacacaga taaggttagg ttccccctgt atttactagt cagattaaag    120

catccttgtg gagttggggt tgtgggccac aacaacccac caatacagca gtggaaggaa    180
```

```
ggaggagcga gagcagcggt gtcgacagta ccttcatctt ggatttcttg gcttgcagct    240

tcttggcctg cttctccttg gcctccttct cccctgcaca ccaccaaata tcgattccaa    300

atcaaggcga cgatcgaaat tggacatgca agggaaagga ggcaatacaa gatggaatcg    360

tacgttggag gtcgaactcg tactgcttct tcctcttggc aagattgttc ttcttcgaca    420

tgttccctcc cttgctgtcg ccgccgaccg gcacgacagc agccaaggga aggaggagac    480

gcgagcaaac cctagccaaa cacaacacaa gccttccttt ggcagtcagt cgaagagtaa    540

gtgggtcgtt aaatctgggc tagtggcgtc gttgcttgtc ttcaggccca ggtactgcac    600

atctggccca taccggaatg gcagttaaat ctctcttgca gttttgggct tgttctcgtg    660

tacgcacgca tactactgca tgctttcgtt gttttttttt tttgctcaag ggaaccgaac    720

tgtagtgaaa ccattgtcct gtagaatgaa tatgacctac ctacctacgt acctattg      778
```

<210> SEQ ID NO 62
<211> LENGTH: 754
<212> TYPE: DNA
<213> ORGANISM: Zea mays

<400> SEQUENCE: 62

```
aaaaaggacg aacattgacc agatttaacc ttgaagttgc agacatcaga atagactgac     60

agcttctcgg gatatgtggg atgagagctt tcaagtcaac ttcgcagcgg taggatagaa    120

gtaggtcagc ctggcaacta aagattggta tattagtaac ttcttcaaaa aggaacttgc    180

gtgatgaaca ttgtaattaa tacacaatag gtgtggattc tgatgtacat cacttcaaaa    240

aatgttgtac tccctccctc aaccttctaa ggcatatttt gatgcaaaaa aagttgtaat    300

tttgaccaac tgttgtcaaa ttaaatgtat gttttgaagt catattaata cattcataat    360

tttgaagtgt tttgtagtaa ttgaaaatat actgtgaaaa gaattcaaag gttcaaatat    420

gattttgaaa actttacata ccaaagtata ctctacaata ataaacagaa ggctcatatg    480

gcaatgcagc tttaaataaa gtgtcaccag atatgtaaag tatgatctcc aagtctttaa    540

aatggtacaa atcaaattgt tttcgagtca agagtcaagt catgcaacta ctgactagac    600

gaccagtcgt ggctagtcga atataggtcg aagattatat tttttataat tttctatata    660

tgctaatact aaaaacacgc taaaacacta aaaacacctt gtttagtata tcttcatcca    720

tttttatttt ctaccatata tcattaaatt attg                                754
```

<210> SEQ ID NO 63
<211> LENGTH: 885
<212> TYPE: DNA
<213> ORGANISM: Zea mays

<400> SEQUENCE: 63

```
tgcatgcctg cagtgcccaa tgaaaaccat gtggctggaa acgacgagga ggaagtgcag     60

agggctaggg aaaggagttt cagaggcgat gatgtgtcaa gctccgtgga tcatgacgcc    120

aaggtggcaa agcctctccc agaggaacaa ctgaacagca tggataagat atttgaaggc    180

accacaaact tgtctaacgg aatttcgttt cgagctcctg gaaaaaatgg atcatatgcc    240

ggcatggaca atgtggctac agtaccaact aattcacctt cacagaaaaa cgcaggcact    300

cctagcaatg acatagaaag caagacccac ccatctccgg caaatttgac cggaccagag    360

caaagtaatt cgactttgaa agatcaccca gatcaacaag tgaattcaac agcagtgctg    420

ggcaaccaag tacagccttt gactaaccag acgccgtggc ccgagttgga ttctccaaat    480

ggcaccttgg ctctggtaac agatgtccaa aagtccacat ctggagctgg agatgatggc    540
```

```
agcagcactg tggacaagag gacggacggt agagatggtc ccaaagaaga cgtggatgtg    600

tccacgaaaa taatgaacag ggcaatcagt gaggatgaag tcgttccaga gtgacaagga    660

gatctctctt gccggcttct ggtgtaacct gtaagtttgt aggacttggt ttcgtctcct    720

agactagact tggagatgcg caagcaggct gtctcgttgt gcacgccttt tgtgtaagtt    780

tgatagatgt ctgcttttgt actgccagtt agtagtccat cacaatgatc tgggtcgagt    840

ggagaacaag aagcatgtgt acccacagaa atatatgtag cgatt                    885
```

<210> SEQ ID NO 64
<211> LENGTH: 791
<212> TYPE: DNA
<213> ORGANISM: Zea mays

<400> SEQUENCE: 64

```
atccgtatct tctcaattac ttctcttgtt tgtgtatttg ttgtgcttcc tgttaattat     60

catgggaaag agatgaatca caatcatatt ccggaagagt cactgaatgt ttttactata    120

gccaatatcg tcgaagaatc tcgaaagtaa gatctgcatc ttcattccat ttacctgata    180

acccactttt ggcctgtacc ctgttgttat aattttttaa agatggtaac attgtaagat    240

tatttaatta tatgaaagat tatgtcactg catcaaatac aaagggtaaa agacttgaca    300

agtgaccatt ggcaaatctt tggaagaaga gaaaaaaaaa atcaatcatg gtccttggtc    360

ttgggtgaag aatgaataat atttggccca gttattttgt ttttccttct ctaggccaaa    420

caatattaac tattcagcag tatgttgtat tatgaggttc cttactttcc tttctcatgt    480

aaaactttcc ttactttcct tttattaaag ctactaggaa tcattatatg ttgtatggct    540

gaagtaaaac ctaacacatc tcccaaattg gacgagtaac tgaattgcaa gttggaatta    600

tcatacatat cattctttaa tactttcgtc atagcaagct aatgacatcc ctgtcgttta    660

ttgttgtgat ataatatacg tttcatgcaa ttacgcccct ccaactattt ttgaagagac    720

ttgtggttct ttgtcggctt tttctttgtg caggctttgg gtgcactgct ctgctttata    780

tgtcataaca a                                                         791
```

<210> SEQ ID NO 65
<211> LENGTH: 952
<212> TYPE: DNA
<213> ORGANISM: Zea mays

<400> SEQUENCE: 65

```
cacgtcactc cctcccccag acgcgtctgg ggatagcaac tcccatgact acaatgggat     60

taactcctct gctccctgtt tgtttccgga tggttccaat ggcgaggata tgttttacct    120

tgagcaagaa cctgggcacc tgggcgacca tgaaggtgct gctccggtag cagatagcag    180

attcggtgtt attgtgcagg agcagggtgt tattgtgcat gagcagggtg aggccgtggg    240

tactctccca aatgggaaca atggaattgg caatgagatg aatgtggagt gtaaaatggt    300

ggtgccgtgc agcaacgagc atcgaatggc gaatgctgtc ctagatgtgt ttgaggaatg    360

cctgagggag gcaaagagta atggggttat caatggtggc aatgtggacg ggagtggtga    420

ggaaagcgag ctctccaagc ggtggagagc gcagaggatg gatgagcttg atgtcttaag    480

ccggaggctg aggttgctgg ttgagtatgc tgcggcggct gggcagtgaa gcagagattt    540

tggtggtttt ggtgatgttc ctgccaccct tttccccttt tgtatagaag ctaggttcct    600

gtgctatgct ttggaatgta ttcctcagct ggacccttgc ctttagaaag cttactatat    660

ttaactatgt acccttgagt ttaataactc gagcagcata ataatctata attttaacgc    720
```

```
tgttatttgc atgggttcct gctgtttgat atagatgata gccttgttaa tgtagcttca    780

ggctttcaaa tttcctcttt ttcaattaga agctgttgta cttgtaactt gtaagctgtg    840

agagagtaat attatgtttc cttgttaacc gcttgtaatg cttctcttat agcttcacta    900

caacgtctac attcagcctg caatacccat gatttatttg caagcgcttc ct            952
```

<210> SEQ ID NO 66
<211> LENGTH: 501
<212> TYPE: DNA
<213> ORGANISM: Zea mays

<400> SEQUENCE: 66

```
tgcaaaagat gaggggagtt ttagaacata atagcacaca aaatggcaca accatggtat     60

gatagtatta agaaaaagtg tagaatgatc atacaaagaa gtatcataaa gattggtttt    120

gaggatactg tcatcatcta caatgaggat ttacacatca agatatcgcc catggatttt    180

aagttgactt gaaacagttt tggttatgta cttcaccatc taagattttt gcatcatcta    240

tggacattag gtcgaaaatt ctctaaatac tagacacggt tgtacacata cttccaacac    300

agatgaaact tggttcaaac ctataaacat atactgtaac cttacaagaa aatataattg    360

agtaaaagtg tgaagttcag tataacacct aacaatgcta tgcaagaatg cttcagtatt    420

gaaattatat aagatgacat ggaaacagct tgtgttgttg atgaaaagtt ccaatgtgtc    480

aatttgttag ggtgcatttc a                                              501
```

<210> SEQ ID NO 67
<211> LENGTH: 746
<212> TYPE: DNA
<213> ORGANISM: Zea mays

<400> SEQUENCE: 67

```
tgatcagcca ctggtataat aaatgtttct ggtgcctttt tttcttttaa ttaatgtaca     60

tagtagataa ctgaagcact aatcttaatt gtgtggcttg cattgcaggc tgaacacgca    120

cgcggtgatc gagccgttcg taatcgcgac aaaccggcag ctcagcgtgg tgcatcccgt    180

gcacaagctg ctgagcccgc actaccgtga cacgctgaac atcaacgccc tggcacgcca    240

gacactcatc aacgccggcg gcgtcttcga gcgcaccgtg ttccctgcaa agtacgcgct    300

ggggatgtcg gcagacgtgt acaagacctg gaatttcaac gagcaggctc tcccagcaga    360

tctcgtcaag aggtacgtag actagacata catagatcga ctacacgtac tgaggtgcct    420

atagaaaact gttcggttct tgacgtggtt acgttgtgtg cgtgcgttca gaggtgtggc    480

tgtgccggac cagtcaagcc catatggtgt ccgactgctg atcaaagact acccctatgc    540

cgttgacggg ctcgtcatct ggtgggcgat cgagcggtgg gtcaaggagt acctggacat    600

ctactaccct aacgacggcg agctccagcg tgacgtggag ctgcaggcgt ggtggaagga    660

ggtgcgtgag gaggcgcacg gcgacctcaa ggaccgagac tggtggccca ggatggacac    720

cgtccagcag ggtaccgag ctcgta                                          746
```

<210> SEQ ID NO 68
<211> LENGTH: 766
<212> TYPE: DNA
<213> ORGANISM: Zea mays

<400> SEQUENCE: 68

```
ataaggcttg gcagctccag aaccagcaac catatcaaac gatgacatta caagttgcat     60

ccgatgataa tagtgtttgt acttccgatc cacctgaaag caaatttcaa gttgatctta    120
```

```
aaaattcaga cataccagat actgcattag tgaaactatc aaaacacgcc tagcccattc    180
atctgatctg tcccagttag aaacaatttt gtcttgctga gaaaaaaatg tatttatgca    240
cccatcttac attttaatgg ggtaatgtaa ccttctgcat ttgatggtga tcttgtcctg    300
aataacagtt ttgtggatac atctgttcct attccaaata tgctcattgc ttgtttggag    360
gacctttagc taaaaacatg caatctacag atttaagcct tgttaaatga caatgattgt    420
gggcacctag gcattattaa gaaggctaga cccacctaaa ctaacaatgt ttgacgagtc    480
ctccaagaat tttcaagaaa tcaacttgtg aaactcatgg agctgaacca atataaatga    540
cctttgcatc aggaaccaac tattggactc attatttagg tcacaactca aactgaactg    600
atggggttgg gattcctcga gtatttctct aggaacagaa ggcagaaaat tgttgacttc    660
tgatatacca gtatgagaaa aagtaatatg cagccatccc tagataaagt attagtttaa    720
taaaattcat atttggaata tcaaaagatt attggtgaaa ctaata                   766
```

<210> SEQ ID NO 69
<211> LENGTH: 761
<212> TYPE: DNA
<213> ORGANISM: Zea mays

<400> SEQUENCE: 69

```
aatacgagct cggtacccct gctgaggatc tcatagttgc gatattgact gcattggact     60
gtcttccgat cagcaatgag caatcagtct cctgtggggt tatgcctact gttggtcacc    120
tgctggctca cagaattgcc gtgatcaacc aaaaggcaag agcactctgt cacaagtggg    180
gcggtgtacc aaaacatggt acaaatggag agcattttca tacagaggag tcaagccaca    240
ctgatcagct taagtctcca gatgccggcc acaagacaga aactaagaga aagtgtgtag    300
tggacgaagg agagcctgat gaagaatcaa aacctgaggt gacaactcac tcagatgcac    360
ctttgtccga cccttctctg actaatgata atgcagatgc aacagagcaa ccagcagggc    420
taacttcacc aaatccatca aacggaaatg caacattagg ggatgtgaac aacttggtca    480
ggtctcctac atctgcaggt catgtgggtt tagaagatgg gcagtccacc cccaatgaaa    540
tttcttccaa tgatgctgaa ctgcccatta atggcatact ccggtcaaac tctactaatg    600
caaaaagtgg tactggacaa gatgctccag tggaatcaac tccagtggcc atgtctgtag    660
accataataa acctggaaag ttgtttcctg gtagtaaaat gggtctggag gatagtatta    720
tttcagttag ctcaagtatc aaggagtctc agccatttgc a                        761
```

<210> SEQ ID NO 70
<211> LENGTH: 827
<212> TYPE: DNA
<213> ORGANISM: Zea mays

<400> SEQUENCE: 70

```
cttgcatgcc tgcagccccc ttgggccctg acaggtcttg acactacacc cctcctggac     60
aagcagctcg tcctcgagct gcaacataac gggtgcccaa agaccgactc tacttgaccc    120
aaaaccaaac actgtagctt agcgggccct cttgggccct gacagttatg agctaatgaa    180
atactaaaat ctgtcttaca ttatgtttac ttgcatcata atatctatgt tcactaaaac    240
aatcttgatt tgctcttgct aattttctct ctatcagatc catgcactgt tcattgcaag    300
atctattttg tttcagggct tcatctatcc caattctccg ttgctaatga gatcctgctc    360
tttgcctcta tttttcgttt ttaggttggc aacctggaat tcaagagaca gcttatgcat    420
gggatgaaga atgggataat tttggagatg aaggtatgct agcttcaatt ttgattctac    480
```

```
caccatgacc attattcaat ccgtgtttat gctgacaatt tacatattaa actatatatg    540

ctgctccgct tgcatttatc caggattctc tataataaag gaactaacag ttgaagtgga    600

gcctcccgtt gtagcaaaga gtcagcctac tgaggatgtt aaagcatctt caaatggggc    660

atcaacagaa aaagaagaca acaagggtga taaatctgct gctgctgtgg agcaggttgt    720

caaacctgaa acagcacctt cgaatatcaa accagagtca gcaaaaagtc ctccagttag    780

tcctgtcaag acaaagacga tggtcccgat gaacatgata aaaagca                  827


<210> SEQ ID NO 71
<211> LENGTH: 762
<212> TYPE: DNA
<213> ORGANISM: Zea mays

<400> SEQUENCE: 71

cccctcttgc gtgcctgcag tgtgtcaccc cttgcttggt tcatgtcaaa tcaggaaact     60

agttttgtga caattggaca acgagtgctt gccaatccac tgaggtaacc atcttggttc    120

atatttcatt ttacattcat gttgtggtta tgcattatct attggttcta gtatttcaat    180

ctttaggttg tgtgaatcgt cctcttattt gttttgttct tcggggtgtt actatcctaa    240

gatgtttgct ttgtaatttt tttcctgaac cttctttatt cagggttcgg tttcattatg    300

gccatcctga tgtcttcgat cgtcttttcc acgttacgag gggcggtgtc agtaaagcat    360

ccaaaattat caatcttagt gaggacatct ttgcaggtac ttttcttttg ctgttactgc    420

tcaacatttg taaatgtgga accactaaga taatattttg gcttcttatg gttcaggatt    480

caattccaca ttgcgcgaag gcaatgttac tcaccatgaa tacatgcaag ttggcaaagg    540

aagggatgta ggtctcaatc aaatatctct gtttgaggca aagatagcaa atggcaatgg    600

cgaacaaacg ctgagccgtg acatctaccg gctaggtcat cgctttgatt tcttcaggat    660

gctgtcttgt tactacacaa caattggttt ctacttcagt acaatggtat ttttctgacc    720

tgaattgtaa accgctcttg tttattcatt ggttaacact ta                       762


<210> SEQ ID NO 72
<211> LENGTH: 470
<212> TYPE: DNA
<213> ORGANISM: Zea mays

<400> SEQUENCE: 72

tgattctatt gattgcagtt ttatattgtg atgttgtgga ggcatatgag taccattttt     60

ttttcttctt aatatagcac tagtgttctg ataggcgcag gaaatcaaca gctcgtgcag    120

atgggtttct tcgagcaccc tctcttgtcg acaaccttgt tatattttag aagttatttg    180

tttgacatcc atccatccat cttctctcca aatttaggtc ggatgtacga gctctatcga    240

cgttatattt gtgcctccgc gagtccgagc tgacccagca gcgagtcagg taccagcagt    300

agagttgttt gttttgtcgt cccatactga aaatctatca tctatgcaca tctcttgcct    360

gatccccctt tcgccttctg tatcgtggtt cagaatccag cagttgttgc caggaggatg    420

gttctgaagt caccacgcct aaggatcaaa aggcatgtcg tagtggcaca               470


<210> SEQ ID NO 73
<211> LENGTH: 465
<212> TYPE: DNA
<213> ORGANISM: Zea mays

<400> SEQUENCE: 73

tgcagttggg tgacatagta atttctgttg acacagctcg acggcaagca gaagaaaggg     60
```

```
gacacacact tgttgatgag ataagaatcc tcatggttgg tttgttcctc tctttatttc    120

ctaataatgt ttaactgcaa cttttccagt tgcataaatg gatcaatagt cgtgtggatg    180

ttgtcagatt tatcaatata gtcattttca tctttgctgc actttgtacc tccataatac    240

gcaaatagga tgttcagttc actctgcact ctgaaccttc acaataggag catacaacat    300

taagaaaatt tgtatcaaag gcataaaaac catagagcac tgttttaatg gagcagtatc    360

tgatatttaa aagctgcctg caaaaataga gactaaaggt catggcgaga tgcacaatgc    420

actagtgctc aactgcttgt ttccatcagc cattgtgtat caaca                    465


<210> SEQ ID NO 74
<211> LENGTH: 477
<212> TYPE: DNA
<213> ORGANISM: Zea mays

<400> SEQUENCE: 74

tgggcagggg tcaggtgcgt gaacggccaa gtgtccgccc tgtccttcca gaacctcagc     60

atagccaatc cagttccagt cccagctgct tccatatgca acctcaagaa cctgtcgtct    120

ctcgaccttt cctacaacaa actcaccggc cagttcccca cagcgctcta cagctgctcg    180

gctgctcggt tccttgacct ctccaacaat cgattctccg gtgccctccc agctgacatc    240

aacaggctgt cgtcggcgat ggagcacctc aacctgtcga gcaatggctt cacaggcagt    300

gtgccccggg cgattgccgc gttcacgaag ctgcggtccc tggttcttga caccaacagc    360

ttcgacggga cgtatccggg ctcggctatc gcaggcctca gcgagctcga gacgctaact    420

ctggcaaata acccccttcgt gccaggcccc atccccgacg acttcgggaa gctgacg      477


<210> SEQ ID NO 75
<211> LENGTH: 1375
<212> TYPE: DNA
<213> ORGANISM: Zea mays

<400> SEQUENCE: 75

ccagcagggg gaaagtaaaa aggccgaaaa gattggagca tgcagaaatt ctgaatacag     60

taaggtagcg tcctctacaa tcaagtcaaa gaagacacaa atattaggag acacatcaag    120

agctccgaga gatgagttga tcactaaata tcccaaaggt gagtgagaat cccatatcca    180

tctaattttg taatgcaata tgttcaacac ttcttttaaa taatttatgt aagtttaatg    240

tagaagcaca atgtgtcaaa acatggattt ggcaacaaca ttacctgatc atctgattga    300

tcccaatttg gttaggctaa tcggcccccc aaaccttgcc taggcaccgt aggcatgtat    360

gagtccatgc attagcgcta agctgctaat agttagcagc tataattagt cggtcaggat    420

tcaacatgcc tgctaattaa tagacctact acttattagg tggtggagat atcaagtaga    480

ttcaaacgac ccttgatatt aattaagtac ctaatagtta cttcctccgt tctttttttt    540

atttgtcgtg gtttagttca aaaataaact agcaaacgac aaatactcga gaacggatgt    600

agtatttcag attagggcat aacaatgttc tagcctccct ttatttgttg ttaattgttt    660

gtttccttaa tttgaaggtg acgggatgga tcaaatggga tcaagcgccc aaggtgacga    720

aaaagaagat gcatccataa tagacacagg gtatggtggg atctaccgct ttagtgggtg    780

tctggtttat agggactaaa ttttagtcca tccattttaa tccattttag tctcaaaatt    840

cacaaatata gaatatttag aatttaggga ctaaaataga ataaaatgga gggactaaaa    900

tttagtcact agtaaccaca aacaccccct tattctttga ctatttgctt cagcttattt    960

gtttactcac tagccatgac attctcatat tcacattagc tgtcagggca tgtacagtgg   1020
```

```
tgtttaatgt ggagtctctt aaggtgttta agggggttat ttgcaaaaaa atcttagagc   1080

cgtctctccg tgaagagacg cctctggctc gtaaaccaag tagcaacaga cgcctcactt   1140

cccactgtac gaatttgttg tctgttctat cgatctgatg ctatacaaat acatttaatt   1200

ctgtatttat taatagacta cgtttataga cactccattg tacaatagag tctctttgtc   1260

tcctgtgctt ggagaaccgt tttggtgtct ctccactgta catgccctcg tataacaaat   1320

atttaacttt cctttacacg ttgtgtgata taggctactt ccaaattccg aggaa        1375
```

<210> SEQ ID NO 76
<211> LENGTH: 653
<212> TYPE: DNA
<213> ORGANISM: Zea mays

<400> SEQUENCE: 76

```
gggttcagtt cacctcgcaa cctgttgatt agagagtgac acaaggaact catagttaga     60

agtaataaag gaatcagtgc tgttcaccaa caaaaagggc tctgtagatc acaaattagg    120

ttagaaacat actggacaag tttgtcaaca cgtgcatcta ctgtcaagta gtaatgagga    180

atggtctgtt tcgatgctag caagcgattt gcagtaacct gaagacaaca aaaggtcaat    240

acattatcag gctgttatca tctaatatga aaatgatgcc taacattctg gccatcaaaa    300

tttacctttc ttatctgtgc atttggaata tcaacataac ctaaccctgg atctgcaaaa    360

gactccctca gcccaccctt ggctacagaa gcttcattaa gacattaaca caggggggtca    420

taagttaggt tacagttagt tcagctaaat gaagtcaaaa tgccaaatca tgggatatta    480

ttacaagttt attaccaaaa tgaaataaga tacaggactc atgatgtagt gagggcctgt    540

gaggccacaa cattatataa cctaaagtca aataattaag taactacaag tgtaacaata    600

actcagggaa accgagcgaa ttgaactttc ctctgcaaaa tctaactagc ata          653
```

<210> SEQ ID NO 77
<211> LENGTH: 513
<212> TYPE: DNA
<213> ORGANISM: Zea mays

<400> SEQUENCE: 77

```
atgaatgaag aatattcatt cgggcttggg aactgcaaaa caccagcaga gaattaattg     60

acaactgtac tgtgtgtgta tgcgcgcgct actaacagtc agaatacatg ttttgagatt    120

aacatacctg tgctttcaat tttgatttcc atgtcacctc gacaaggtta atgcttattc    180

cataagcaac aaccaatgta gcaagatccc tcacataccg agatgacaac agaaccttca    240

tgctctcacc catgctgagc tttggcttgt cctgaaaggt tatgttcgca gaaccgttaa    300

ggagagatcc ataaacacaa gaagaagaac aatagaaaat ctgccaggcc caaccttctt    360

tttccgctca accacgggca cagatgagtt atcaataaca aacttgttca ctccccaata    420

gataccggtg atgacaagac ccagtacaac cactatgctc atcatggcct tcaacgaaat    480

tgcccaacca tccactccag gacccaaatt ttc                                513
```

<210> SEQ ID NO 78
<211> LENGTH: 495
<212> TYPE: DNA
<213> ORGANISM: Zea mays

<400> SEQUENCE: 78

```
tgtaggctcc tattactact gcaggtctgc aggcaagagc tactagccgc tgcatgcatg     60

agcatgagca tgatagacca ctagagccgt ggacatagtg ctacagtaga cggactagct    120
```

```
agctagctgc aaatgaacgc gatccgtctc caaaggccgg gagcgcaaac atgattacgg    180

atcaaaagct aggccatcat tgtacgctgt tagtagcagc gctccagtgc gcagtgattg    240

attgctttgc ttcctcgcca tcgcgcgcgg cccatccctg cctttttgca gatccgaacc    300

ccggccggcg ccggtcggcc ggccgatgat gcgcgcgcgc catctatcgc ttggctgcag    360

tgacagtgca gcagcaggtg gtagccatca cgtactacca ccggccggag tcgtcgtcga    420

tccggccgga gcggagcttt ctcggtgacg gtgacgctag ctggcatcaa tggctgagaa    480

aaaaaaaaaa aaaaa                                                     495
```

```
<210> SEQ ID NO 79
<211> LENGTH: 886
<212> TYPE: DNA
<213> ORGANISM: Zea mays
<220> FEATURE:
<221> NAME/KEY: misc_feature
<222> LOCATION: (831)..(831)
<223> OTHER INFORMATION: n is a, c, g, or t

<400> SEQUENCE: 79

gcatgcctgc agctctgcgt gaacatgctg tcatcccttc gagtgatctg aggacccagg     60

ggtgggcagc ggggtgggag gtgtggcgac cgagacatgg cgagaaaaag ccctcgtatc    120

tttgatggcc ttcctctttt ggttctgcta agtaactaga gccaatcgag catcccttgc    180

gctgttcctt tcatatggaa aaacagcagc tttgggtcag atccgaatgt aaaatagcct    240

gcattagggt ttgggaaggg tttggtgtgc tcgatttcgc acagcaggaa gaggagttgc    300

tggcatacct ggtggatgct tgtttccagc caaagggccg acgaagacct ggcgaaggtc    360

gacgcgggtg cccagtcggc gccgccaaaa gtgaggggtg tgagtagtga gggaggagaa    420

aggaaaggga ggcgtgattc gggtgaacgc aatcgtcgag gacgcggttg atcaacgcaa    480

atgggccttg cggccttgaa gctggcggcg gaacgaaatg ggccttgcgt tgcagtcctg    540

ggctcctggc tcatgggcaa cggccttgcg ttgccaaccc ccggacggtc cccggtcact    600

ttccgaccgc acgtatgccc acgtcaccgt agcaccgttc caccccacca caaagctgga    660

ttccacatct gccctgcgga tccaattttc caatcactct cactgccatg ccgaccccac    720

agcaagaagc cagccacgga tttgacggga tgggataccc tccaaagtcg gaaaccgcgg    780

tttcctttcc ttccggcggg tccgggcccg aattaaacgc gtgggcgtcg ngaacctccg    840

tgggcgtccg tcggtccttt ttcccttctt tttttcccaa cacctt                   886
```

```
<210> SEQ ID NO 80
<211> LENGTH: 807
<212> TYPE: DNA
<213> ORGANISM: Zea mays

<400> SEQUENCE: 80

tttccatctg ggatacgtt ctttagtgag ccaccgtgct ggctcgatga tctccttgca      60

gattccggga aagctcccaa gcttcctcct ctcagaaggg cctgtagcga ttctgatgcc    120

atcttggatg ctctgtcaac atttgaaagc ccaatttgtc gaattgagga aggcaatcaa    180

atctctggtg gtgaagctga tgacttgttg gatgctggcg aaggtggtga aagcggttct    240

gtggtcgagg ctagctgtgt ttatggtccg aattcaccaa gacagaagag taggctgaca    300

acttcagaga gttccatggt aaatgctgtg cttgagaatg tacccagcaa ccccttgcag    360

tacttgagca tcgatgcctc cagtggtatg aatggtaatg tggccaatgg aactgctgat    420

acctgtgatg cttttggcca ccctgatcaa gacaagtcat ttaaaaggta cacttacatt    480
```

tgtgagtgaa atatctaaaa tacttccttc gaatattctc tggtaaagta gcggtacatt 540
gctgctttta ctaaactgga gttttttagt gaaaatgcta gaaagatata aattatcaag 600
tgcagatgtg aactttggct ctcgccaaca gaaatggaac acgacactct actgctttgc 660
agaaattaaa ttaactgatg gcgcttctaa ttgagtaaca ctaacgacaa cagctactat 720
gccaatcagg ttttaggtgc aagtgtgtaa tgaacctctt gttccgttag acattattcc 780
accgtaatat aacttggttt gttagag 807

<210> SEQ ID NO 81
<211> LENGTH: 617
<212> TYPE: DNA
<213> ORGANISM: Zea mays

<400> SEQUENCE: 81
tgctctacca gaagcaaaga ctcgctccgc ccgcccatgc cgttcacgag gacgtcgacc 60
gtgcgcgctt tggacacgat ggcagggaag aattccgtcc acttgctctg caagaacaat 120
gacgaccgtg cacgtcacgc ttcacgacga cgtggtggta ggtgcgaacc gtatgtaaat 180
agtgctatgt attttactcc tattaattgc agccatgaac tttaccgagt ccatgaacat 240
gtcgacgagg ccgatggcgc tcatgaagac gagccccgtc tcgcgggagc cctcgacgtg 300
cacgtccggg ccgcggaacg agccgtcggg cttggcgaag atgctgtcgt acgtgtcgac 360
attgagcacc tcgcggccgc ctgtcttgac ccacaggtgc tcgccggcct gcgccatcct 420
gatgagctcg tccatggcgc gcgccgccat ctcggccatc atgggccgct ccatctccga 480
caccgccatc gggaggaggt ggaacggggg ataccccgag gagccgccgc tgaggaggtc 540
gaggtccagc gacgggccgc cgagcccgcc gacggacagg tccagcgacg acatggacag 600
cgcctgcgcc gacggca 617

<210> SEQ ID NO 82
<211> LENGTH: 774
<212> TYPE: DNA
<213> ORGANISM: Zea mays

<400> SEQUENCE: 82
gttgttgggg ctgagaacaa cctactgctg ctgcactcaa ccacggccgt attagaaagc 60
ttgggaccag taagataatc aatcgacaag ctatatatgc tggaagccaa gaagacaagt 120
attagtagta gtagcagtag atgaccatgc ttgtgaaacc actactgctg ctgcactcaa 180
cattagatct tctgaatagg taggatcctt cagggtttca ttctcaaaaa tctgaatagc 240
taaacaagtc tgtgctgact agtacataaa tataagaaaa tatgctggat atttttcggt 300
tctcatcagt tatgctggtt gcaaaatttt cctcgcacaa ctggaagata cttctacacc 360
aacttcatgg actcattctc attatatctg tgaattcaaa agctttcgtg gggggaactc 420
ccctcaaaac gtaaagcggt aagggttggt ttgatgacaa ggggattcaa gtgaattgaa 480
tagcaagaga ttttcttggt ttgaatagca agaggattcc tctcctatgg atcccttcaa 540
ttctctggtc accaaatcag ccctcaatcg cctctaattc ccttatcatc aaaccagccc 600
taaaggtctg agaggcacaa tagaaaacag catggcttca gtcaagcagt accatataaa 660
aacaatattt tggtagtgga gaacaaaatg tctgaactgt acgatcttat tcgagattca 720
aaccaatgaa gaaagaagaa aattacagat ctttttttaat ataagggttc aagt 774

<210> SEQ ID NO 83
<211> LENGTH: 803

```
<212> TYPE: DNA
<213> ORGANISM: Zea mays

<400> SEQUENCE: 83

cttgcatgcc tgcaggcgtg cctgggaaga cgacgaccgc gccgcgccgg agagactagc     60

tagccggagg ccggccgggg gcggcggcgg cggcggcaac agaagctacc actgccggtg    120

ctcatcgtcc tgcacctgaa gcagcagcag cagctgatct gatcgacata cagttcgtgt    180

tcggcagcta gcccctctag ccatgctcgg agaggtttaa ttaattacgc agcggactcc    240

ttcgatgggg gtggattttt ggtgatcatt ctgggggtat gtataaacct gcaacctacc    300

cttgcaagga ttagtttttc ttcttctgtt tttcttcttt caagtttcac cgaggtggag    360

tggaggttga ccgacattat tctgttcttc ccgcatattc ttgtgagatt ttgattccaa    420

tcagtgtcta tcaattcaat ttcgatctcc ctctctgtaa ccacatgtcg tgtggcgtgc    480

gtgcgtgtaa aaaatcgaga aaaccgagcc tgccctgtcc gggcttcagc ttgtttgttc    540

tagctagctc gatctagcgg aaacgactgc cgtacccttt ctgtttattt ttagttggca    600

ctggatagtg gaaaattgaa ctatctagcg acaactaaga agaaacatat gaagtataag    660

tgagacgtgt aagcgagtct tctgaatttt aaattataat ctaattaatt ccttcaccac    720

cagcttgtat accttttata aaaaaatctc taacaaaact acaatacact tttggtagat    780

ctggtctaaa gataaaaaag ctc                                            803

<210> SEQ ID NO 84
<211> LENGTH: 470
<212> TYPE: DNA
<213> ORGANISM: Zea mays

<400> SEQUENCE: 84

aaaattattt gatgatagcc ctacttctgt atggttcctt cttacatagt ttttcccctt     60

tgtataataa tcattgttca gatccaatca cttgttgaca aaatctctta tgaaactaaa    120

gtcaggtgac agtagcccag agagttctac aaattcaaca aaaaatgaaa ataggaatga    180

aaaacacgaa acagctccaa aggaaaaaac atcaaagaag aaccggaaga aggagaaaga    240

agtggcagag agtgttcctg taaagcctaa aaaggaaaat aggcctttgg ttctgccttt    300

tgaattatct gttatgggta ttttattgct catcgtatta ggtggtttct atgtggtaag    360

ttctctgttg ttagtcttac cagaatgaag acaatgaatg tcttcattga atgaggtaat    420

cttaatgtta atgattccat ttttttaggt ccattgtgta tgggcggcag                470

<210> SEQ ID NO 85
<211> LENGTH: 924
<212> TYPE: DNA
<213> ORGANISM: Zea mays

<400> SEQUENCE: 85

agtttgcatg cctgcagtgg ctttcgaagc agacgagcgg gaggtcacgc tgcgagcctt     60

ggtcggtctc ggcggttttg cgcttgagaa atttggcagt ttgagcagag aactgcaacc    120

aaaaagtaaa aaaaaaatta ctcggttatt attacttaat taatcaaatg cgatagcaag    180

cacgctaagc atactcaagg agagagagag atgtgtgtaa taagcaaacc tgcaaaaatc    240

aaaaggcggt gttattggga caaggtccag gagcgggtga tcctcgccct gtacatttgc    300

tttttgttga tcgttctcct tttcttgttg aggattttct gtctggtcac tttcttcttg    360

tttcatttct tcagggagtt cagtctcggc tggtgcagca agtgcgccaa caaagcaata    420

atgatcagag ggatgagagt gcgtaaatgt agacatatcc aggaaataaa agttgattat    480
```

```
tcagaaatct gaaacgacca aaaaaattgc aaagacaaaa atatgctctc tgaaacctga    540

tgtctttttt ttttacagcc accacctacg ctgtcataga acaattttgt ttgcacatga    600

gccttttaca gtggtgtctc atgcgaatta aaatcatagg caaggtaatc ctattgttgt    660

tcggtgcata gaaacacttt tttaatgaga ataccactga acttctattc ttttaaggga    720

tgcatcagaa gttattagta tcataatata gtcagaaaaa tgccccagga tgggactgta    780

ctgtacatgt tcctaaacaa taattacgaa tctgcaagac gaataagtat agcatcgtta    840

tacaaatctc aaacgctaaa tactcaccat ctcttctgcc aaaagcattt tggcaactct    900

cacatcaaca ggtcgataga gagg                                           924

<210> SEQ ID NO 86
<211> LENGTH: 669
<212> TYPE: DNA
<213> ORGANISM: Zea mays

<400> SEQUENCE: 86

tccttgacgc tatcgcgcgc ggcggcctcg ctaatccgga ggcactccag ctcctgcttc     60

gtgcacttca cggcggtgtc cttgtcgccg agcacgctct tgagcagggc gttctcgctc    120

cttgcctcct ccagcgcctc cttcgccaca ttggtgtcct tcaccgcctg cttcaggatg    180

tcccgtagct tggcgacctc ggcccgccag gagcgctgcg agtccaggag ccgcgcgttc    240

tcgtgctgcg cctcggcgag ctcggcctcc gttgacttca tgcacgccgt aaacccgtcc    300

tccttgcccc gccacgcggt gaaggactcc tcggcttcgg cccggagccg cgccacctcg    360

tcggacaggg cgcggagctt ctcgtccttg cgtttggccg acatgtgcag gcggtcggcg    420

tccagcctgg ccgactccgc ctcgtgctgc gcgcgcgcca gctgctgctt cgtcgtgtgc    480

agctccgcgt tcacctcctt gagcgctatc acgaactcct ccatcgcctt cttgctcttc    540

tcctccgccg ccagcgccac ccgcagctcg ccgtgaaccc tctgcatgtc gcggtcgcgc    600

cggtttctcg ccggcatcgt ggcgacgggg cttctggcgg cctcgagcct ctggacggtc    660

tcctgcagg                                                            669

<210> SEQ ID NO 87
<211> LENGTH: 545
<212> TYPE: DNA
<213> ORGANISM: Zea mays

<400> SEQUENCE: 87

tttttcattg gcggtgcatg gggtacgcgg cgttcggcga caaggcgccg gacaacctgc     60

tgacggggtt cggcttcttc gagccattct ggctgatcga cgtggccaac gtggccatcg    120

tggtgcacct ggtgggcgcg taccaggtgt tctgccagcc catcttcgcc ttcgtggagc    180

gccgcgccgc cgcggcctgg cccgacagcg ccttcgtctc gcgggagctc cgcgtgggtc    240

ccttcgccct cagcgtgttc cgcctcacgt ggcggtcggc gttcgtgtgc gtcaccaccg    300

tggtggccat gctgctcccc ttcttcggca acgtggtggg gttcctcggc gccgtctcct    360

tctggcccct caccgtctac ttccccgtcg agatgtacat caagcagcgc cgcgtgcccc    420

gcggcagcac caagtgggtc tgcctccaga cgctcagcgt cgcgtgcctg gtcgtctcca    480

tcgccgccgc cgccggctcc atcgccgacg tcatcgaggc gctcaaggtt taccacccgt    540

cagca                                                                545

<210> SEQ ID NO 88
<211> LENGTH: 842
```

<212> TYPE: DNA
<213> ORGANISM: Zea mays

<400> SEQUENCE: 88

```
atgagcaacg ttctaattaa tttcactaga cgggcaatgt tgacagcaag aaccacagat     60
gagtcttatg gagagctcta acaaaaaaat tgcaagtcaa gttggaagtt tatctctgat    120
gggatttgca tagtatgtct gctggttcgc attgttacat tgtgtctgcc aaaagatttt    180
atgcagataa caacccggag cttatgtcta acatgtgaat gcgtttgaga caatgtacct    240
tgacagtgtt tagtagaact ttggcttcgt tattgttgtt gaagtggtca cgaacaggct    300
ggaaaaatta aattagtgag tcaaacctac aagtgtgaac cagcactgaa aattgtgtaa    360
taatagcttc ttcctcgaca aaagaaggac aggcaataaa caagatggac aagttcgcca    420
gaaactacgc tagcaagaaa caagagcgat gatgcagcaa taacgacagc ccatcaattc    480
attttgtcag gacagcagct atttcatttt caaagaaatc acagtgcaag acatgagatt    540
ggtaaagatc aagaatatac aagtttctga ccagagaaag actacaataa tatcatagaa    600
aaaaagtagg gtcgagtgaa gaaaattgca cctgcaaaat ttcatttatt gcttttgcca    660
gtgcaggttt gacatcagca ggatgcaaag caccagtctc ataatcagaa attagttcat    720
ccatgcttgt aaatgtcctg tttgagtgca aatgctttag aagtataatc cgagataata    780
aatcatgtca cgttggaaat taaaataacc tatttgctgc attaataaat tgcatgacca    840
ca                                                                   842
```

<210> SEQ ID NO 89
<211> LENGTH: 749
<212> TYPE: DNA
<213> ORGANISM: Zea mays

<400> SEQUENCE: 89

```
attgttgaga tgaaggtgat gaaggcgacg aactcggcga cgacggccca tggcacggtg     60
aagtagttgc gctgcacgtc cgcccacatc atgaagagcg ggtgctggct ccgctcccgc    120
agcttgttca gcgtcacgcc caggtagctc ttctccagct ccgccgccgc ctcgctcgcc    180
gcgcccacat gcttgaagaa ccgcgcgatg tcctccttgc tctcgctccc ggcggactgc    240
accacctccg ctgccaccag cacgcccgcg tcctccggca actgcaccag cttcgccatg    300
agccacacgt acgccgacac gtccccggcg cgctggtccg ccgactgctc gaatgccatc    360
aggttcagca gcagcggcgc cgtccggaag tcgatccgta gctgcggcag gtgcagccgg    420
tcctcgtgcg ccagcttcac ggccagcggc acagggccca gcaccgacgc gatgccggcc    480
ggggccttgc ccgtgctgcc gccgcgcgcc ttcttgaacc gcacccacat tcgcttcagg    540
tcgctcgctg acggcaggtc ctcccgcccg tagctcgcgc gccaccggct atcctcgggc    600
aggatcgggt acagcagcgg caccaggagc agcagcggga ggcgccgcag cagccgcgct    660
gtctcctgca tcatctccag cgccgccgcg ttctggtgcc gctgccgcgg gctccacctg    720
gtgcgcgccg cggtgaccat cgcgtggag                                      749
```

<210> SEQ ID NO 90
<211> LENGTH: 747
<212> TYPE: DNA
<213> ORGANISM: Zea mays

<400> SEQUENCE: 90

```
tggttggtgc gatcaggact agcttgttct ggccaccagc ttgccagctg ccgtctcctg     60
caatcccaag cggggatgaa tcggtaatga ccaagttaat gatgctctgc actcgtgtag    120
```

```
cacctatgtg ttatgtcctt gtaatgttat atttacgcca aggtttgcag ttcgtaggtt    180

gtctcctgta ggtaaattgt gcagggatgg agaataggaa attatgaaac accagtacat    240

cgatcatgcg aataagaact gcacagtcta aatccaagta gtaattcact gtctatctgt    300

tacttgggag tataaacttt ccttggaata cttatattat atgattatat ttatttattt    360

tttcaataga gctaaaacac ctgctttcta ctaactgatg cctatattac caccggatat    420

tcacaagcta aaattctata tcactttctt gctaactgtt atttctggta cattgcttat    480

acacaggtgg aacaactgtg gcacagttgt gctctggact tgaaaattcc tcaagatgtt    540

agaaacaggt cccattacag ccttctgttc aacaccatca gcaattcgta tagagaaaat    600

gataataagt tctatcctca aaagattggc attgaggaag caatcaccgc aaccttatca    660

cctgcaaaag atgccaacac ttttctggac tgcttaaaga agcataattt ccctttctct    720

gatcatggac tgcaggcatg caagctg                                        747
```

<210> SEQ ID NO 91
<211> LENGTH: 999
<212> TYPE: DNA
<213> ORGANISM: Zea mays

<400> SEQUENCE: 91

```
tgcatgcctg cagacggggc cctgctgcca ctgtgatctc gtgagctaac ctgtgtgact     60

gtgcgtttct tccttcctcc taccctcccc tcccgtcctc acctcagact agctcggaat    120

cctccgtcgc cgagcaaagg ttccaccaaa agaccaaacc ccaagtcctc gcaggatttg    180

attctctgac cgattcaggg acaccttcct cagagcaata cttaccagcg tgggcgtggc    240

taccaaccgc atagtttcca tgagcagatg caaaccagtc ggcggcgaga gcccagcagc    300

agacggacct gacccgcggc ggccgatgtc ggagacgccg tgttccgtgc agcccggggt    360

cctccctctc ctcgggaagc catacttcac atgcattctc tgcaagtctc atgtcaacca    420

gccgttccaa gtggtactgc tgctactcat gctctctgct tgcatctgct gaaacacttg    480

tctcctgctc ccgctcgctg ctggggggcg caggctaaag ccgtgcattt cgtagtgtaa    540

tgatcgaagt cctttggtgc ctggctctgg ctggctgcat ctgcatgcag gtggtcccca    600

agtcgctggc gccgttcctc ccggggacga cggtgccggc gacggtgacg tggcacgggc    660

ggtcctggga gatgcggttc acgggggggc ggcagatcca gcgcctggag gccgggtggc    720

ggggcttcgc gctggacaac ggactgaagc tcggcgacgg gtgcgtcttc gaggtggtgg    780

acggcagggc ggagcgcgtg gtgttcaggg tgcaggtgct ccgcgccgac atccccgcgg    840

agatccggga gcgggccggc gggtacactc cgtccagccc catcctcatc gactagctag    900

ctcattgctc acctcatctc atcagctgct ggtctgtatc cccccgtgcg gccgtctgcc    960

actgtcactg cgccggcctg aaactgaact gattcagct                           999
```

<210> SEQ ID NO 92
<211> LENGTH: 572
<212> TYPE: DNA
<213> ORGANISM: Zea mays

<400> SEQUENCE: 92

```
gtcgacctgc agctcggtgt cggcctgcac cgactcgtcc gacgggtagt acgtggccac     60

gtaggcgccg caccaccgcg tgatggccga ccagaggagc agcccgtcgg tggcgtacgg    120

gtagtcctcg atgagcagcc gcagaccgtg cggcttcgtc gggtcctcca cggccattcc    180

tctgtgacaa gggaacacac accatgtcag cctgcggctc gtacttccga ttttaatttc    240
```

```
cattccaggt gtttttgtgt accttctgat gagatcggcg gggaggccct cctggtcgag    300

ccgccagagc tcccggtacg cgaacgagct catctccatg cagtagcggc caggggtgaa    360

cccggactcg atgacgccgt cgccgttgat gaggatctgc cgcgccagcg cgttgatctt    420

gagcgtgtag cgcatgtgcg gcttgagcag cttgaagatg gggtgcatcg cgctcagctg    480

ccggtgcgcc gcgatgatga acggctccat gcacgcgtgc gtcctcagcc tgcacacgca    540

tgcagcgcaa tgattagtcg aatccaacaa cg                                  572
```

<210> SEQ ID NO 93
<211> LENGTH: 734
<212> TYPE: DNA
<213> ORGANISM: Zea mays

<400> SEQUENCE: 93

```
ttgcatgcct gcagagattt gttttcagca atgaagaatt caccataagg atcgtcaata     60

actccctcat acacccacct aacatggccg aaaacaaatt cacataatag catgagcact    120

aggactctaa acaagacatg acaataatta aaggatgtgt gttgagtatt gacttcagct    180

taaacgtgaa agctagcaaa gacaaacaag gaaagaagct atggacaatc atgaaccttt    240

ctagcatcct gaggtatgct gcacttgcat attctgtcat cttctccagt aaagaccgaa    300

caacactatc accacccatc gcctttgcct gagttgaagg atatgataga tgcattacat    360

gtttaaataa gtataatgtg aattcgggaa aactaagctc tgagaaaaat gtgaagtaag    420

aaaccaatcc aattgaagaa aatcgtttta tctataagaa aattaaaaac tggactgcta    480

tatttatctt atatttacag taagcagaca ggaggaggga ggaggcacag aaggaacagt    540

gtgtaatctc agaggcataa actcatttga gggagtacct ggctttgaag tagattaagt    600

gtcgctgaac cattagtatt gttggaggta gccttctcca ctagaactgc cagtgcattc    660

agtgaactca tcatcctctg ccaaagagaa aacataactt ttaatgctaa aaccaataat    720

caaagaaaag gcaa                                                      734
```

<210> SEQ ID NO 94
<211> LENGTH: 1102
<212> TYPE: DNA
<213> ORGANISM: Zea mays

<400> SEQUENCE: 94

```
ggaataatta aatgctttgt caataaagtt ttagatagtt acttggtgaa gatatatata     60

tatatatata cacacacaca ataaatgtgt aaaaaccgag atttaaatca aaatgttgcc    120

tttttcagca atagtttcct gagatatata gtcaaaattc catgtggaca acaataagaa    180

tttgctatgg aatgctgaaa gtgaactttc ctgcttcata tattagctta tttgtggtag    240

aaaggtcacc tatttcattg caaatactta ctcgtatcca atggcatatt tgatgagagt    300

catgatcctg ttcctaacag agtcatatgc acctaagaat ccactgtgaa cctaaaacat    360

ggtgtgaaaa catgtcaggt agcagaaata tgagaacaga cacataaata gaaggaagag    420

tgtagacgac taacttgaac ttcttgtttg aagtcaccac ctagcctctc agggtttagt    480

ctgcaatcag gttcaaaaca tgttgtcatt gttgtgtcaa aggaacacaa aataacaaga    540

aaaaatacta ctaccatagc tacaatttct tccttaaatc ttacccagca ggtacaagca    600

ttaagtcggt tcgcaaatcc ttccaccttg actaggtaga catgcagaaa tcaatgcaaa    660

gcaaagtgaa taaagcttga atatatgcca aattataaag tgaatttgcc attaatagaa    720

cacaaggctt tcatgttaat gcatacttgt tcggttccac gaaaggcaac aaccaacctt    780
```

```
cttcgagaag aatcgcacca tatggcaacc tgaacatgtt aatataagct accaaaacaa    840

aggagactgg aaactcattg ataccgcaac aaaactcact tgtgtgtctg ttgaaatatt    900

gtcaagaaaa catatctttt caaagtccga cttgatgaaa ctgttacgtc ccagtgaagt    960

ggcaagcata gcccatgcct ccatggcagt ctctgcactt gcaaacaagc gccgcatatc   1020

ctctgcttcc tgtgcatcaa tggacagtaa cgcagatgaa acagtatcag ccttttgaac   1080

agaatctgca ggcatgcaag ct                                            1102
```

<210> SEQ ID NO 95
<211> LENGTH: 773
<212> TYPE: DNA
<213> ORGANISM: Zea mays

<400> SEQUENCE: 95

```
gcagtcgcca tcagtataac ggttacaggc caaattgcaa catccaggat cagtgtaagc     60

cagcaatgcc gtggcgtcaa attcaaatcg aattccttaa cctctcccaa gaacggccaa    120

agcctatttc tgtgacactg gcaacgagtg tagcaacagt cacactggca agcaagcaag    180

cagcaccagc gtttactcaa agtcgcaaac caacgaaatg ccatggcgaa gctattgtgg    240

aagctggcgt acgtcgagca ccagcgctac gcccagcgtc ggctcgtcgt gtgtcaagtc    300

tggacattgt gtaatttgga ggatcgcaga aaaataaata actcgtggag tttggacaaa    360

tccagccggt ccttatcagt tagttcaggc tatacaaaga cgacaatgca cacgtcgcca    420

ccaatcttgt tttacttggc tttgtccact gcacttctgc tgcggtatat atatatatat    480

aagccgctct gctagcagaa gcaaaacatg catcgggaac ccttacaggt agataccaca    540

accctgtgca gagttcttgc agtctcatca aggtgacagg aacgacatag gacatggagg    600

ccaccctgag cccgaagccc catttcgtgg tcatcccatg gccagccacc agccacatga    660

tccccatcgt ggacatcggc tgcctcctcg ccgcgcacgg ggcccgggtc acgatcatca    720

ccacgccctc cagctcgcaa ctcgtccaga gccgcgtgga ccgcgccggg caa           773
```

<210> SEQ ID NO 96
<211> LENGTH: 502
<212> TYPE: DNA
<213> ORGANISM: Zea mays

<400> SEQUENCE: 96

```
ccgaggggcc ctccattgat aatagtaatc agaatattac accaaatggg ctagaaactg     60

gagcacctcg aaacgaagat acagaacaaa ctacattaga ccggccaact agacacacaa    120

ccgaccacgg ccgtcacatc aaagcatcag aaggggaggc ggcctagccg ccgaagccgt    180

agagcgtccg gccctggcgc ttgagcgcgt agacgacatc catggcggtg acggtcttgc    240

ggcgggcgtg ctcggtgtag gtgacggcgt cgcggatgac gttctcgagg aagatcttga    300

gcacaccgcg ggtctcctcg tagatgagcc cagaaatgcg cttgacgccg cccctcctgg    360

ccagcctacg gatcgccggc ttcgtgatgc cctggatgtt gtcgcgcagc accttgcggt    420

ggcgcttggc tcctcccttg cccagcccct tgccgccctt gccgcgcccc gacatcgccg    480

aaaccgagag ctacgcggac ga                                             502
```

<210> SEQ ID NO 97
<211> LENGTH: 740
<212> TYPE: DNA
<213> ORGANISM: Zea mays

<400> SEQUENCE: 97

```
agctcggacg gaggaagctc cagtcgacag caaagactac tggggcgcgc actcacttcc     60

acggccactg ggtctcggac tcaccgtgaa gccacggcaa tctgatggac atggactagg    120

ttaacatctc ctgagcctga aacgtgacag ctgacatggg tcagagtgaa aagaaaatta    180

gtttaggcat taggggacac gacgcagaac ggggtggctc gaggccaagc gggcggcgga    240

cccgagcgga taaggacgag ctcggccctc aactgtcgct gctgtggcgc atgacacaaa    300

cacaaagcat ggtttcctgt tggtaattta ccaccactag cgctagccta caactggtat    360

gttttttgtt tttgtttttt tttgcattgg atcgtagaat tataaacttt ataatatgcc    420

ataaaagctg aaggttgcag tattagttta aattattcta tttgttaatt taaaacgttg    480

tcgcaggctc gcagctgctg ttgctgtctg ctttcccctc ccccggtcta caaagacctc    540

ggctttcctt tcctacatgc tcttcttcct tccaaagcct tcgcattttt cctctcgtct    600

tccccttccc cttactccaa attacccccct gctatctaca tatcctgtcc acactttcct    660

tccctgcgct gggccttgga gtttttggt tgtgtatcgg gggaaatggg aaatcgacga    720

cgaaattgcc gatcaatagt                                                740
```

<210> SEQ ID NO 98
<211> LENGTH: 716
<212> TYPE: DNA
<213> ORGANISM: Zea mays

<400> SEQUENCE: 98

```
tgctgggatt tgtgcgttgt ctactgttag gcagtctcgg aaagcaaact ggggcagctg     60

ataatctgaa acacggccag ctaaagcagt agcttcagcc tcaagtgaac tatgtccggt    120

aggtgtaggt ggatgtgcaa catcacctag caattgttcg atgacaggta tgaaaggcga    180

gcctctctcc ccagttggca atgaatgcct attggccaat tccatagcag gctctgggtc    240

cttttcgctt gaatttggaa ggttttctgc cagtagaaca ctgttgtccc accaatcttg    300

cacaaagctg ttagtgctaa gatcaagcat catagtttcc agcagactgt tgtttccact    360

acagtccttc atgttgtttt ctagagtttc agcagtagct tcttcaggtg atctgttagg    420

taattcagga aatgtactgt taccctggct tgtaaagtcg gcagtatcct tgaattgact    480

tgagtcacct tgaacaatga aggattcttc ttgtgagagg agcctcacag attctccagg    540

gtcaggtatc agggattgtt cgtgcatgag ggcatggtat ggtgataggc gattttcttg    600

gaatttagaa gcacaagggt tgctgccgaa tgatacagat ttacatagaa acttgtcact    660

ctcagtatgc agggcaatct ttaacttttc ccctgatact gctgtaaacg atgacg        716
```

<210> SEQ ID NO 99
<211> LENGTH: 781
<212> TYPE: DNA
<213> ORGANISM: Zea mays

<400> SEQUENCE: 99

```
tgacccatgg gcgaggaggc aatcacgctc ccatttcccc aaacttgact ccaccgaacc     60

ttttcctgtc agcgacaggc tgcctcgtga gggggtggac cggcccagta ttacggtatt    120

tcaccttatc ttcggacata tgaatcagcc tctggtaaaa ggtagggccc atgaaaacca    180

aggattccat tctttcacca gttcgaccat ttagaacgtt ctcggctccc catcgtgaat    240

aaccagccct gcaatgcaac aagatacata gaaagttgtg tgtttccgcc attttgagca    300

aaatattaca aaaagagaca caaatgtgaa actactgtaa actaagagat actaggaaca    360

atgcagtaca tgtttattca gatgaccaat atacaaaatg aggttagcca cactattctc    420
```

tctctgtgta atttatttct ctacctttct tttttcttct tctgcatgtg taataagcag 480
taaagtatta acagagttaa gacttcagag cattcgatgc attaatgacg tacaaggttc 540
ttataagatg tactaattta aggcaagcaa ctattcatcc tttgagaggg tctcatatat 600
ttgtttcgtg tgcaaggagt ggtttactga atcaaggcaa gcaactagtc atcctttaga 660
agaagaaaca cttacttgtg caactgttct gcaataacat caactgatgc tgtggtgaat 720
ggtgttgcgt atctcattgt acctttgcag gctattccct tcccaagagc agcttcaagc 780
a 781

<210> SEQ ID NO 100
<211> LENGTH: 550
<212> TYPE: DNA
<213> ORGANISM: Zea mays

<400> SEQUENCE: 100
tgagcaacaa aagaaaagtg ttagaatata acgattaaca catgtccacc aaactgtcag 60
aacgaaaggc taaaacagca cacgatattg caaggcaata aataaaacag gaggtagatg 120
ttaacgtgta aatataaatc caagcaaacg agcaagtgtc tcgatatgtt ctttgttcaa 180
ttgtgaccta gttgtatccc cttaattaat cccttatcta tcatttcacc agttgccttt 240
gtctggatgt atcactaaac atcattattc aattgcagaa cagaaaataa atctactaca 300
agattgagat tcattcaatg gaagactaag aatgtaaaaa aaagagcata catagggcct 360
gtttggaata gctctagctc caagaccaat acaggatttg gagtttgtag tatgaaataa 420
acgggtataa acatttgttc aatatgcccc caactccagc cccaagaatt tatagagcta 480
cagatgacca gctcaaaaaa atctgggaga gctctaccat gccaacatca gaaacaaaaa 540
ctgtaatgcc 550

<210> SEQ ID NO 101
<211> LENGTH: 616
<212> TYPE: DNA
<213> ORGANISM: Zea mays

<400> SEQUENCE: 101
tgcacgtggt tcctgtgacg accgcctcaa gtcaagtggg atgggagctc caacgttttc 60
catttgccac acaggtagtg aaggcgagtt tggcgtgtgt gctatgccga tgccagtgcg 120
tactgcgtag cctagtcccg tccatcacat tgcagtttca attgtcaatg gaacacatat 180
atctgcgtag tttccttcac tgatctctat cggtgcatca tcaaaactca aagtcagagt 240
aatctccact acaaatctcg agaacaaatg acaatctgac aagaaatcta acgtacgaat 300
aactatttcc ttcttggcac ggctgtaact attacgtact attctttttt tattatttga 360
aatggtgtac aagtgacatg gtacaacaca agagaacccc aaaaaaaaaa ctttcggtgt 420
tttcttgtga catcctcggt acagtcaccc aggtgacaga tttgcagtca agaagaagag 480
gcgatgagct acggacattt tcagtggtaa tcatattaga ccagaagatc cgcaaaaaaa 540
aagttgccat tgctggacag taatagtaca catttttttt ccttcctttg ctaagtcata 600
cgattcaaac cgcaga 616

<210> SEQ ID NO 102
<211> LENGTH: 719
<212> TYPE: DNA
<213> ORGANISM: Zea mays

<400> SEQUENCE: 102
tcgacgacaa tttgaggagc agaaggaaag acatgatgag acattgccaa cgtgaaggtc 60
gaagcattct taccagtagg tcttggtctc aatgtggaac aggaagcggt gcaaagtgta 120
ttcgatcagc gtccaaataa atatcccaaa tagagccatc atagctacgt cctgaacggt 180
atgacccatc agaatagatt tcacgagcag gcagcagaca acaggcagcc atatagttgg 240
cacagcccac cacttcgtgc gagtcaagaa ctggacagtc caagaagttt gttagtacgg 300
ttaccaaaac ccctaggata ccattaccaa tgcgatggga tatgcgttac ctccaggaca 360
tcatttccga aaaagcgtgg accctccttg ctgacgatcg gttggtgaac ccattcctgg 420
taccgttcct caagatggcc aacctgcatc cacaaaatca agagacaacc agaagatggt 480
tatgtgaatg cgaaccacgt gaagcagctg gacatcgact cagaaactcg gaagtttaca 540
actactacat gagattccgc tttcatgata gaatctgcca caattattgc tgaggagaaa 600
gcacagtcta acactaaggc ctggttgcga aaagacccaa agctgcatta aacaagctca 660
aaagtacata ataacttgta aagtgcgaga gagaatccca taagcctact caaaaaggc 719

<210> SEQ ID NO 103
<211> LENGTH: 643
<212> TYPE: DNA
<213> ORGANISM: Zea mays

<400> SEQUENCE: 103
ggaggaggcc gaggtggcga gcgtgccgcc gccgcaggcc gcggagaagg aggcgaggaa 60
gggggacgcg cagtccctgc cgcggcagcc tttggcggag agcaagaaca tgagccgcga 120
gtacggcggg cagtggctga gcagcaccac gcggcacgtc cgcatctacg ctgcgtacat 180
cgacccggtg accaacgcgt tcgaccagac gcagatggac aagctgacgc tcatgctcga 240
cccccaggac gagttcgcct ggaccgacga ggcctgccag atggtcttca acgagttcca 300
ggacctcgtc gatcactacg aggtaacctc tgtagttgct cccacagtcc cactccaaca 360
gctccgatag tagataaaaa aaatttgaat tgaatctctt gttgtctgaa attcgtacgg 420
tcatttcccc ccttttcatc tactttagag ccactcctgc caaaaaaata aaacatacgg 480
tcttggcaaa agaagtgatc ggtaagagga tagctgagct cgtttctgct ttgaaacagg 540
gggctgagct gtcggagtac acacttcggt tgatcgggtc agaccttgag cactacatcc 600
gcaaactgct gtacgacggg gtgatcaagt acaacatgag gtc 643

<210> SEQ ID NO 104
<211> LENGTH: 799
<212> TYPE: DNA
<213> ORGANISM: Zea mays

<400> SEQUENCE: 104
tttgtttgta gctttgttat tacttgctac attgctagat gtcccacaac tatatgagtt 60
ggagagaatc tagaattcga actcaactgt ttagtcaatg ctgaatttgc agactagata 120
atacttcacc gatatggaat cttttgtatg gtgtatttgt tgcttccttt catcttaatg 180
tttttcatca tggttgttgc atgtatatgc atagaaaaaa atggtgtaga taattttgca 240
ttgcatttta aggtcatatc tttatcttct aagtcatctg caatgtagta tttggtaaca 300
aaaactttgc tatttctttc catacagtat taccactatg cggttctaaa atgttctgta 360
aatttcttgt gcagaatgga tgaagctcgg cagccattgt ccagaaaagt tccaatatcg 420
tcaagccgaa taaatcccta caggatgatt atcgttatcc ggttggtggt gttgggtttc 480
ttcttccatt accgagtgat gcatccagcg aaagatgcat ttgcgttatg gctcatatct 540

```
gtaatctgtg aaatttggtt tgccatgtcc tggattcttg atcagttccc aaagtggctt    600

ccaattgaga gagagactta cctggaccgt ttgtcgctaa ggttagttgc atgttgaatg    660

gaataaactg ttgccaacta tctccattct aaagttccaa atctaagaag ttcattgctt    720

gtctgactag gtttgacaag gaaggtcaac cctctcagct tgctccaatt gacttctttg    780

tcagtacggt tgatcccac                                                 799
```

```
<210> SEQ ID NO 105
<211> LENGTH: 869
<212> TYPE: DNA
<213> ORGANISM: Zea mays

<400> SEQUENCE: 105

tttcgataag ttataaaccg ttgccaattt tattttcgcg agcccaatat agaattatac     60

atgaaaagcg cactggcttt attacaacta gtgcatgaga attgtagtag tccagcacca    120

gcaggatcat ggatgaagca gataaattgc aggaaacact tgtgacctag agttcgtctt    180

ttgctgcttc gaagcagtcc tcatcccaga cgaaggggaa tttcagtacc gcggctgtat    240

gaggcatgct ccaatcatca tataaaaatc tgcaacgagg atgtcattgg atctcagaaa    300

gaaaaatgtt gattgcagat atgattatgt gcgttttctg acatgcaatt gcaaacaggg    360

ggagaaaaga aacgcgtatg tggattactc agttgctgta ttatcaatat tgctagggtc    420

aacactagag cataaaagat gctactgaca tagataacaa aagtgcccat gacacgtgca    480

tgaaactatg atatctattc tagcaatgtt ggacaattac agaaaaaaat ggtaaatcaa    540

taaatcacag cagtataggt agcaaattct ccaatcaagt cttgtcaact tagtatggta    600

ctgagttgaa caagatggaa acataaggga atactctcta caaggttcac tgtaattcta    660

tgtccatgtt ctgcatttca gcttattctg tgttaggcaa tgacagccga aaactttttt    720

ggagtgataa atgggtttca gggaatatct gcgtgtgatc cccgctccac tttacacaca    780

tgtgggaaag agagcaatca aaaagaagat ggtgccggat gccttggaca ataatgcttg    840

ggtatggtac atcaaggggg ctgtcagct                                      869
```

```
<210> SEQ ID NO 106
<211> LENGTH: 423
<212> TYPE: DNA
<213> ORGANISM: Zea mays
<220> FEATURE:
<221> NAME/KEY: misc_feature
<222> LOCATION: (360)..(364)
<223> OTHER INFORMATION: n is a, c, g, or t
<220> FEATURE:
<221> NAME/KEY: misc_feature
<222> LOCATION: (385)..(388)
<223> OTHER INFORMATION: n is a, c, g, or t
<220> FEATURE:
<221> NAME/KEY: misc_feature
<222> LOCATION: (393)..(399)
<223> OTHER INFORMATION: n is a, c, g, or t

<400> SEQUENCE: 106

cggctgctgg gagcgcttcc gtgctcatgc tgttctgtga tacggcgcta tcctcgccga     60

gcttattcct cgacttccaa cctattcacc accgctgtca gaacccttct tgtgacaaaa    120

agttaagcga gcgtcttctt gaccttgcaa gactttttgt ccggagataa tctcctacga    180

attaccctct tgcatcttgc gactacctct cctcgtctcg cgcctgtcga tccttccatc    240

cctctcgtcc ccgtctatcc ctcttgagct tggaacactc tcgatcgcag ctagtagtag    300

ctagctatat attattgttt tcctttcacc tactttcgca tgaactactc tgctatttgn    360
```

nnnngctgga agttccaaaa aggtnnnngg ggnnnnnnnt gctacacttg ggtcagataa 420
ggc 423

<210> SEQ ID NO 107
<211> LENGTH: 728
<212> TYPE: DNA
<213> ORGANISM: Zea mays

<400> SEQUENCE: 107
tagttggctg aactgtacgg ctctagcttg aacagtttcc ttgcagctgc ctcggcaaga 60
gcaaggtttc catgtaccac gcaaccggtt agaagggctc cccataggct cgccgctgac 120
ttgaatggtg acctgttgat gaagtccgtc gcttcatcca ggtacccgca ccttgccaaa 180
agatcaacca tgcacgcgta gttctcaacg gtcggtgtca cgccgtatct gctctccatg 240
gcatcgaaat agtcccaccc ttcagtgatc aactccattg atctgcaagc agtgagcagc 300
gctgtgaagg ttatactgtc tggcttcaat cctgctcctg ctcctgcact agcagcacta 360
cacatgtcgt cgaacagcgc tattgcctca cggccctggc catgtgctgc cagcccggtg 420
agcatcgcat tccaggacac caaattcttc tcctcctgaa tcctttcgaa tatccgcgtt 480
gcacttgcca ggtttcctga cttggagtac atgtcgatta gggctgttgc aacaaccatg 540
tcgtggtcat acgctcttct tcgcagtgcg aagcaatgca gctccttccc tttcgccagc 600
aaagccagcc ctgcgcaagc ccgcagcaac acagacatgg taaccacgct aggctgggac 660
atggtccttc tgcatctcct tgaagaagta gaacgaatct tcgtagtctc cattatggca 720
gctcccgg 728

<210> SEQ ID NO 108
<211> LENGTH: 533
<212> TYPE: DNA
<213> ORGANISM: Zea mays

<400> SEQUENCE: 108
ttgcatcggc tcgacctctc gaacaaccgc atcgccggcg gggtctcgcc ggaattcaac 60
aggctccaga ggctcgctac tctgtacctg gagaacaaca gcctgaatgg cacgctgccg 120
tccaaccttg acctcccgaa gcttcagctt ttcaacgtgt ccagaaacaa cctcaccggc 180
cctgttccaa agtcgctcgc ccggatgccc gccagcgcct ttgatgggac agggctctgt 240
ggtgaccctc tagccccgtg cccaacccct ccgccgccgc cgccgccgcc tgttccggcc 300
gctgctaatg gtagcatcag cgcaaagctc tctactggtg cgatcgccgg cattgctgcg 360
ggtgctgccg tggcgttctt ggttctgatc gccgtgatct tgttcctctg ctttcggtgt 420
cagaggacaa tggccgaaaa atccgcggag acggcagccg acgccgacct ggacgggtct 480
cccgtgtcgg tcaccgtggc gagcatggac atgaagaacg cgacgaggcg gtc 533

<210> SEQ ID NO 109
<211> LENGTH: 564
<212> TYPE: DNA
<213> ORGANISM: Zea mays

<400> SEQUENCE: 109
tgtcgttctt ttttttattc catctgattt tgtgttatgt cacagtttat gatggtaagg 60
gaacccttga ggaaggggaa accgctgaag cgcgtttcat taagatccaa gcagcgtatg 120
agctgttgat tgatggtgaa aggagaagag catatgatag agagcatcat gtgaatccga 180
tgaaggtctg aatttttcttg gccacttagg ttatcatttc attatgtgca ggatgcagtt 240

-continued

```
cctccactcc atctttgtat ttgtttgtta attactgttg tctgttgcca cctattttac    300

tcgaggatta cacattttag tcacagtatt agttttttaa tcctgattta gcttcatggt    360

tctcaagcca agaaaaggaa gcatcattcc atccttgtca gctactaact tacaaagcag    420

taatgtgtct tactttgttt ttcttgcttc aaaactggac taggactgat ggaatatatc    480

agcaactaac aactgctaat tacacgtggg tccaacattc atatgccttg aaatagttga    540

gcacttgaga ccttattatc tgca                                           564


<210> SEQ ID NO 110
<211> LENGTH: 255
<212> TYPE: DNA
<213> ORGANISM: Zea mays

<400> SEQUENCE: 110

cttggttgcc gttttcttgt actagatgaa gtcgaccagc ttctgtcttt taattaccgt     60

gaagatatgc atagaatttt ggagcatgtt ggaaggagac ctggaggcac atctagggat    120

attcttggcc cacttgcgag acgatctgag cgtcagacta tcctggtttc tgcaacaata    180

ccattttcag ttatacgagc agcaaggagt tggggtcatg atccagttct cattagagct    240

aaaagtgtag ttcca                                                     255


<210> SEQ ID NO 111
<211> LENGTH: 255
<212> TYPE: DNA
<213> ORGANISM: Zea mays

<400> SEQUENCE: 111

agctcggcct cttccatttc tgatcactgt ccgttgttac tcggattgca tgacttcttt     60

atgggtagga gatggtttca tttcgaaagc ttttggccct ggttggatgg gtttgtggag    120

gaggcccaga tgtcctggaa tcaacatgtt gatgctaact gtcccctgaa aaagatttgc    180

tgacaagcta agtcgacttt ctagtgattt gcagtcctgg aatcacaaaa aaaactggtc    240

atattaagca gcaaa                                                     255
```